(12) United States Patent
Wu et al.

(10) Patent No.: US 8,980,904 B2
(45) Date of Patent: Mar. 17, 2015

(54) HETEROCYCLIC SUBSTITUTED PYRIMIDINE COMPOUND

(75) Inventors: Yongqian Wu, Jinan Shandong (CN); Aichen Wang, Jinan Shandong (CN)

(73) Assignee: Xuanzhu Pharma Co., Ltd., Shandong (CN)

( * ) Notice: Subject to any disclaimer, the term of this patent is extended or adjusted under 35 U.S.C. 154(b) by 0 days.

(21) Appl. No.: 14/233,823

(22) PCT Filed: Jul. 19, 2012

(86) PCT No.: PCT/CN2012/000973
§ 371 (c)(1),
(2), (4) Date: Apr. 11, 2014

(87) PCT Pub. No.: WO2013/010382
PCT Pub. Date: Jan. 24, 2013

(65) Prior Publication Data
US 2014/0288063 A1    Sep. 25, 2014

(30) Foreign Application Priority Data

Jul. 21, 2011 (CN) .......................... 2011 1 0204862
Nov. 25, 2011 (CN) .......................... 2011 1 0380109

(51) Int. Cl.
*A01N 43/54* (2006.01)
*A61K 31/505* (2006.01)
*C07D 498/08* (2006.01)
*C07D 403/04* (2006.01)
*C07D 401/04* (2006.01)
*C07D 401/14* (2006.01)
*C07D 403/14* (2006.01)
*A61K 31/506* (2006.01)

(52) U.S. Cl.
CPC ............. *C07D 498/08* (2013.01); *A61K 31/506* (2013.01); *C07D 403/04* (2013.01); *C07D 401/04* (2013.01); *C07D 401/14* (2013.01); *C07D 403/14* (2013.01)
USPC .......................................... 514/273; 544/320

(58) Field of Classification Search
CPC ... C07D 401/04; C07D 403/04; A61K 31/506
USPC .......................................... 544/320; 514/273
See application file for complete search history.

(56) References Cited

U.S. PATENT DOCUMENTS 7,087,597 B1 * 8/2006 Miwa et al. ............... 514/212.08
2004/0142930 A1    7/2004 Yamada et al.

FOREIGN PATENT DOCUMENTS

WO    WO 0127105 A1    4/2001

OTHER PUBLICATIONS

R. Basson, 11 Journal of Women'S Health & Gender-Based Medicine, 367-377 (2002).*
C-S Lin et al., 268 Biochemical and Biophysical Research Communications, 638-635 (2000).*
English language abstract for WO 0127105 extracted from espacenet.com database on Jun. 2, 2014, 2 pages. Also see English equivalent US 7087597.
International Search Report for PCT/CN2012/000973 dated Oct. 4, 2012, 7 pages.

* cited by examiner

*Primary Examiner* — Alexander R Pagano
(74) *Attorney, Agent, or Firm* — Howard & Howard Attorneys PLLC

(57) ABSTRACT

The present invention pertains to the field of medical technology, and particularly relates to a heterocyclic substituted pyrimidine compound represented by General Formula (I) and its pharmaceutically acceptable salt thereof, wherein $R^1$, $R^2$, $R^3$, $R^4$ and $R^5$ are as defined in the description, the present invention also relates to a preparation method of the compound, a pharmaceutical composition containing the compound, and a use of the compound and the pharmaceutical composition in preparation of a medicine for enhancing a cGMP signal transduction function or a medicine for treating or preventing sexual dysfunction and diseases with lower urinary tract symptoms.

(I)

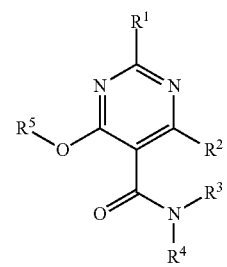

13 Claims, No Drawings

HETEROCYCLIC SUBSTITUTED PYRIMIDINE COMPOUND

RELATED APPLICATIONS

This application is the National Stage of International Patent Application No. PCT/CN2012/000973, filed on Jul. 19, 2012, which claims priority to and all the advantages of Chinese Patent Application No. 201110204862.2, filed on Jul. 21, 2011 and Chinese Patent Application No. 201110380109.9, filed on Nov. 25, 2011, the contents of which are incorporated herein by reference.

TECHNICAL FIELD

The present invention relates to the field of pharmaceutical technology, specifically relates to a heterocyclic substituted pyrimidine compound, its pharmaceutically acceptable salt or stereoisomer thereof, a method for preparing these compounds, and uses of these compounds in manufacture of a medicament for enhancing cGMP signal transduction.

BACKGROUND ART cGMP (guanosine-3',5'-cyclic monophosphate, cyclic GMP) is a cyclic nucleotide, exists in cells of animals and plants, is a second messenger widely participating cell reactions, and it can be hydrolyzed by PDE-5(phosphodiesterase-5). When PDE-5 is inhibited, the level of cGMP would increase and result in many physiological effects such as vascular smooth muscle diastole. Hence, PDE-5 inhibition can be used for diseases caused by cGMP signal transduction disorder. These diseases include hypertension, heart failure, hypertension pulmonary, erectile dysfunction, prostatic hyperplasia and female sexual dysfunction, among others.

Erectile dysfunction (ED) is the most common sexual dysfunction in adult males, it refers to a disease that penis is continuously unable to achieve or maintain an erection to enjoy sexual life. ED includes organic ED, psychological ED and mixed ED. Although ED is not lethal disease, it has a strong impact on life quality and spouse affection.

There are many therapies for treatment of ED, mainly comprises three groups: peripheral drug therapies, central drug therapies and genetic therapies. Peripheral drug therapies principally refer to administration of phosphodiesterase-5 inhibitors (e.g., sildenafil), as well as administration of papaverine, soluble guanylate cyclase activators, Rho kinase agonists and topical alprostadil. Central drug therapies refer to therapies using drugs such as dopamine receptor agonists, a adrenergic receptor antagonists, 5-hydroxytryptamine (5-HT) receptor agonists, oxytocin and oxytocin receptor agonists. In genetic therapies, on the basis that ion channel is an important material basis for regulation of corpus cavernosum smooth muscle tension, plasmid vector hMaxi-K (pVAX-hSLO) expressing hSlo gene is injected into corpus cavernosum. This plasmid is expressed in corpus cavernosum smooth muscle, and generates more potassium channels so as to render corpus cavernosum relaxation.

Currently, there are many therapies for ED, among which phosphodiesterase-5 (PDE-5) inhibitors with sildenafil (Vigra) as representative are first-line drugs for treatment of ED, and are the most popular therapy in patients. At present, PED-5 inhibitors in market include Sildenafil, Vardenafil, Tadalafil, Udenafil and so on, as well as Avanafil in phase III of clinic test. Sildenafil and Tadalafil are most profitable products of Pfizer and Eli Lilly Company, respectively. Hence, these drugs are promising in market.

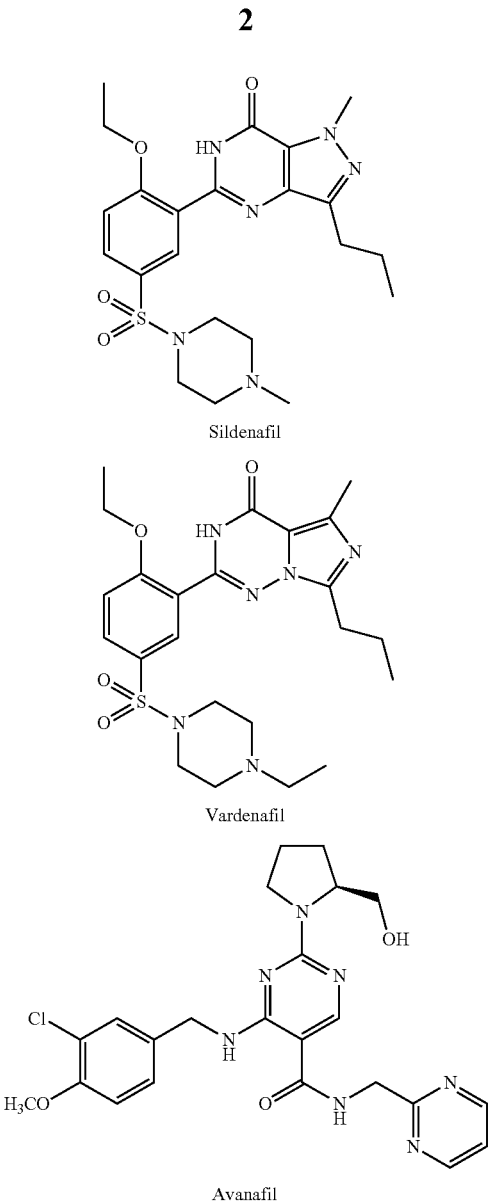

Sildenafil

Vardenafil

Avanafil

With the clinical application of PDE-5 inhibitors, some latent safety problems gradually appear, among which Sildenafil and Vardenafil inhibit PDE-5 but at the same time inhibit PDE-6 to some extent. PDE-6 influences retinal function, so that these two drugs may influence human vision, and more reports are reported on Sildenafil. Tadalafil has better selectivity on PDE-6, but still has inhibition effects on PDE-11 to some extent. Although the clinical pharmacological effects of PDE-11 are unknown, there is latent risk. It is reported in some documents that Tadalafil may cause low back pain, but it is needed to demonstrate the relevance of the low back pain associated with PDE-11. In addition, Tadalafil has a too long half-life, with about 16 h in human body, which may readily result in interaction with other drugs. For example, when nitrate drugs and Tadalafil are used together, blood pressure may drop low too much, thereby causing life risk.

Avanafil belongs to the second generation of PDE-5 inhibitors, which has good selectivity to PDE-6, ratio of PDE-6/5 is about 120, but it does not inhibit PDE-11, which ensure safety for clinical treatment. However, this drug has poor in vitro enzymatic activity, and its clinical dosage is very high (50 mg, 100 mg and 200 mg), higher than that of Sildenafil, Vardenafil and Tadalafil, which also results in safety risk for clinical treatment in patients. In addition, with the increase of dosage, therapeutic cost increases as well, so that Avanafil should be further improved at least in view of pharmacoeconomics.

In view of epidemiology, many aged male ED patients also have other urogenital diseases, such as lower urinary tract symptoms (LUTS), for example, benign prostatic hyperplasia (BPH), overactive bladder (OAB). These diseases may bring about great pains to aged patients, and severely influence their life. The pathologic analysis show that ED and LUTS have same pathogenesis, both relate to smooth muscle contraction or smooth muscle proliferation. Thus, PDE-5 inhibitors may also be used to treat LUTS with the same pathogenesis. At present, both of the marketed Vardenafil and Tadalafil had been used in clinical test for treatment of LUTS, and explicit therapeutic effects were obtained. Avanafil has a short half-life period with about 1.2 h in human body. Due to its short half-life, it can be used merely in treatment of erectile dysfunction, but is not suitable for treatment of diseases such as BPH, OAB. Hence, it still has very important significance for improvement of life quality (treatment of ED and LUTS) in aged patients to develop PDE-5 inhibitors with more potent pharmacological activity, higher safety, and suitable (relatively long but not too long) half-life.

SUMMARY OF THE INVENTION

The present invention provides a PDE-5 inhibitor with high safety and potent activity, and its specific technical solution relates to a compound of Formula (I), a pharmaceutically acceptable salt or stereoisomer thereof:

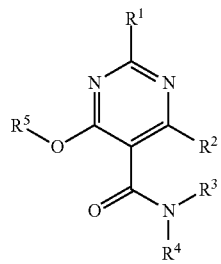

(I)

Wherein $R^1$ represents 6-7-membered nitrogen-containing hetero fused ring group, 7-12-membered nitrogen-containing hetero spiro ring group, or 7-12-membered nitrogen-containing hetero bridged ring group, each of which is linked to pyrimidine ring via N and is unsubstituted or substituted with 1-4 substituents, the substituents are selected from halogen atoms, cyano, amino, hydroxyl, $C_{1-6}$alkyl, halo$C_{1-6}$alkyl, hydroxy$C_{1-6}$alkyl, $C_{1-6}$alkoxy, $C_{1-6}$alkylcarbonyl or $C_{1-6}$alkoxycarbonyl;

$R^2$ represents hydrogen atom, hydroxy, amino, cyano, $C_{1-6}$alkylamino, di($C_{1-6}$alkyl)amino, $C_{1-6}$alkyl, halo$C_{1-6}$alkyl, hydroxy$C_{1-6}$ alkyl or $C_{1-6}$alkoxy;

$R^3$ and $R^4$ each independently represent hydrogen atom or -M-$R^7$,

M represents a single bond, or $C_{1-6}$alkylidene (—$(CH_2)_t$— (t is an integer from 1 to 6)) unsubstituted or substituted with 1-4 substituents, $R^7$ represents a cyclic group other than adamantly, which is unsubstituted or substituted with 1-4 substituents, or $R^3$ and $R^4$ together with the nitrogen atom to which they link form a 5-7-membered nitrogen-containing hetero ring group unsubstituted or substituted with 1-4 substituents, the substituents are selected from halogen atoms, hydroxy, cyano, amino, $C_{1-6}$alkylamino, di($C_{1-6}$alkyl)amino, oxo, $C_{1-6}$alkyl, hydroxy$C_{1-6}$alkyl, halo$C_{1-6}$alkyl, $C_{1-6}$alkoxy, $C_{1-6}$alkylcarbonyl, $C_{1-6}$alkylsulfonyl or di($C_{1-6}$alkyl)phosphino;

$R^5$ represents hydrogen atom or -Q-$R^8$,

Q represents a single bond, or a $C_{1-6}$alkylidene (—$(CH_2)_t$— (t is an integer from 1 to 6)) unsubstituted or substituted with 1-4 substituents, $R^8$ represents 6-14-membered aryl, 5-7-membered heteromonocyclic group or 6-14-membered fused ring group, each of which is unsubstituted or substituted with 1-4 substituents, the substituents are selected from halogen atoms, hydroxy, $C_{1-6}$alkyl, halo$C_{1-6}$alkyl, carboxyl$C_{1-6}$alkyl, $C_{2-6}$alkenyl, $C_{2-6}$alkynyl, $C_{1-8}$alkoxy, halo$C_{1-8}$alkoxy, amino, $C_{1-6}$alkylamino, di($C_{1-6}$alkyl)amino, cyano, nitro, $C_{1-6}$alkylcarbonyl, sulfonylamino or $C_{1-6}$alkylsulfonylamino.

In Formula (I), $R^1$ represents, for example, 6-7-membered nitrogen-containing hetero fused ring group, 7-10-membered nitrogen-containing hetero spiro ring group, or 7-8-membered nitrogen-containing hetero bridged ring group, each of which is linked to pyrimidine ring via N and is unsubstituted or substituted with 1-3 substituents, the substituents are selected from halogen atoms, cyano, amino, hydroxy, $C_{1-6}$alkyl, halo$C_{1-6}$alkyl, hydroxy$C_{1-6}$alkyl or $C_{1-6}$alkoxy;

$R^1$ is, for another example, one of a group consisting of:

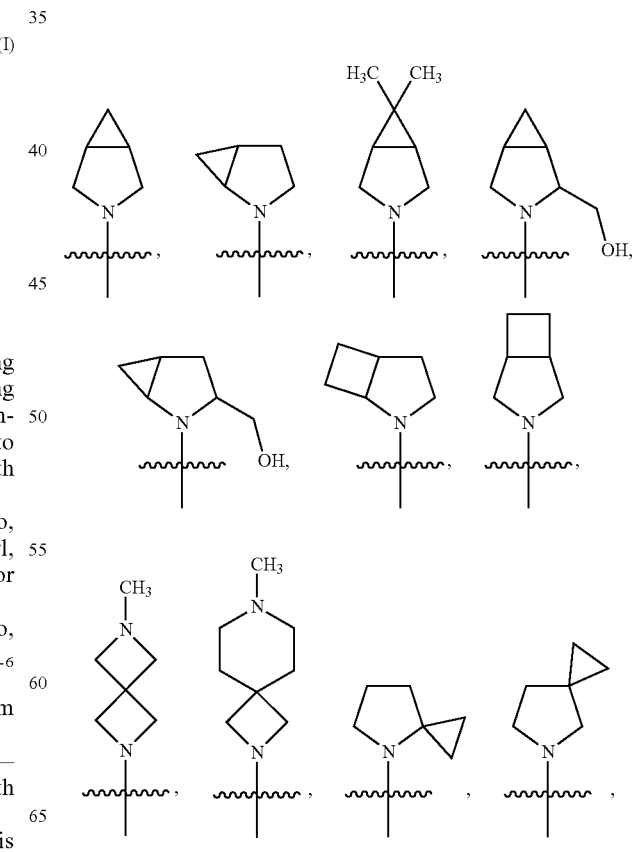

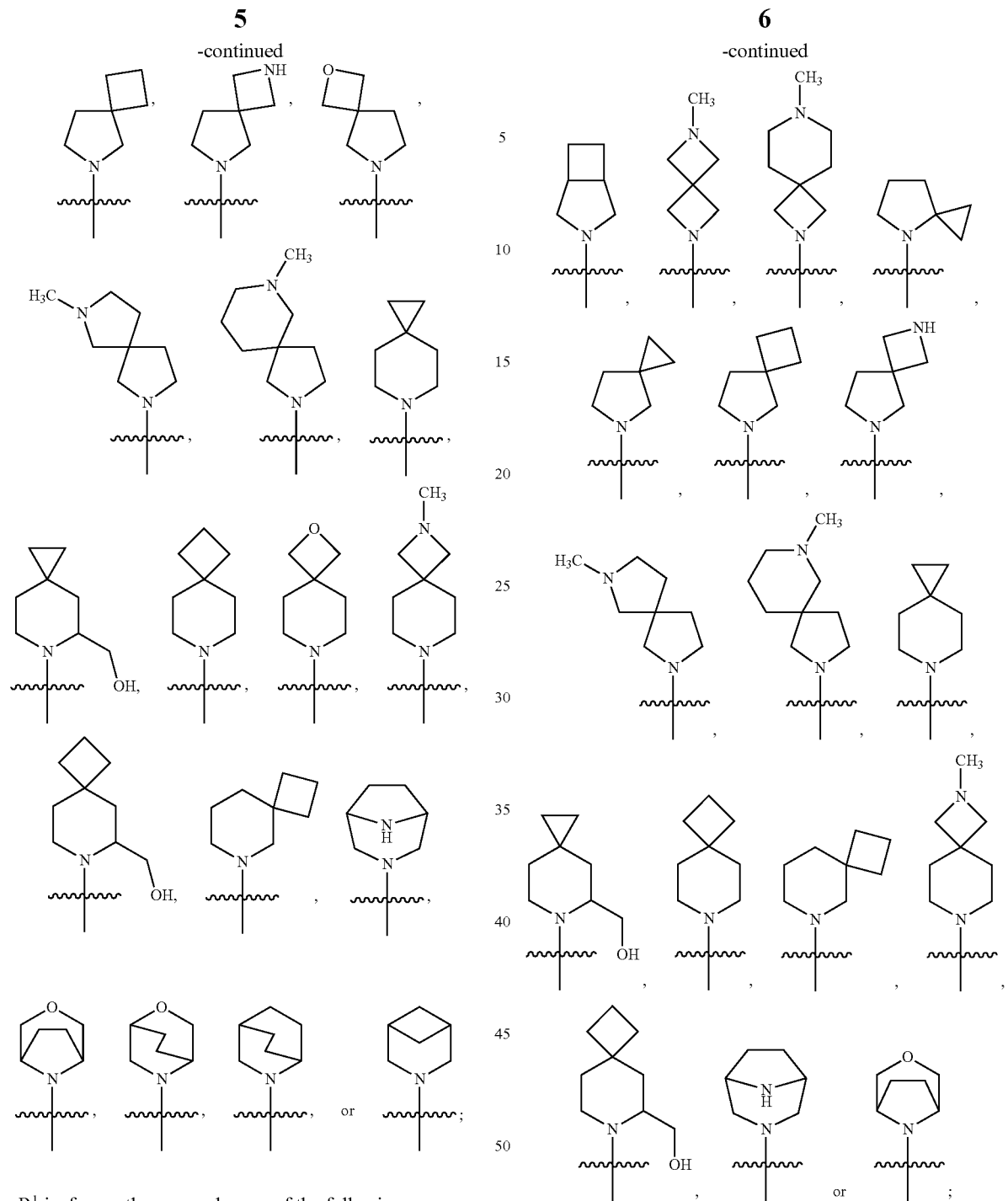
$R^1$ is, for another example, one of the following group:
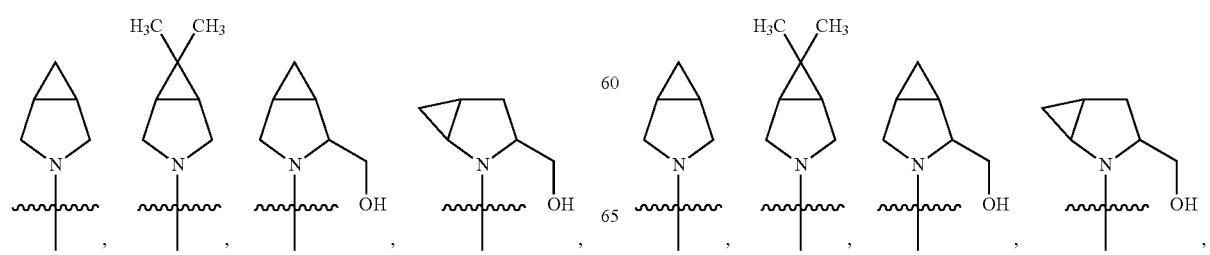

-continued

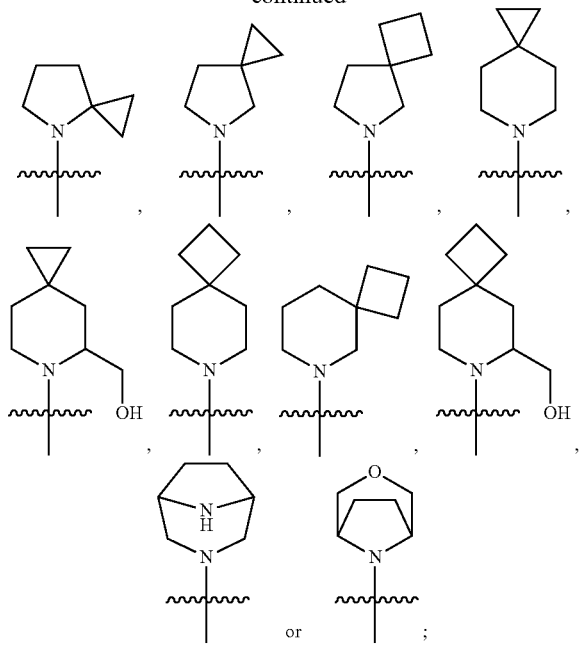

$R^1$ is, for another example, one of the following group:

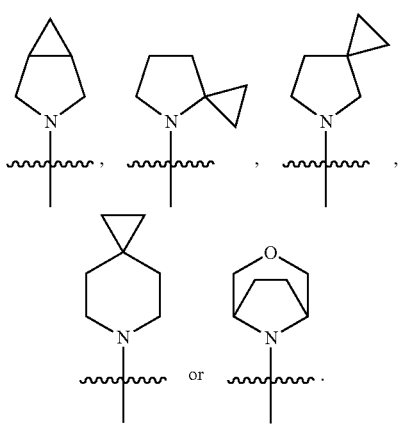

In Formula (I), $R^2$ is, for example, hydrogen atom, hydroxy or methyl; for another example, hydrogen atom.

In Formula (I), $R^3$ is, for example, -M-$R^7$,

M represents a single bond or $C_{1-6}$alkylidene (—$(CH_2)_t$— (t is an integer from 1 to 6)) unsubstituted or substituted with 1-4 substituents, $R^7$ is selected from phenyl, 5-7-membered heteromonocyclic group, 4-7-membered cycloalkyl, 6-14-membered fused ring group, 7-10-membered spiro ring group, or 7-10-membered bridged ring group other than adamantyl, each of which is unsubstituted or substituted with 1-3 substituents, or $R^3$ and $R^4$ together with the nitrogen atom to which they link form a 5-6-membered nitrogen-containing hetero ring group, which is unsubstituted or substituted, the substituents are selected from halogen atoms, hydroxy, cyano, amino, $C_{1-6}$alkylamino, di($C_{1-6}$alkyl)amino, oxo, $C_{1-6}$alkyl, hydroxy$C_{1-6}$ alkyl, halo$C_{1-6}$alkyl or $C_{1-6}$alkoxy;

$R^3$ is, for example, -M-$R^7$,

M represents a single bond or $C_{1-6}$alkylidene (—$(CH_2)_t$— (t is an integer from 1 to 6)) unsubstituted or substituted with 1-2 substituents, $R^7$ is selected from phenyl, 5-7-membered heteromonocyclic group, 4-7-membered cycloalkyl, 8-10-membered fused ring group, 7-10-membered spiro ring group, or 7-10-membered bridged ring group other than adamantyl, each of which is unsubstituted or substituted with 1-3 substituents, or $R^3$ and $R^4$ together with the nitrogen atom to which they link form a 5-6-membered nitrogen-containing hetero ring group, which is unsubstituted or substituted, the substituents are selected from halogen atoms, hydroxy, cyano, amino, $C_{1-6}$alkylamino, di($C_{1-6}$alkyl)amino, oxo, $C_{1-6}$alkyl, hydroxy $C_{1-6}$alkyl, halo$C_{1-6}$alkyl or $C_{1-6}$alkoxy;

$R^3$ is, for example, one of a group consisting of:

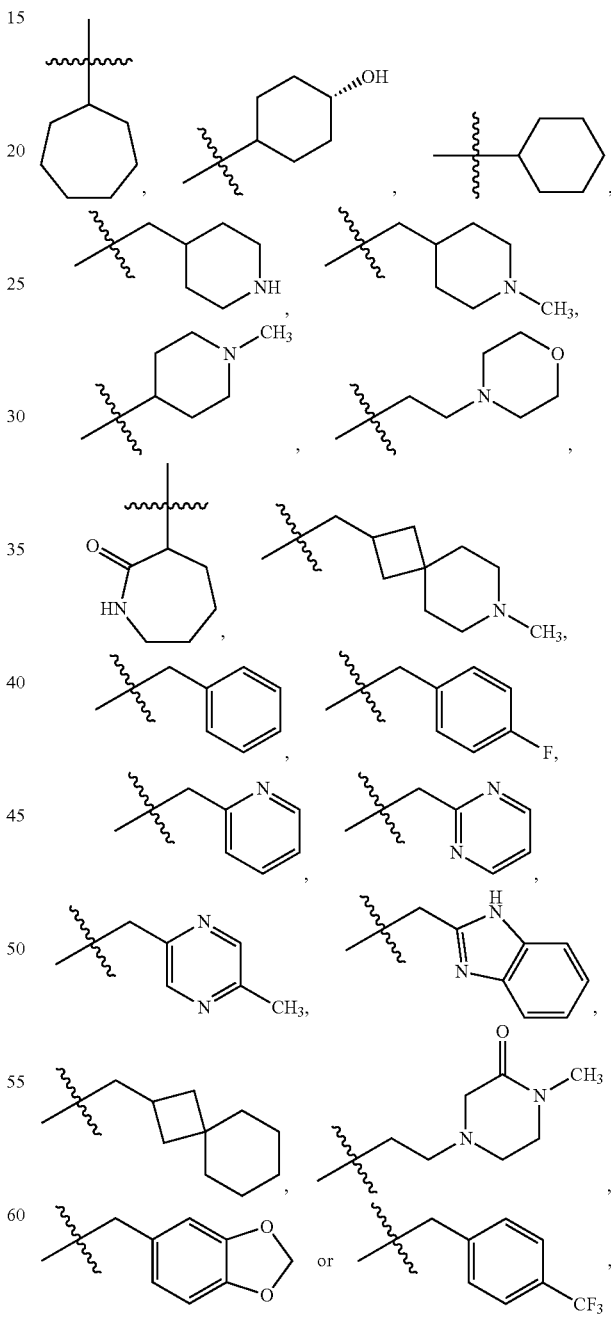

or $R^3$ and $R^4$ together with the nitrogen atom to which they link form:

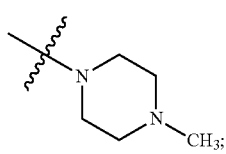

R³ is, for example, one of a group consisting of:

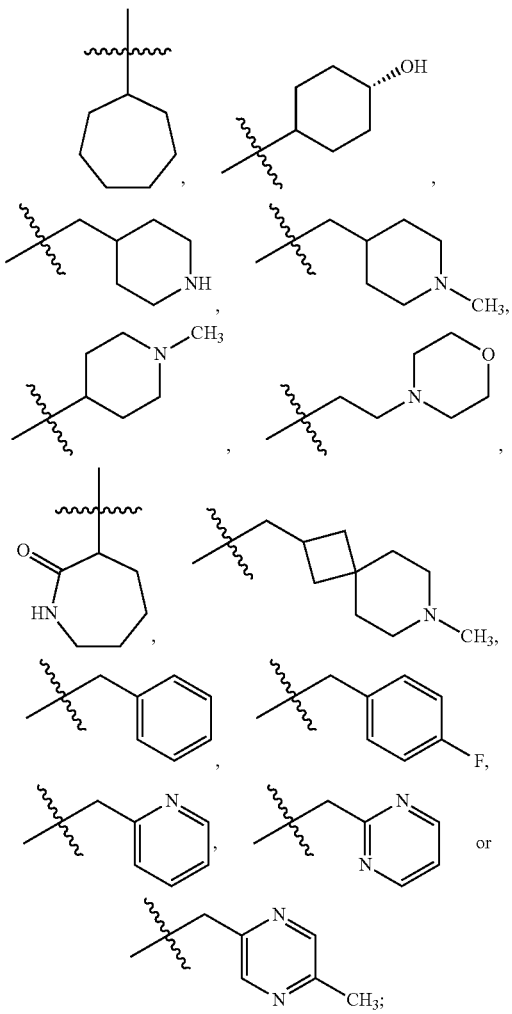

R³ is, for example, one of a group consisting of:

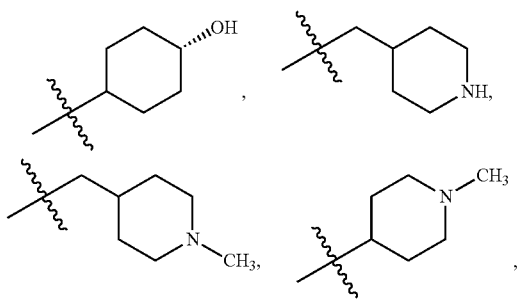

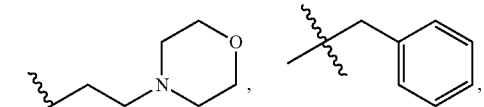

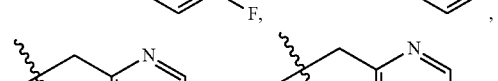

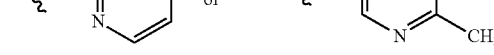

R³ is, for example, one of a group consisting of:

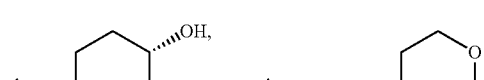

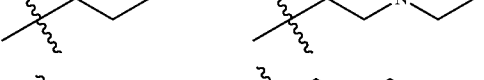

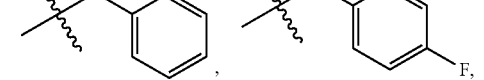

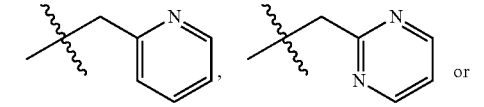

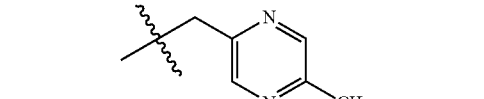

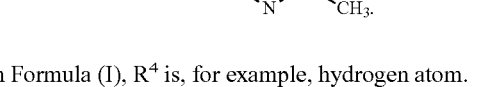

In Formula (I), $R^4$ is, for example, hydrogen atom.

In Formula (I), $R^5$ is, for example, $-Q-R^8$,

Q is selected from $C_{1-6}$ alkylidene ($-(CH_2)_t-$ (t is an integer from 1 to 6)) unsubstituted or substituted with 1-3 substituents, $R^8$ is selected from 6-14-membered aryl, 5-7-membered heteromonocyclic group or 6-14-membered fused ring group, each of which is unsubstituted or substituted with 1-3 substituents, the substituents are selected from halogen atoms, hydroxy, $C_{1-6}$alkyl, halo$C_{1-6}$alkyl, carboxyl$C_{1-6}$alkyl, $C_{1-8}$alkoxy, halo$C_{1-8}$alkoxy, amino, $C_{1-6}$alkylamino, di($C_{1-6}$alkyl)amino, cyano, nitro, $C_{1-6}$alkylcarbonyl, sulfonylamino or $C_{1-6}$alkylsulfonylamino;

$R^5$ is, for example, $-Q-R^8$,

Q is selected from methylidene ($-CH_2-$) unsubstituted or substituted with 1-2 substituents, or ethylidene unsubstituted or substituted with 1-3 substituents, $R^8$ is selected from phenyl, 5-7-membered heteromonocyclic group, or 6-14-membered fused ring group, each of which is unsubstituted or substituted with 1-3 substituents, the substituents are selected from $C_{1-3}$alkyl, fluorine, chlorine, methoxy, ethoxy, trifluoromethoxy, dimethylamino or carboxymethyl;

$R^5$ is, for example, $-Q-R^8$,

Q is selected from methylidene ($-CH_2-$) or ethylidene ($-CH_2CH_2-$) unsubstituted or substituted with 1-2 substituents, R[8] is selected from phenyl, 5-7-membered heteromonocyclic group, or 8-10-membered fused ring group, each of which is unsubstituted or substituted with 1-3 substituents, the substituents are selected from $C_{1-3}$alkyl, fluorine, chlorine, methoxy, ethoxy, trifluoromethoxy, dimethylamino or carboxymethyl;

R[5] is, for example, one of a group consisting of:

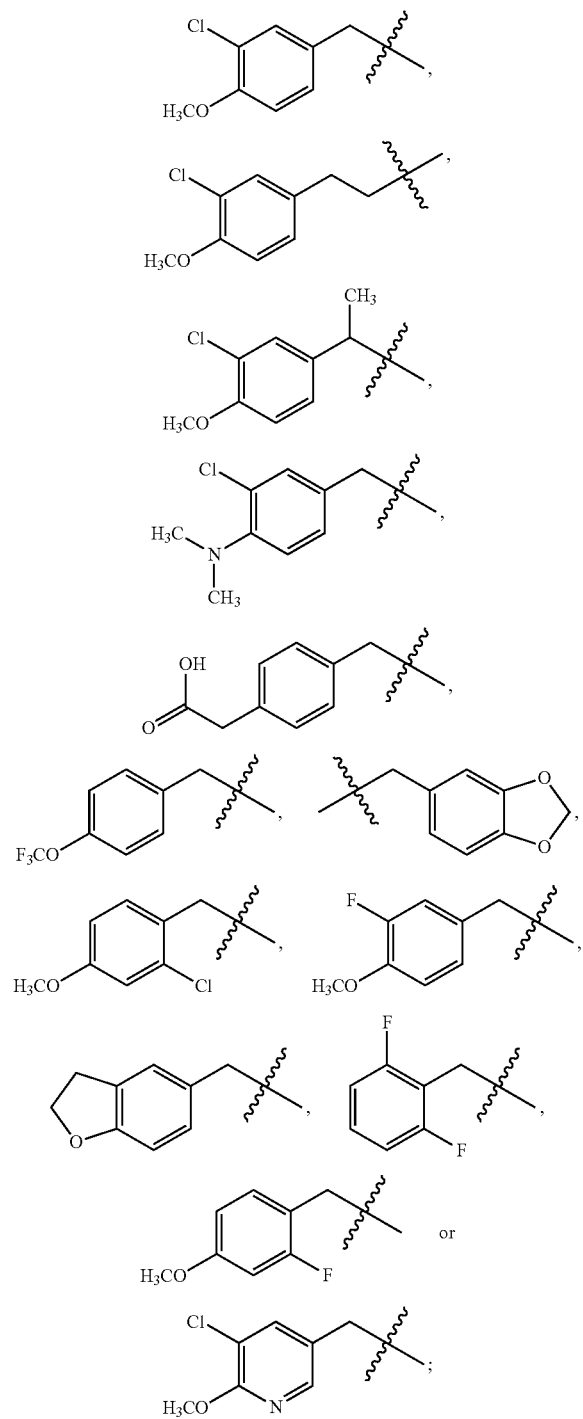

R[5] is, for example, one of a group consisting of:

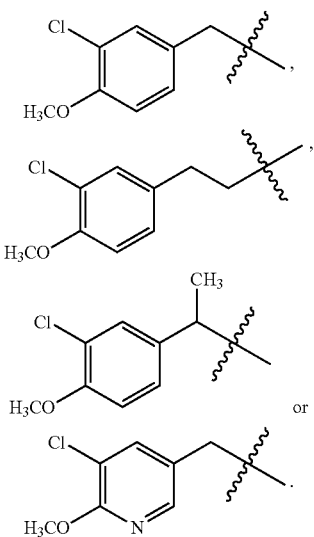

R[5] is, for example, one of a group consisting of:

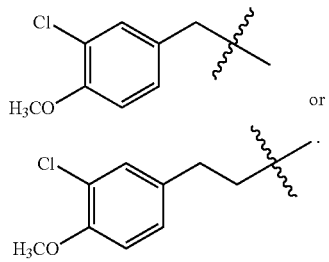

The compound according to the present invention is, for example, a compound of Formula (I), wherein R[1] represents 6-7-membered nitrogen-containing hetero fused ring group, 7-12-membered nitrogen-containing hetero spiro ring group, or 7-12-membered nitrogen-containing hetero bridged ring group, each of which is linked to pyrimidine ring via N and is unsubstituted or substituted with 1-4 substituents, the substituents are selected from halogen atoms, cyano, amino, hydroxy, $C_{1-6}$alkyl, halo$C_{1-6}$alkyl, hydroxy$C_{1-6}$alkyl, $C_{1-6}$alkoxy, $C_{1-6}$alkylcarbonyl or $C_{1-6}$alkoxycarbonyl;

R[2] represents hydrogen atom, hydroxy or methyl;

R[3] represents hydrogen atom or -M-R[7],

M represents a single bond, or $C_{1-6}$alkylidene ($-(CH_2)_t-$ (t is an integer from 1 to 6)) unsubstituted or substituted with 1-4 substituents, R[7] represents a cyclic group other than adamantyl, which is unsubstituted or substituted with 1-4 substituents, or R[3] and R[4] together with the nitrogen atom to which they link form a 5-7-membered nitrogen-containing hetero ring group unsubstituted or substituted with 1-4 substituents, the substituents are selected from halogen atoms, hydroxy, cyano, amino, $C_{1-6}$alkylamino, di($C_{1-6}$alkyl)amino, oxo, $C_{1-6}$alkyl, hydroxy$C_{1-6}$alkyl, halo $C_{1-6}$alkyl, $C_{1-6}$alkoxy, $C_{1-6}$alkylcarbonyl, $C_{1-6}$alkylsulfonyl or di($C_{1-6}$alkyl)phosphino;

R[4] represents hydrogen atom;

R[5] represents hydrogen atom or -Q-R[8],

Q represents a single bond, or $C_{1-6}$alkylidene (—$(CH_2)_t$— ($t$ is an integer from 1 to 6)) unsubstituted or substituted with 1-4 substituents, $R^8$ represents 6-14-membered aryl, 5-7-membered heteromonocyclic group or 6-14-membered fused ring group, each of which is unsubstituted or substituted with 1-4 substituents, the substituents are selected from halogen atoms, hydroxy, $C_{1-6}$alkyl, halo$C_{1-6}$alkyl, carboxyl$C_{1-6}$alkyl, $C_{2-6}$alkenyl, $C_{2-6}$alkynyl, $C_{1-8}$alkoxy, halo$C_{1-8}$ alkoxy, amino, $C_{1-6}$alkylamino, di($C_{1-6}$alkyl)amino, cyano, nitro, $C_{1-6}$alkylcarbonyl, sulfonylamino or $C_{1-6}$alkylsulfonylamino.

The compound according to the present invention is, for example, a compound of Formula (I), wherein $R^1$ represents 6-7-membered nitrogen-containing hetero fused ring group, 7-12-membered nitrogen-containing hetero spiro ring group, or 7-12-membered nitrogen-containing hetero bridged ring group, each of which is linked to pyrimidine ring via N and is unsubstituted or substituted with 1-4 substituents, the substituents are selected from halogen atoms, cyano, amino, hydroxy, $C_{1-6}$alkyl, halo$C_{1-6}$alkyl, hydroxy$C_{1-6}$alkyl, $C_{1-6}$alkoxy, $C_{1-6}$alkylcarbonyl or $C_{1-6}$alkoxycarbonyl;

$R^2$ represents hydrogen atom, hydroxy or methyl;

$R^3$ represents hydrogen atom or -M-$R^7$,

M represents a single bond, or $C_{1-6}$alkylidene (—$(CH_2)_t$— ($t$ is an integer from 1 to 6)) unsubstituted or substituted with 1-4 substituents, $R^7$ represents a cyclic group other than adamantyl, which is unsubstituted or substituted with 1-4 substituents, or $R^3$ and $R^4$ together with the nitrogen atom to which they link form a 5-7-membered nitrogen-containing hetero ring group unsubstituted or substituted with 1-4 substituents, the substituents are selected from halogen atoms, hydroxy, cyano, amino, $C_{1-6}$alkylamino, di($C_{1-6}$alkyl)amino, oxo, $C_{1-6}$alkyl, hydroxy$C_{1-6}$alkyl, halo $C_{1-6}$ alkyl, $C_{1-6}$alkoxy, $C_{1-6}$alkylcarbonyl, $C_{1-6}$alkylsulfonyl or di($C_{1-6}$alkyl)phosphino;

$R^4$ represents hydrogen atom;

$R^5$ represents -Q-$R^8$,

Q is selected from a $C_{1-6}$alkylidene (—$(CH_2)_t$— ($t$ is an integer from 1 to 6)) unsubstituted or substituted with 1-3 substituents, $R^8$ is selected from 6-14-membered aryl, 5-7-membered heteromonocyclic group or 6-14-membered fused ring group, each of which is unsubstituted or substituted with 1-3 substituents, the substituents are selected from halogen atoms, hydroxy, $C_{1-6}$alkyl, halo$C_{1-6}$alkyl, carboxyl$C_{1-6}$alkyl, $C_{1-8}$alkoxy, halo$C_{1-8}$alkoxy, amino, $C_{1-6}$alkylamino, di($C_{1-6}$alkyl)amino, cyano, nitro, $C_{1-6}$alkylcarbonyl, sulfonylamino or $C_{1-6}$alkylsulfonylamino.

The compound according to the present invention is, for example, a compound of Formula (I), wherein $R^1$ is selected from 6-7-membered nitrogen-containing hetero fused ring group, 7-10-membered nitrogen-containing hetero spiro ring group, or 7-8-membered nitrogen-containing hetero bridged ring group, each of which is linked to pyrimidine ring via N and is unsubstituted or substituted with 1-3 substituents, the substituents are selected from halogen atoms, cyano, amino, hydroxy, $C_{1-6}$alkyl, halo$C_{1-6}$alkyl, hydroxy$C_{1-6}$ alkyl or $C_{1-6}$alkoxy;

$R^2$ represents hydrogen atom, hydroxy or methyl;

$R^3$ is selected from -M-$R^7$,

M represents a single bond or $C_{1-6}$alkylidene unsubstituted or substituted with 1-4 substituents, $R^7$ is selected from phenyl, 5-7-membered heteromonocyclic group, 4-7-membered cycloalkyl, 6-14-membered fused ring group, 7-10-membered spiro ring group, or 7-10-membered bridged ring group other than adamantyl, each of which is unsubstituted or substituted with 1-3 substituents, or $R^3$ and $R^4$ together with the nitrogen atom to which they link form a 5-6-membered nitrogen-containing hetero ring group, which is unsubstituted or substituted, the substituents are selected from halogen atoms, hydroxy, cyano, amino, $C_{1-6}$alkylamino, di($C_{1-6}$ alkyl)amino, oxo, $C_{1-6}$alkyl, hydroxy $C_{1-6}$alkyl, halo$C_{1-6}$alkyl or $C_{1-6}$alkoxy;

$R^4$ represents hydrogen atom;

$R^5$ represents -Q-$R^8$,

Q is selected from methylidene(—$CH_2$—) unsubstituted or substituted with 1-2 substituents, or ethylidene unsubstituted or substituted with 1-3 substituents, $R^8$ is selected from phenyl, 5-7-membered heteromonocyclic group, or 6-14-membered fused ring group, each of which is unsubstituted or substituted with 1-3 substituents, the substituents are selected from $C_{1-3}$alkyl, fluorine, chlorine, methoxy, ethoxy, trifluoromethoxy, dimethylamino or carboxymethyl.

The compound according to the present invention is, for example, a compound of Formula (I), wherein $R^1$ is selected from 6-7-membered nitrogen-containing hetero fused ring group, 7-10-membered nitrogen-containing hetero spiro ring group, or 7-8-membered nitrogen-containing hetero bridged ring group, each of which is linked to pyrimidine ring via N and is unsubstituted or substituted with 1-3 substituents, the substituents are selected from halogen atoms, cyano, amino, hydroxy, $C_{1-6}$alkyl, halo$C_{1-6}$alkyl, hydroxy$C_{1-6}$ alkyl or $C_{1-6}$alkoxy;

$R^2$ represents hydrogen atom, hydroxy or methyl;

$R^3$ is selected from -M-$R^7$,

M represents a single bond or $C_{1-6}$alkylidene unsubstituted or substituted with 1-2 substituents, $R^7$ is selected from phenyl, 5-7-membered heteromonocyclic group, 4-7-membered cycloalkyl, 8-10-membered fused ring group, or 7-10-membered spiro ring group, each of which is unsubstituted or substituted with 1-3 substituents, or $R^3$ and $R^4$ together with the nitrogen atom to which they link form a 5-6-membered nitrogen-containing hetero ring group, which is unsubstituted or substituted, the substituents are selected from halogen atoms, hydroxy, cyano, amino, $C_{1-6}$alkylamino, di($C_{1-6}$ alkyl)amino, oxo, $C_{1-6}$alkyl, hydroxy$C_{1-6}$alkyl, halo$C_{1-6}$alkyl or $C_{1-6}$alkoxy;

$R^4$ represents hydrogen atom;

$R^5$ represents -Q-$R^8$,

Q is selected from methylidene (—$CH_2$—) or ethylidene (—$CH_2CH_2$—) unsubstituted or substituted with 1-2 substituents, $R^8$ is selected from phenyl, 5-7-membered heteromonocyclic group, or 8-10-membered fused ring group, each of which is unsubstituted or substituted with 1-3 substituents, the substituents are selected from $C_{1-3}$alkyl, fluorine, chlorine, methoxy, ethoxy, trifluoromethoxy, dimethylamino or carboxymethyl.

The compound according to the present invention is, for example, a compound of Formula (I), wherein $R^1$ is selected from a group consisting of:
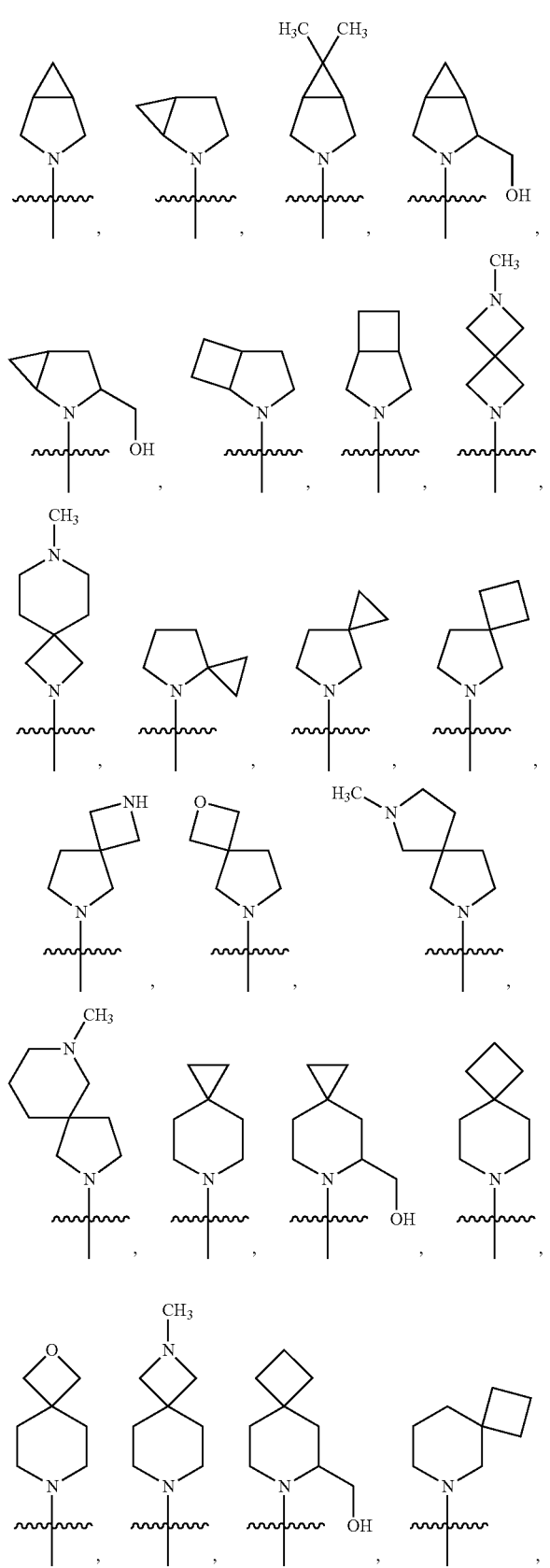
$R^2$ is selected from hydrogen atom;
$R^4$ is selected from hydrogen atom;
$R^3$ is selected from a group consisting of:
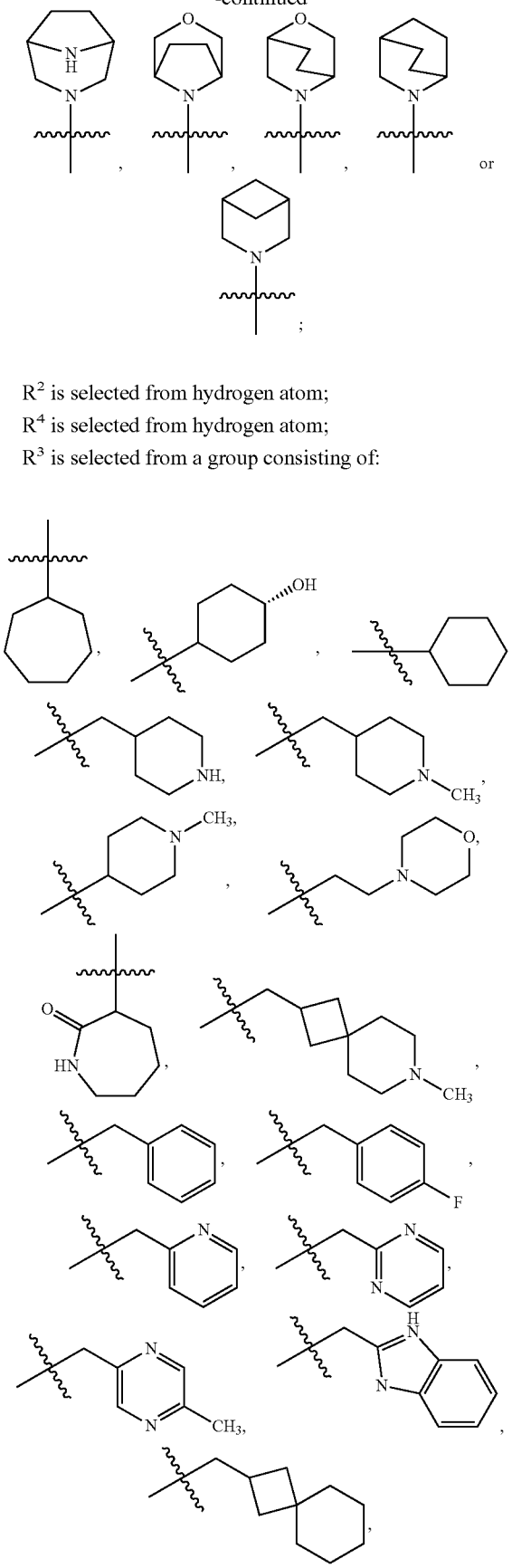

-continued
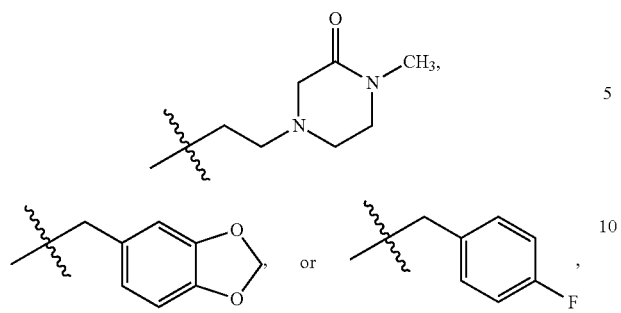
or R³ and R⁴ together with the nitrogen atom to which they link form:
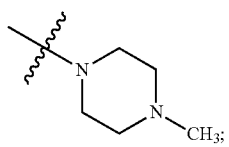 [SMILES: *N1CCN(C)CC1]
R⁵ is selected from a group consisting of:
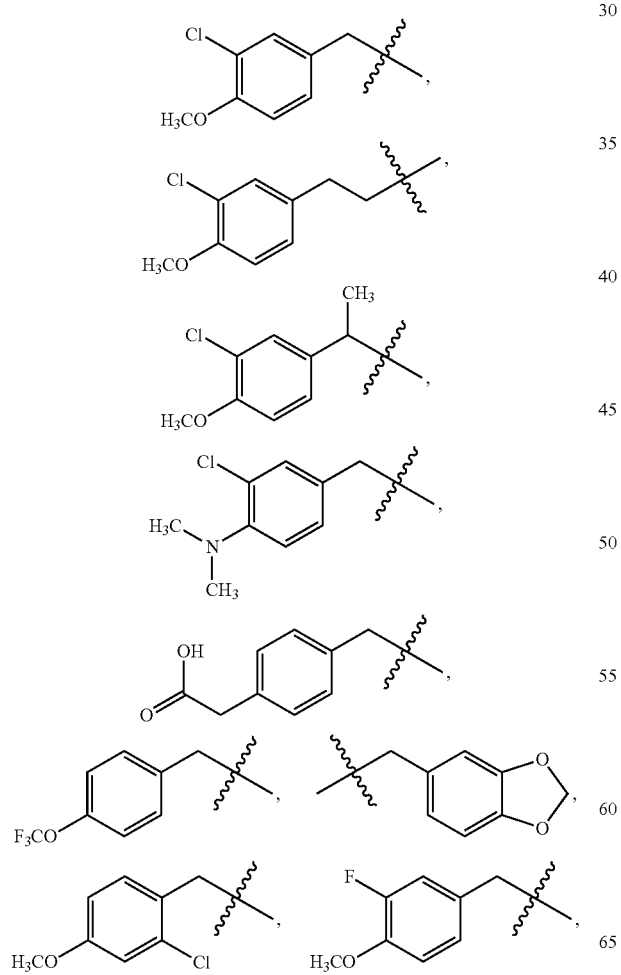
-continued
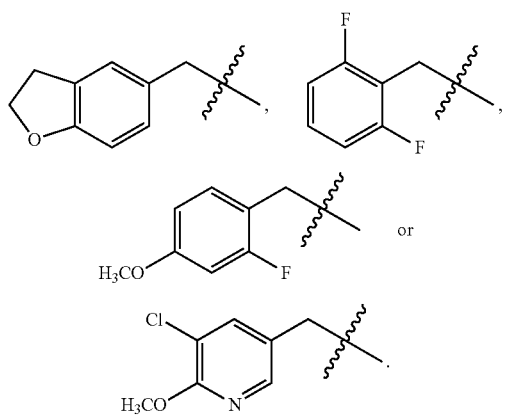
The compound according to the present invention is, for example, a compound of Formula (I),
wherein
R¹ is selected from a group consisting of:
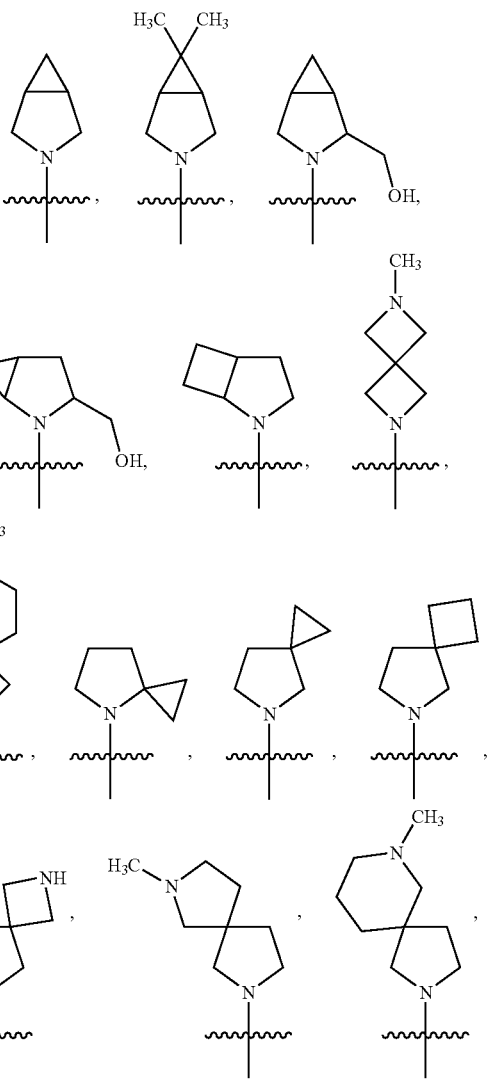

-continued
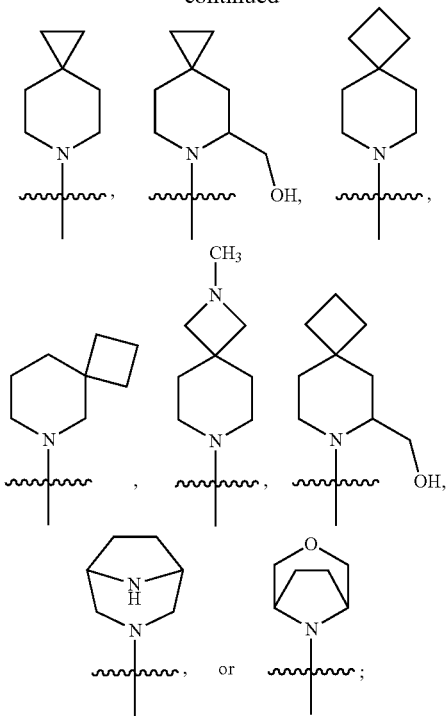
R² is selected from hydrogen atom;
R³ is selected from a group consisting of:
-continued
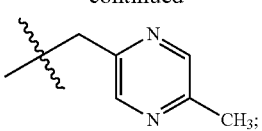
R⁴ is selected from hydrogen atom;
R⁵ is selected from a group consisting of:
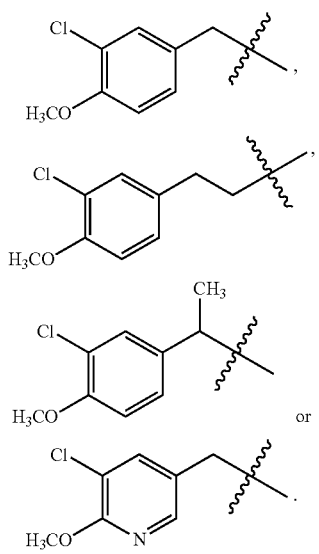
The compound according to the present invention is, for example, a compound of Formula (I), wherein
R¹ is selected from a group consisting of:
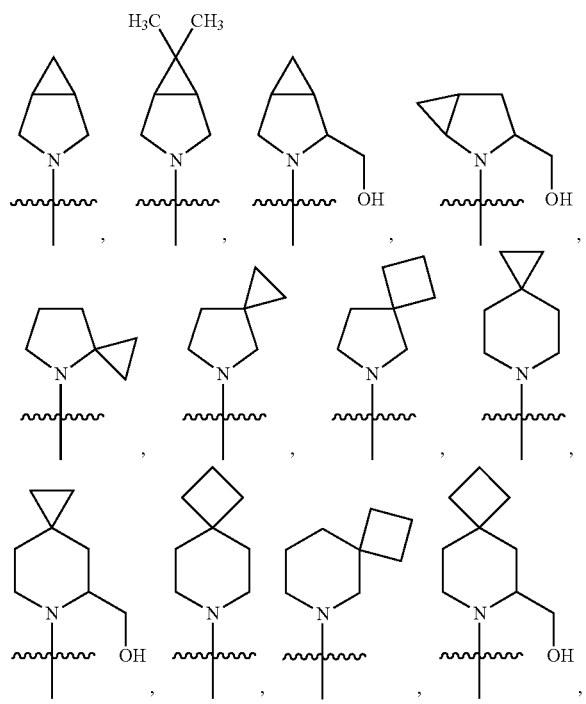

-continued

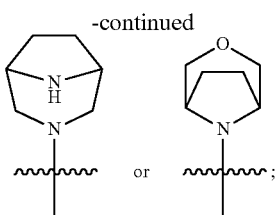

$R^2$ is selected from hydrogen atom;
$R^3$ is selected from a group consisting of:

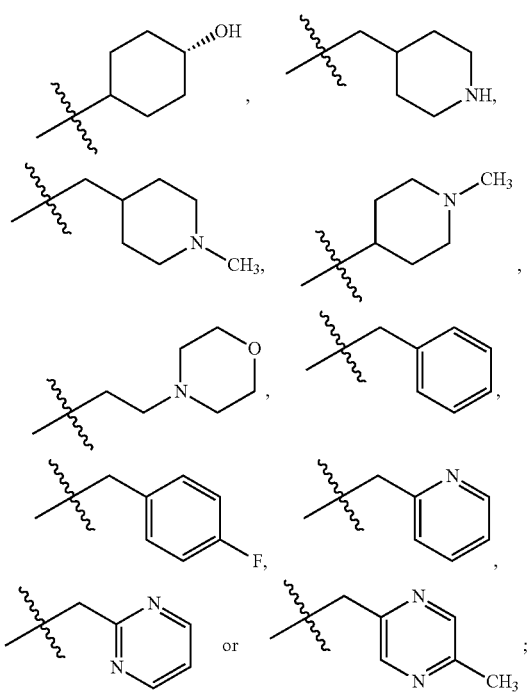

$R^4$ is selected from hydrogen atom;
$R^5$ is selected from a group consisting of:

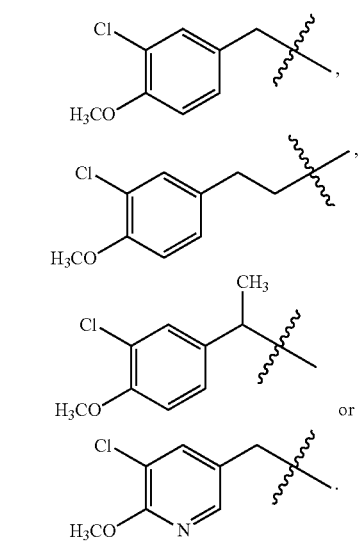

The compound according to the present invention is, for example, a compound of Formula (I),
wherein $R^1$ is selected from a group consisting of:

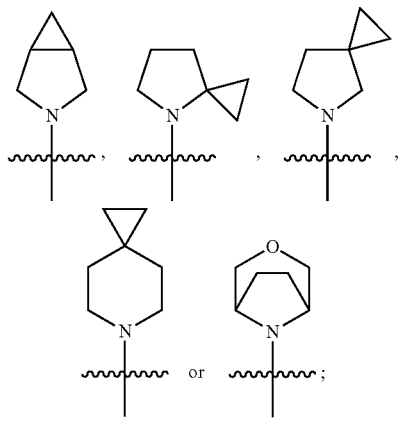

$R^2$ is selected from hydrogen atom;
$R^3$ is selected from a group consisting of:

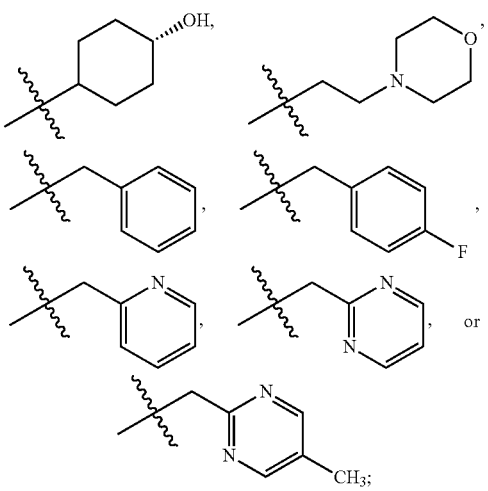

$R^4$ is selected from hydrogen atom;
$R^5$ is selected from a group consisting of:

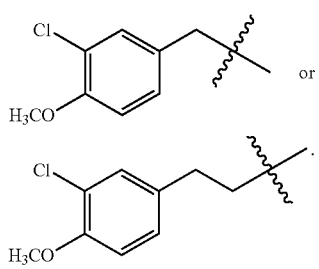

In the present invention, the term "halo" substituted refers to being substituted with a "halogen atom", "halogen atom" refers to fluorine atom, chlorine atom, bromine atom, iodine atom.
In the present invention, the term "$C_{1-6}$alkyl" refers to straight or branched alkyl containing 1-6 atoms, such as methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1, -dimethylbutyl, 2,3-dimethylbutyl, 2-ethylbutyl, 1,2-dimethylpropyl. For example, $C_{1-3}$alkyl. In the present invention, the term "$C_{1-3}$alkyl" refers to the above examples containing 1-3 carbon atoms.

In the present invention, the term "$C_{1-6}$alkylidene" refers to a straight or branched alkane derived from the above alkyl by removing one hydrogen atom, including —$(CH_2)_t$— (t is an integer from 1 to 6), for example, methylidene(—$CH_2$—), ethylidene (—$CH_2CH_2$—), propylidene (—$CH_2CH_2CH_2$—) etc.

In the present invention, the term "$C_{1-6}$alkoxy" refers to a group in which "$C_{1-6}$alkyl" links to another structure via oxygen atom, for example, methoxy, ethoxy, propoxy, iso-propoxy, butoxy, iso-butoxy, tert-butoxy, sec-butoxy, pentyloxy, neo-pentyloxy, hexoxy etc.

In the present invention, $R^1$ represents 6-7-membered nitrogen-containing hetero fused ring group, 7-12-membered nitrogen-containing hetero spiro ring group, or 7-12-membered nitrogen-containing hetero bridged ring group, "6-7-membered nitrogen-containing hetero fused ring group" refers to 6-7-membered saturated or partially saturated nitrogen-containing fused ring group which contains 6-7 ring atoms (which contains at least one nitrogen atom, and may also contain other hetero atoms) and constitutes of two or more cyclic structures sharing and linking by two adjacent atoms between each other, specific example including but not being limited to groups formed by substituting any substitutable hydrogen atom with cyclic structures such as

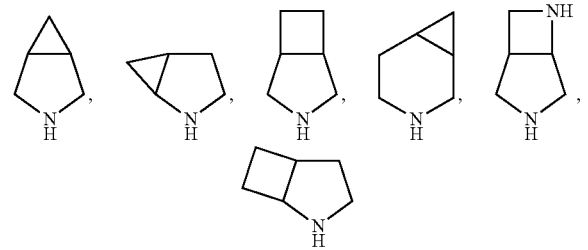

etc.

The term "7-12-membered nitrogen-containing hetero Spiro ring group" refers to a Spiro ring structure containing 7-12 ring atoms (which contains at least one nitrogen atom, and may also contain other hetero atoms) in which at least two rings share one atom, comprising saturated 7-12-membered nitrogen-containing spiro ring groups and partially saturated 7-12-membered nitrogen-containing hetero spiro ring groups.

Saturated 7-12-membered nitrogen-containing hetero spiro ring group refers to a spiro ring group in which all rings of the spiro ring are saturated cyclic groups, examples thereof including but not being limited to: groups formed by substituting any substitutable hydrogen atom with cyclic structures such as

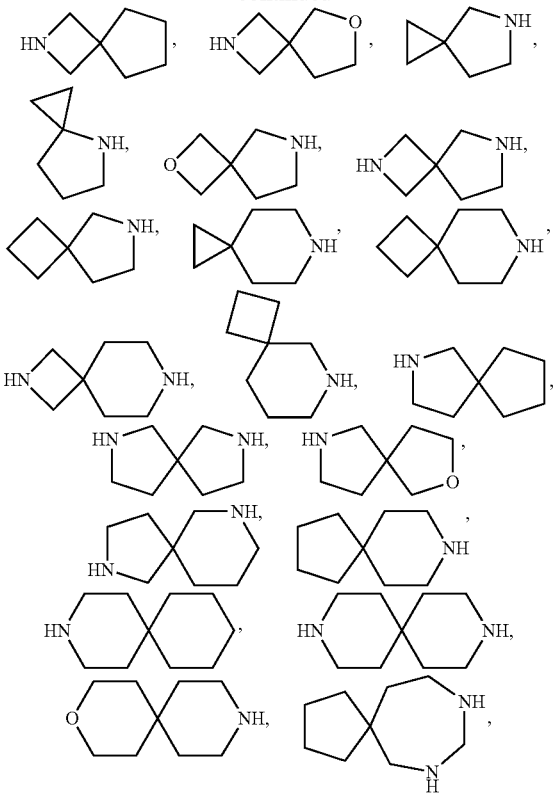

etc., for example, saturated 7-10-membered nitrogen-containing hetero spiro ring groups.

Partially saturated 7-12-membered nitrogen-containing hetero spiro ring group refers to a spiro ring group in which at least one ring of the spiro ring is an unsaturated cyclic group, examples thereof including but not being limited to: groups formed by substituting any substitutable hydrogen atom with cyclic structures such as:

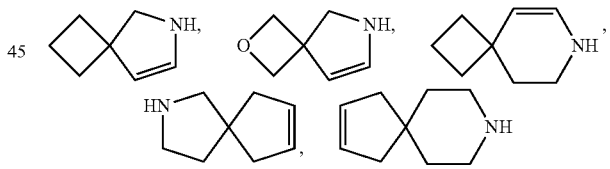

etc., for example, partially saturated 7-10-membered nitrogen-containing hetero spiro ring groups.

The "7-12-membered nitrogen-containing hetero bridged ring group" refers to a cyclic structure containing 7-12 ring atoms (which contains at least one nitrogen atom, and may also contain other hetero atoms), in which two rings share two atoms that are not directly linked together, including 7-12-membered saturated bridged rings, 7-12-membered partially saturated bridged rings.

Saturated 7-12-membered nitrogen-containing hetero bridged ring group refers to that all rings in the bridged ring are saturated cyclic ring groups, for example, saturated 7-8-membered nitrogen-containing hetero bridged ring groups, specific examples including but not being limited to: groups formed by substituting any substitutable hydrogen atom with cyclic structures such as:

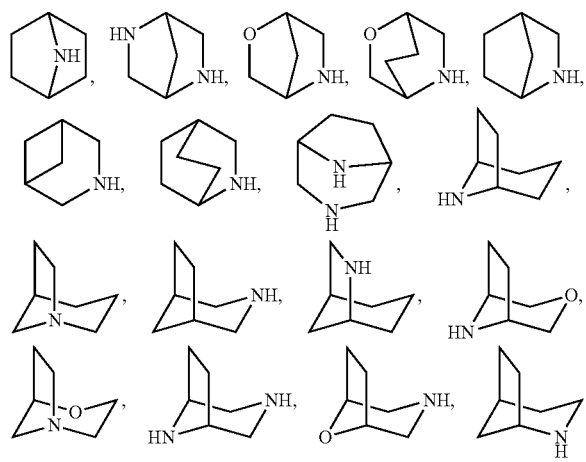

etc.

Partially saturated 7-12-membered nitrogen-containing bridged ring group refers to that at least one ring in the bridged ring is unsaturated cyclic ring group, for example, 7-8-membered partially unsaturated bridged ring, specific examples including but not limited to: groups formed by substituting any substitutable hydrogen atom with cyclic structures such as:

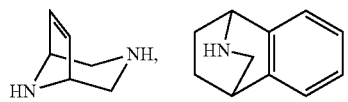 [SMILES: C1=CC2CNCC1N2 ; c1ccc2c(c1)C1CCC2NC1]

etc.

In the present invention, $R^7$ represents a "cyclic group", including phenyl, 5-7-membered heteromonocyclic group, 4-7-membered cycloalkyl, 6-14-membered fused ring group, 7-10-membered spiro ring group, or 7-10-membered bridged ring group, "5-7-membered heteromonocyclic group" includes saturated, partially saturated and unsaturated nitrogen-containing 5-7-membered cyclic group containing hetero atom, in which the hetero atom is nitrogen, oxygen or sulfur etc.

The specific examples of "saturated 5-7-membered heteromonocyclic group" include but are not limited to: tetrahydrofuryl, tetrahydrothienyl, tetrahydropyrrolyl, imidazolidinyl, pyrazolidinyl, piperidyl, morpholinyl, piperazinyl, 2-oxo-azacycloheptyl, 2-oxo-piperazinyl etc.

The specific examples of "partially saturated 5-7-membered heteromonocyclic group" include but are not limited to: dihydrothienyl, dihydropyrrolyl, dihydrooxazolyl, dihydropyrazolyl etc.

The specific examples of "unsaturated 5-7-membered heteromonocyclic group" include but are not limited to: furyl, thienyl, pyrrolyl, imidazolyl, pyrazolyl, thiazolyl, oxazolyl, pyrimidyl, pyridyl, pyrazinyl etc.

The term "4-7-membered cycloalkyl" refers to 4-7-membered monocycloalkyl, examples including but not being limited to: cyclobutyl, cyclopentyl, cyclohexyl, cycloheptyl etc.

The term "6-14-membered fused ring group" refers to a fused ring structure containing 6-14 atoms in which two or more cyclic structures share two adjacent atoms, including: 6-14-membered saturated fused ring groups, 6-14-membered partially saturated fused ring groups, 6-14-membered unsaturated fused hetero ring groups, 6-14-membered partially saturated fused hetero ring groups, 6-14-membered saturated fused hetero ring groups. For examples, 8-10-membered fused ring groups. The 6-14-membered saturated fused ring group refers to that the fused ring group is a fully saturated carbon ring, which examples include but are not limited to: dicyclo[3.1.0]hexyl, dicyclo[4.1.0]heptyl, dicyclo[2.2.0]hexyl, dicyclo[3.2.0]heptyl, dicyclo[4.2.0]octyl, octahydrocyclopentadienyl, octahydro-1H-indenyl, decahydro naphthalenyl, tetradecahydro phenanthryl. The 6-14-membered partially saturated fused ring group refers to that at least one ring in the fused ring is partially saturated carbon ring, which examples include but are not limited to: dicyclo[3.1.0]hexan-2-enyl, dicyclo[4.1.0]heptan-3-enyl, dicyclo[3.2.0]heptan-3-enyl, dicyclo[4.2.0]octan-3-enyl, 1,2,3,3a-tetrahydrocyclopentadienyl, 2,3,3a,4,7,7a-hexahydro-1H-indenyl, 1,2,3,4,4a,5,6,8a-octahydronaphthalenyl, 1,2,4a,5,6,8a-hexahydronaphthalenyl, 1,2,3,4,5,6,7,8,9,10-octahydronaphthalenyl. The 6-14-membered unsaturated fused hetero ring group refers to that all rings of the fused ring are unsaturated rings, for example, structures such as those formed by fusing phenyl with 3-8-membered unsaturated heteromonocyclic group, fusing 3-8-membered unsaturated heteromonocyclic group with 3-8-membered unsaturated heteromonocyclic group, which specific examples include but are not limited to: benzofuryl, benzoisofuryl, benzothienyl, indolyl, benzoxazolyl, benzimidazolyl, indazolyl, benzotriazolyl, quinolyl, isoquinolyl, acridinyl, phenanthridinyl, benzopyridazinyl, phthalazinyl, quinazolinyl, quinoxalinyl, phenazinyl, pteridinyl, purinyl, naphthyridinyl, or groups formed by substituting any substitutable hydrogen atom with cyclic structures such as

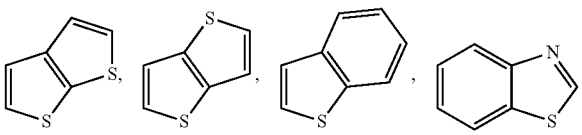

etc. The 6-14-membered partially saturated fused hetero ring group refers to a fused ring structure containing at least one partially saturated ring, for example, a structure formed by fusing phenyl with 3-8-membered partially saturated heteromonocyclic group, a structure formed by fusing 3-8-membered partially saturated heteromonocyclic group with 3-8-membered partially saturated heteromonocyclic group, which specific examples include but are not limited to: 1,3-dihydrobenzofuryl, benzo[d][1.3]dioxolyl, isoindolinyl, chromanyl, 1,2,3,4-tetrahydropyrrolo[3,4-c]pyrrolyl or groups formed by substituting any substitutable hydrogen atom with cyclic structures such as

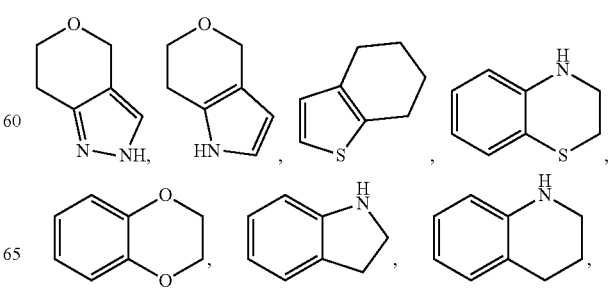

etc. The 6-14-membered saturated fused hetero ring group refers to that all rings in the fused ring are saturated rings, for example, a structure formed by fusing 3-8-membered saturated heteromonocyclic group with 3-8-membered saturated heteromonocyclic group, which specific examples include but are not limited to: cyclobutanotetrahydropyrrolyl, cyclopentanotetrahydropyrrolyl, azacyclobutanoimidazolidinyl, or groups formed by substituting any substitutable hydrogen atom with cyclic structures such as etc.

The "8-10-membered fused ring group" refers to the above fused ring structure containing 8-10 atoms, which specific examples include but are not limited to: groups formed by substituting any substitutable hydrogen atom with cyclic structures such as etc.

The "7-10-membered spiro ring group" refers to a spiro ring structure in which at least two rings share one atom to form a spiro ring structure containing 7-10 ring atoms (which may comprise hetero atoms), which specific examples include but are not limited to: groups formed by substituting any substitutable hydrogen atom with cyclic structures such as etc.

The "7-10-membered bridged ring group" refers to a cyclic structure in which any two rings share two atoms that are not directly linked to form a cyclic structure containing 7-10 ring atoms (which may comprise hetero atoms), which specific examples include but are not limited to: groups formed by substituting any substitutable hydrogen atom with cyclic structures such as etc., but do not include adamantly.

In the present invention, $R^3$ and $R^4$ together with the nitrogen atom to which they link form substituted or unsubstituted "5-7-membered nitrogen-containing hetero ring group", including saturated, partially saturated and unsaturated 5-7-membered nitrogen-containing hetero ring group.

The specific examples of "saturated 5-7-membered nitrogen-containing hetero ring group" include but are not limited to: pyrrolidinyl, imidazolidinyl, pyrazolidinyl, piperidyl, piperazinyl, morpholinyl; the specific examples of "partially saturated 5-7-membered nitrogen-containing hetero ring group" include but are not limited to: dihydropyrrolyl, dihydropyrazolyl, dihydroxazinyl; the specific examples of "unsaturated 5-7-membered nitrogen-containing hetero ring group" include but are not limited to: pyrrolyl, imidazolyl, pyrazolyl.

In the present invention, $R^8$ represents "6-14-membered aryl", "5-7-membered heteromonocyclic group" or "6-14-membered fused ring group", Wherein "6-14-membered aryl" refers to cyclic aromatic group in which all ring atoms are carbon atoms, for example, phenyl, naphthyl etc;

Wherein "5-7-membered heteromonocyclic group" refers to 5-7-membered saturated, partially saturated or unsaturated structure containing hetero atom such as nitrogen, oxygen and sulfur etc.

The specific examples of "saturated 5-7-membered heteromonocyclic group" include but are not limited to: pyrrolidinyl, imidazolidinyl, pyrazolidinyl, piperidyl, piperazinyl, morpholinyl, azacycloheptyl; the specific examples of "partially saturated 5-7-membered heteromonocyclic group" include but are not limited to: dihydropyrrolyl, dihydropyrazolyl, dihydroxazinyl; the specific examples of "unsaturated 5-7-membered heteromonocyclic group" include but are not limited to: pyrrolyl, imidazolyl, pyrazolyl, pyridyl, pyrazinyl, azepinyl etc;

wherein the "6-14-membered fused ring group" is defined as above.

In the present invention, the term "oxo" refers to

In the present invention, the hetero ring group refers to a cyclic group containing one or more hetero atoms, in which the examples of "hetero atoms" include but are not limited to: N, S, O, SO or $SO_2$.

The compounds of the present invention include:

| Compound | Chemical Name | Structural Formula |
| --- | --- | --- |
| 1 | N-benzyl-2-(3-azadicyclo[3.1.0]hexan-3-yl)-4-(3-chloro-4-methoxybenzyloxy)pyrimidine-5-carboxamide | |
| 2 | N-benzyl-2-(3-oxa-8-azadicyclo[3.2.1]octan-8-yl)-4-(3-chloro-4-methoxybenzyloxy)pyrimidine-5-carboxamide | |

-continued

| Compound | Chemical Name | Structural Formula |
|---|---|---|
| 3 | 2-(3-azadicyclo[3.1.0]hexan-3-yl)-4-(3-chloro-4-methoxybenzyloxy)-N-(pyrimidin-2-ylmethyl)pyrimidine-5-carboxamide | |
| 4 | 2-(3-azadicyclo[3.1.0]hexan-3-yl)-4-(3-chloro-4-methoxybenzyloxy)-N-(pyridin-2-ylmethyl)pyrimidine-5-carboxamide | |
| 5 | 2-(3-azadicyclo[3.1.0]hexan-3-yl)-4-(3-chloro-4-methoxybenzyloxy)-N-[(5-methylpyrazin-2-yl)methyl]pyrimidine-5-carboxamide | |
| 6 | 2-(3-azadicyclo[3.1.0]hexan-3-yl)-4-(3-chloro-4-methoxybenzyloxy)-N-(4-fluorobenzyl)pyrimidine-5-carboxamide | |

-continued

| Compound | Chemical Name | Structural Formula |
|---|---|---|
| 7 | 2-(3-azadicyclo[3.1.0]hexan-3-yl)-4-(3-chloro-4-methoxybenzyloxy)-N-((trans)-4-hydroxycyclohexyl)pyrimidine-5-carboxamide | |
| 8 | 4-(3-chloro-4-methoxybenzyloxy)-N-(pyrimidin-2-ylmethyl)-2-(6-azaspiro[2.5]octan-6-yl)pyrimidine-5-carboxamide | |
| 9 | 4-(3-chloro-4-methoxybenzyloxy)-N-(pyridin-2-ylmethyl)-2-(6-azaspiro[2.5]octan-6-yl)pyrimidine-5-carboxamide | |
| 10 | N-benzyl-4-(3-chloro-4-methoxybenzyloxy)-2-(6-azaspiro[2.5]octan-6-yl)pyrimidine-5-carboxamide | |

| Compound | Chemical Name | Structural Formula |
|---|---|---|
| 11 | 4-(3-chloro-4-methoxybenzyloxy)-N-(2-morpholinylethyl)-2-(6-azaspiro[2.5]octan-6-yl)pyrimidine-5-carboxamide | 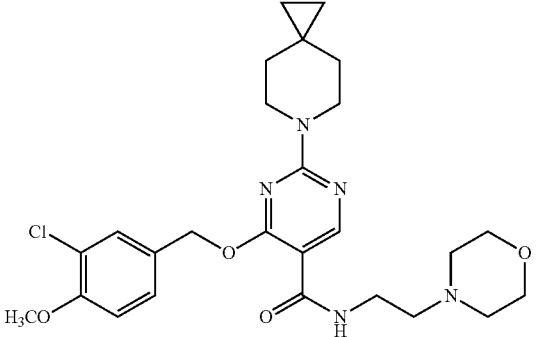 [SMILES: COc1ccc(COc2nc(N3CCC4(CC3)CC4)ncc2C(=O)NCCN2CCOCC2)cc1Cl] |
| 12 | 4-(3-chloro-4-methoxybenzyloxy)-N-((trans)-4-hydroxycyclohexyl)-2-(6-azaspiro[2.5]octan-6-yl)pyrimidine-5-carboxamide | 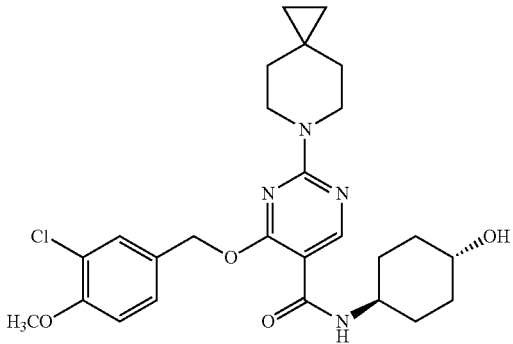 [SMILES: COc1ccc(COc2nc(N3CCC4(CC3)CC4)ncc2C(=O)N[C@H]2CC[C@H](O)CC2)cc1Cl] |
| 13 | 2-(3-azadicyclo[3.1.0]hexan-3-yl)-4-(3-chloro-4-methoxybenzyloxy)-N-(2-morpholinylethyl)pyrimidine-5-carboxamide | 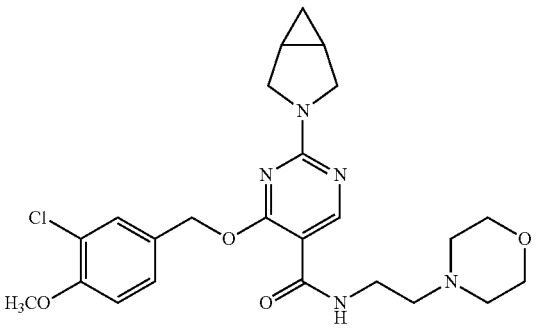 [SMILES: COc1ccc(COc2nc(N3CC4CC4C3)ncc2C(=O)NCCN2CCOCC2)cc1Cl] |
| 14 | N-benzyl-4-(3-chloro-4-methoxybenzyloxy)-2-(4-azaspiro[2.4]heptan-4-yl)pyrimidine-5-carboxamide | 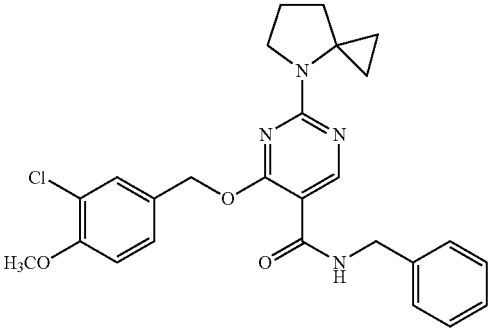 [SMILES: COc1ccc(COc2nc(N3CCCC34CC4)ncc2C(=O)NCc2ccccc2)cc1Cl] |

| Compound | Chemical Name | Structural Formula |
|---|---|---|
| 15 | N-benzyl-4-(3-chloro-4-methoxybenzyloxy)-2-(5-azaspiro[2.4]heptan-4-yl)pyrimidine-5-carboxamide | |
| 16 | 2-(3-azadicyclo[3.1.0]hexan-3-yl)-4-(3-chloro-4-methoxyphenylethoxy)-N-[(trans)-4-hydroxycyclohexyl]pyrimidine-5-carboxamide | |
| 17 | 4-(3-chloro-4-methoxybenzyloxy)-N-(4-fluorobenzyl)-2-(5-azaspiro[2.4]heptan-5-yl)pyrimidine-5-carboxamide | |
| 18 | 4-(3-chloro-4-methoxybenzyloxy)-N-(pyrimidin-2-ylmethyl)-2-(5-azaspiro[2.4]heptan-5-yl)pyrimidine-5-carboxamide | |

| Compound | Chemical Name | Structural Formula |
|---|---|---|
| 19 | 4-(3-chloro-4-methoxybenzyloxy)-N-[(trans)-4-hydroxycyclohexyl]-2-(5-azaspiro[2.4]heptan-5-yl)-pyrimidine-5-carboxamide | |
| 20 | 4-(3-chloro-4-methoxybenzyloxy)-N-[(trans)-4-hydroxycyclohexyl]-2-(4-azaspiro[2.4]heptan-4-yl)pyrimidine-5-carboxamide | |
| 21 | 4-(3-chloro-4-methoxybenzyloxy)-N-(4-fluorobenzyl)-2-(6-azaspiro[2.5]octan-6-yl)pyrimidine-5-carboxamide | |

The above compounds of the present invention can be synthesized by the methods as shown in the following schemes or other methods known by those skilled in the art, without being limited to the following methods.

For convenience, many chemical compounds are represented with acronyms well-known in the art, including but not being limited to:

THF: tetrahydrofuran; DCM: dichloromethane; DIEA: N,N-diiso-propylethylamine; HATU: 2-(7-azobenzotriaz-olyl)-N,N,N',N'-tetramethylurea hexafluorophosphate; m-CPBA: m-chloro perbenzoic acid.

Reaction schemes:

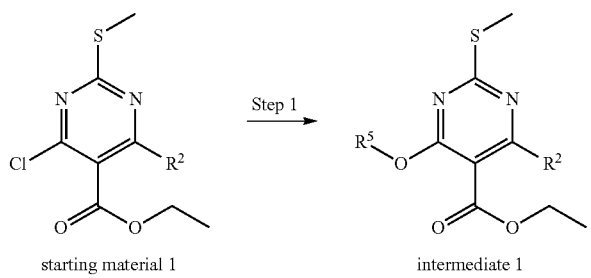

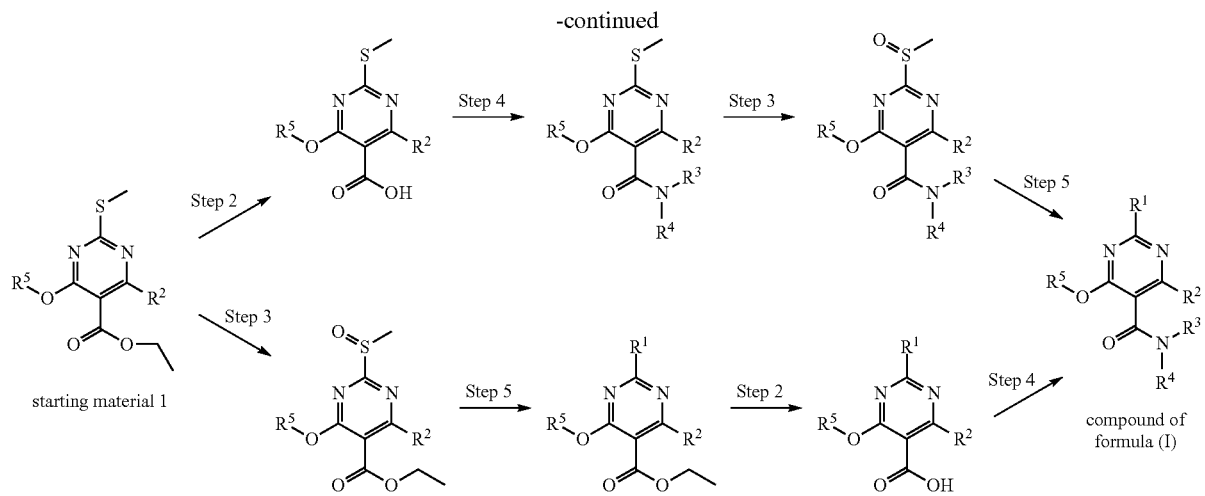

Reaction Steps:

Step 1: dissolving starting material 2 in THF, adding NaH under ice-bath, after 0.5 h of reaction, adding to THF solution of starting material 1, stifling until the reaction is complete, adding water, extracting, drying organic layer, concentrating to obtain intermediate 1.

Step 2: dissolving corresponding intermediate in a mixture of THF and water, adding NaOH, stirring until the reaction is complete, removing solvent, adjusting to acidity, filtering to obtain solid, drying under vacuum to obtain corresponding product.

Step 3: dissolving corresponding intermediate in DCM, adding m-CPBA, after the reaction is complete at room temperature, adding water for quenching, extracting, drying, concentrating to obtain corresponding product.

Step 4: dissolving corresponding intermediate, starting material 3, HATU in DCM or THF, adding DIEA or triethylamine dropwise, stifling at room temperature until the reaction is complete, adding water, extracting, drying, concentrating, subjecting to column chromatography separation to obtain corresponding product.

Step 5: dissolving corresponding intermediate in THF, adding starting material 4, adding DIEA, performing reaction at room temperature or under heating until end of reaction, adding water, extracting, concentrating, separating by column chromatography to obtain product.

Wherein starting material $2=R^5OH$, starting material $3=R^3R^4NH$, starting material $4=R^1H$, and $R^1$, $R^2$, $R^3$, $R^4$ and $R^5$ are defined as above.

Clinically, the compound of Formula (I) of the present invention can be used in free form or in form of pharmaceutically acceptable salt. The compound of Formula (I) of the present invention is an alkaline, which can form acidic salt with inorganic acid or organic acid. In the present invention, the pharmaceutically acceptable salt refers to a salt formed with one or more organic acids or inorganic acids, wherein the organic acids include but are not limited to tartaric acid, citric acid, formic acid, acetic acid, ethanedioic acid, oxalic acid, succinic acid, methylsulfonic acid, ethanesulfonic acid, propanesulfonic acid, fumaric acid, gluconic acid, glutamic acid, lactic acid, malic acid, succinic acid, maleic acid, arginine, benzenesulfonic acid, benzoic acid, p-toluenesulfonic acid, and inorganic acids include but are not limited to hydrochloric acid, sulfuric acid, phosphoric acid, hydrobromic acid and nitric acid.

The compounds of Formula (I) of the present invention or pharmaceutically acceptable salt thereof can exist in optical isomer form due to chiral molecules. Thus, the present invention further comprises these optical isomers and mixture thereof.

When the compounds of Formula (I) of the present invention or pharmaceutically acceptable salt thereof have double bond or small ring structure, free rotation of bond between atoms of the double bond or ring is limited, so that there are stereoisomers with different spatial arrangement manners, which are also called as cis/trans-isomers. Thus, the present invention further comprises cis/trans-isomers and mixtures thereof.

The present invention further comprises stereoisomers and mixtures thereof, which are generated by changing spatial arrangement of atoms or atom groups linked to carbon atom due to rotation of single bond, which are also called as conformational isomers.

The compound of Formula (I) of the present invention, its pharmaceutically acceptable salts or stereoisomers can form a pharmaceutical composition with one or more pharmaceutically acceptable carriers. The "pharmaceutically acceptable carriers" refer to non-toxic inert solids, semi-solids or liquid fillers, diluents, encapsulation materials or any types of additives, such as excipients, binding agent, humidizers, disintegrating agents, thickening agents etc.

The pharmaceutical composition can be processed to form conventional pharmaceutical preparations for clinical uses, and can be administered to patients in need of therapy via common clinical administration routes. The administration routes include intraintestinal administration, parenteral injection and topical administration. Intraintestinal administration comprises: oral administration, sublingual administration (for sublingual tablets, sublingual spray, membranes) and rectal administration (for suppository, enema). Parenteral injection comprises intravenous injection, intramuscular injection, subcutaneous injection. Topical administration comprises topical administration on mucosa, skin and eyes (for membrane, ointment, eye drops).

For oral administration, it can be processed to form conventional solid preparations, such as tablets, capsules, pills, granules; or oral liquid preparations, such as oral solutions, oral suspensions, syrups. When processing oral preparations, suitable filling agents, binding agents, disintegrating agents, or lubricants can be added. Commonly used filling agents include starch, sugar powder, calcium phosphate, calcium sulfate dihydrate, dextrin, microcrystalline cellulose, lactose, pregelatinized starch, mannitol; commonly used binding agents include carboxymethyl cellulose sodium, PVP-K30, hydroxypropyl cellulose, starch slurry, methyl cellulose, ethyl cellulose, hydroxypropylmethyl cellulose, gelatinized starch; commonly used disintegrating agents include dry starch, cross-linked polypyrrolidone, cross-linked carboxymethyl cellulose sodium, carboxymethyl starch sodium, low-substituted hydroxypropyl cellulose; and commonly used lubricants include magnesium stearate, talc powder, sodium dodecyl sulfate, superfine silica power.

For parenteral administration, it can be processed to form injections. The injections refer to solutions, emulsions or suspensions with drug for injection in body, as well as sterile preparations in form of powder or concentrated solutions that are diluted to form solution or suspension before clinical use. The injections comprise injection solution, sterile powder for injection, concentrated solution for injection. When preparing injections, conventional preparation methods in the art can be used, in which aqueous solvents or nonaqueous solvents can be used. The most common aqueous solvent is water for injection. 0.9% sodium chloride solution or other suitable aqueous solutions can also be used. Common nonaqueous solvents comprise vegetable oils, such as soybean oil for injection, other solvents comprise water solution of ethanol, propylene glycol, polyethylene glycol. When preparing injections, additives may not be added, or suitable additives, such as osmotic pressure regulators, pH regulators, solubilizing agents, filling agents, antioxidants, bacteriostatic agents, emulsifying agents, suspending aids, can be added according to the properties of drug. The common osmotic pressure regulators comprise sodium chloride, glucose, potassium chloride, magnesium chloride, calcium chloride, sorbitol, preferably, sodium chloride or glucose; common pH regulators comprise acetic acid-sodium acetate, lactic acid, citric acid-sodium citrate, sodium hydrogen carbonate-sodium carbonate; common solubilizing agents comprise polysorbate 80, propylene glycol, lecithin, polyoxyethylated castor oil; common filling agents comprise lactose, mannitol, sorbitol, dextran; common antioxidants comprise sodium sulfite, sodium hydrogen sulfite, sodium pyrosulfite; common bacteriostatic agents comprise phenol, cresol, trichlorobutanol.

The compound of Formula (I) of the present invention, pharmaceutically acceptable salts or stereoisomers thereof have better activity of inhibiting PDE-5 (phosphodiesterase-5), can be used in manufacture of a medicament for prophylaxis or treatment of diseases such as sexual dysfunction and lower urinary tract symptoms which are caused by cGMP signal transduction dysfunction. Hence, the present invention further seeks to protect a use of the compound of Formula (I), its pharmaceutically acceptable salts or stereoisomers in manufacture of a medicament for enhancing cGMP signal transduction.

The therapeutic method according to the present invention comprises administering a patient with a therapeutically effective amount of the compound of the present invention (or pharmaceutically acceptable salt or stereoisomer thereof) for treatment or prophylaxis of the above diseases, in which the administration amount and duration time must be sufficient to achieve the required effects. In the present invention, "therapeutically effective amount" refers to an amount of the compound that is sufficient to alleviate symptoms of patient.

The dosage of the compound of the present invention is determined by physicians on basis of reasonable medical judgment. Specific dosage for any specific patient should be determined various factors, including kind and severity of disorder, activity of the used compound of the present invention, age, bodyweight and health condition, gender and dietary habit of the patient, number of administration, route of administration, excretion rate of the used compound of the present invention, course of treatment, drugs to be used in combination with the compound of the present invention, and similar factors well-known in medical and pharmaceutical fields.

Total daily dosage can be for example, 0.01-50 mg/kg bodyweight, or 0.1-25 mg/kg bodyweight, for the compound of the present invention when administering to patent by single dose or divided doses. In an embodiment, the therapeutic schedule according to the present invention comprises administering patient in need of this therapy with about 10 mg to about 1000 mg of one or more compounds of the present invention via single dose or divided doses per day. In another embodiment, the therapeutic schedule comprises administering patient in need of this therapy with about 10 mg to about 500 mg of one or more compounds of the present invention via single dose or divided doses per day.

The compound of Formula (I) of the present invention, pharmaceutically acceptable salt or stereoisomer thereof can form a pharmaceutical composition with one or more second therapeutically active agents, in which the therapeutically active agents are selected from vasodilators, prostaglandin E1, prostacyclin, α-adrenergic receptor blockers, mixed a, β-blockers, α-blockers (e.g., Alfuzosin), 5α-reductase inhibitors, α2-adrenergic receptor blockers, ACE inhibitors, NEP inhibitors, central dopamine agents, vasoactive intestinal peptides, calcium channel blockers, thiazines, endothelin receptor agonists (e.g., bosentan), androgen (e.g., testosterone), propionyl-L-carnitine, prostacyclin analogs (e.g., beraprost, iloprost), 5-hydroxytryptamine reuptake inhibitor (trazodone), or mixtures thereof.

The beneficial effects of the compound of the present invention are further illustrated via in vitro pharmacological activity tests as follows, but it does not mean that the compound of the present invention only have the following beneficial effects.

Experiment 1

In Vitro Pharmacological Activity of the Compounds of the Present Invention

Samples to be Tested:

Some compounds of the present invention, see Table 1, self-made, which chemical names and structures are what mentioned above; Avanafil, purchased from market, which structure is what mentioned above.

Experimental Method

Enzyme Assay

Caliper Mobility-Shift PDE-5A Assay:

A sample to be tested is precisely weighed, dissolved by adding DMSO, mixed sufficiently to form 10 mM solution. The above mother solution is diluted with DMSO to 0.5 mM, then diluted in 3.162 gradient multiple to obtain total 11 concentrations.

20 μl of substrate 10 μM FL-cGMP was added to 96-well plate, to which was added 1 μl of compound DMSO solution or compound-free DMSO solution, then was added 29 μl of 1.38 ng/μl PDE-5A enzyme buffer solution (100 mM Hepes pH 7.5, 5 mM $MgCl_2$, 0.002% Brij-35). The maximum final concentration of the compound was 10 μM. After incubation at 30° C. for 1 h, 20 μl of 70 μM EDTA was added to terminate reaction. Substrate and products were separated and analyzed by electrophoresis. Conversion rate was calculated by Caliper's Reviewer software, and inhibition rate was calculated by the following formulation, and $IC_{50}$ was calculated from inhibition rate using Prism 5.0.

Inhibition rate=[conversion rate (ZPE)−conversion rate (sample)]×100/[conversion rate (ZPE)−conversion rate (HPE)]

Notation: HPE: blank control without adding enzyme; ZPE: blank control without adding compound.

Experimental Results and Conclusions

TABLE 1

$IC_{50}$ values for PDE-5A of the compounds of the present invention

| Compound | PDE-5A (nM) | Avanafil/PDE-5A (nM) |
|---|---|---|
| 1 | 0.1721 | 17.32 |
| 6 | 0.075 | 17.32 |
| 3 | 0.1 | 17.32 |
| 4 | 0.028 | 17.32 |
| 2 | 4.013 | 10.77 |
| 7 | 0.7389 | 10.77 |
| 8 | 0.4765 | 10.77 |
| 5 | 0.5287 | 10.77 |
| 9 | 0.1858 | 10.77 |
| 10 | 1.14 | 10.77 |
| 11 | 0.9353 | 10.77 |
| 13 | 0.2127 | 10.77 |
| 14 | 1.976 | 10.77 |
| 15 | 0.1188 | 10.77 |
| 12 | 0.719 | 10.77 |
| 17 | 2.077 | 19.22 |
| 18 | 1.44 | 12.65 |
| 19 | 4.079 | 12.65 |

Conclusion: Table 1 shows the compounds of the present invention had better inhibition activity on PDE-5A.

Experiment 2

Determination of Half-Life

1. Experimental Design

| Animal number | gender | Administration route | Time of blood sampling | Type of biological sample |
|---|---|---|---|---|
| 3 | Male | Intragastric administration (PO) | 0 min, 5 min, 15 min, 30 min, 1 h, 2 h, 4 h, 6 h, 8 h, 24 h | Blood plasma |
| 3 | Male | Intravenous injection (IV) | | |

2. Samples to be Tested

Avanafil as control drug and the compounds of the present invention (self-made) were dissolved with suitable solvents.

3. Devices

Instruments: API4000 LC-MS/MS
Chromatography column: Agilent XDB $C_{18}$ (2.1×50 mm, 5 μm)

4. Blood Sampling

Blood sampling in rats: animals were fixed, tails were heated with water-bath at 10 min before each time point, about 100 μl of blood was collected via caudal vein, and the collected blood samples were placed in heparin sodium-containing anticoagulation tubes. The blood samples were centrifuged at 4° C. and 8,000 rpm for 6 min to obtain blood plasma samples, in which the blood plasma samples should be prepared with 30 min after blood sampling. The blood plasmas were stored in refrigerator with −80° C.

5. Experimental Methods (1) Samples to be tested were taken out from refrigerator (−80° C.), melt at room temperature, then subjected to volution for 5 min;
(2) 20 μl of sample was precisely moved to 1.5 ml centrifuge tube;
(3) 200 μl of internal standard solution was added;
(4) After 5 min of volution, 5 min of centrifugation (12,000 rpm) was carried out;
(5) 100 μl of supernatant was precisely taken, 100 μl of water was added, subjected to volution for 5 min, and analyzed by LC-MS/MS.

6. Method for Data Treatment

Concentrations of samples to be tested (blood plasma samples) were the output results of Analyst 1.5.1 of AB SCIEX (Shanghai Aibocaisi Analytical Instruments Trading Co., Ltd.). Mean values, standard deviations and parameters such as variable coefficients were calculated by Microsoft Excel (when parameters were directly given by Analyst 1.5.1, they were not calculated). PK parameters were calculated using Pharsight Phoenix 6.1 software.

7. Experimental Results and Conclusions

TABLE 2

Half-life results of PDE5s compounds in SD rats

| Compound | Dose mg/kg | $t_{1/2}$ (h) IV | Dose mg/kg | $t_{1/2}$ (h) PO |
|---|---|---|---|---|
| Avanafil | Administration alone 2 | 0.53 | Administration alone 2 | 0.51 |
| 1 | Administration alone 1 | 3.96 | Administration alone 2 | No bioavailability |
| 2 | Administration alone 1 | 1.51 | Administration alone 2 | No bioavailability |
| 4 | Administration alone 1 | 0.66 | Administration alone 1 | No bioavailability |
| 6 | Administration alone 1 | 1.74 | Administration alone 1 | No bioavailability |
| 7 | Administration alone 2 | 1.02 | Administration alone 4 | 1.59 |
| 8 | Administration alone 1 | 1.34 | Administration alone 1 | No bioavailability |
| 10 | Administration alone 1 | 2.35 | Administration alone 1 | No bioavailability |
| 12 | Administration alone 1 | 1.44 | Administration alone 1 | 1.94 |
| 14 | Administration alone 1 | 2.21 | Administration alone 1 | No bioavailability |
| 15 | Administration alone 1 | 3.32 | Administration alone 1 | No bioavailability |
| 17 | Administration alone 1 | 1.64 | Administration alone 2 | 3.26 |

TABLE 2-continued

Half-life results of PDE5s compounds in SD rats

| Compound | Dose mg/kg | $t_{1/2}$ (h) IV | Dose mg/kg | $t_{1/2}$ (h) PO |
|---|---|---|---|---|
| 19 | Administration alone 1 | 1.17 | Administration alone 2 | 1.97 |
| 20 | Administration alone 1 | 0.87 | Administration alone 1 | No bioavailability |

Conclusions: in comparison with Avanafil, the half-life values of the compounds of the present invention as measured by IV and PO manner in rats were longer than those of Avanafil, so their pharmacological activity could sustain for a long period, and thus they could be used for not only treatment of ED, but also treatment of lower urinary tract symptoms such as BPH/OAB, showing prospective use in clinical application.

Experiment 3

Determination of In Vivo Pharmacological Activity (Intravenous Injection)

Samples to be Tested:

some compounds of the present invention, see Table 3, Table 4, Table 5, Table 6, self-made, which chemical names and structures are mentioned above; Avanafil, purchased from market, which structure is mentioned above.

Experimental Method

New Zealand rabbits were subjected to adapt environment, and the rabbits were catched everyday before experiment so that the rabbits were used to repeated catching operation, then administration and stimulation were lunched. The animals were randomly divided according to bodyweight, samples to be tested were separately dissolved with solvent (Table 3 group: Avanafil and Compound 19 were separately dissolved with 5% DMSO+30% Cremophor EL+65% water for injection; Table 4 group, Table 5 group: Avanafil, Compound 14, Compound 17 and Compound 7 were separately dissolved with 45% DMA+20% Cremophor EL+35% water for injection; Table 6 group: Avanafil and Compound 15 were separately dissolved with 30% DMF+50% PEG-400+20% water for injection), corresponding samples to be tested were injected via ear flange veins of these groups, Table 3, Table 4, Table 5, Table 6 groups all had dose of 10 mg/kg, administration volume of 2 ml/kg, 0.2 mg/kg of sodium nitroprusside was intravenously injected in administration volume of 0.5 ml/kg after 5 min of administration.

Lengths of penis of rabbits were measured by digital vernier caliper separately before administration and at 5, 10, 15, 30, 50, 60, 90 and 120 min after administration. During each measurement, touching between penis and vernier caliper should be avoided.

TABLE 3

Effects on penis length (AUC) by intravenous administration in New Zealand rabbits

| Compound | AUC (mm × min) |
|---|---|
| Avanafil | 155.1 |
| Compound 19 | 523.3 |

TABLE 4

Effects on penis length (AUC) by intravenous administration in New Zealand rabbits

| Compound | AUC (mm × min) |
|---|---|
| Avanafil | 132.3 |
| Compound 17 | 300.9 |

TABLE 5

Effects on penis length (AUC) by intravenous administration in New Zealand rabbits

| Compound | AUC (mm × min) |
|---|---|
| Avanafil | 168.3 |
| Compound 14 | 290.1 |
| Compound 7 | 191.5 |

TABLE 6

Effects on penis length (AUC) by intravenous administration in New Zealand rabbits

| Compound | AUC (mm × min) |
|---|---|
| Avanafil | 146.4 |
| Compound 15 | 339.3 |

Conclusion: Table 3, Table 4, Table 5, Table 6 showed that the compounds of the present invention could prompt erection of penis in New Zealand rabbits, and had better effects than Avanafil.

EMBODIMENTS OF THE INVENTION

The above contents of the present invention are further illustrated by the following examples. However, the scopes of the above subject matters of the present invention are not limited to the following examples, and all technical solutions based on the above contents of the present invention fall within the scope of the present invention.

Example 1

Preparation of -benzyl-2-(3-azadicyclo[3.1.0]hexan-3-yl)-4-(3-chloro-4-methoxybenzyloxy)pyrimidine-5-carboxamide (Compound 1)

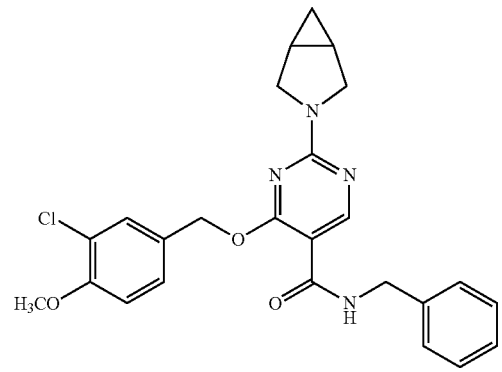

(1) Preparation of ethyl 4-(3-chloro-4-methoxybenzyloxy)-2-(methylmercapto)pyrimidine-5-carboxylate

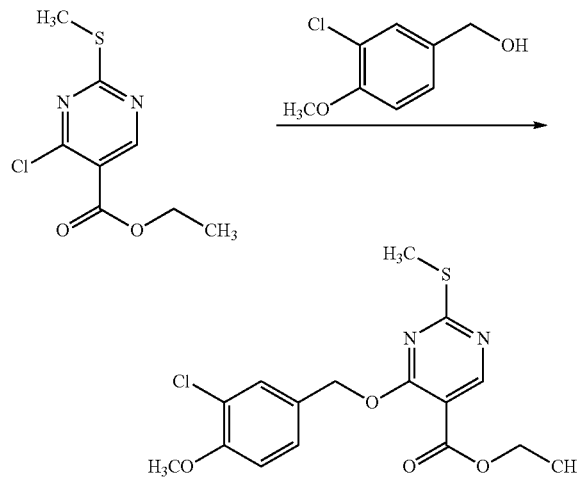

3-Chloro-4-methoxybenzyl alcohol (20 g, 116 mmol) was dissolved in 200 mL of DMF, NaH (7.0 g, 174 mmol) was added under ice-water-bath. After 1 h of reaction, ethyl 4-chloro-2-(methylmercapto)pyrimidine-5-carboxylate (27 g, 116 mmol) was added in portions for continuing the reaction for 3 h. 300 mL of water was added, extraction was performed with ethyl acetate, the organic layer was dried, concentrated and separated with silica gel column (petroleum ether: ethyl acetate=10:1) to obtain ethyl 4-(3-chloro-4-methoxybenzyloxy)-2-(methylmercapto)pyrimidine-5-carboxylate as white solid (5.0 g, 12%).

(2) Preparation of 4-(3-chloro-4-methoxybenzyloxy)-2-(methylmercapto)pyrimidine-5-carboxylic Acid

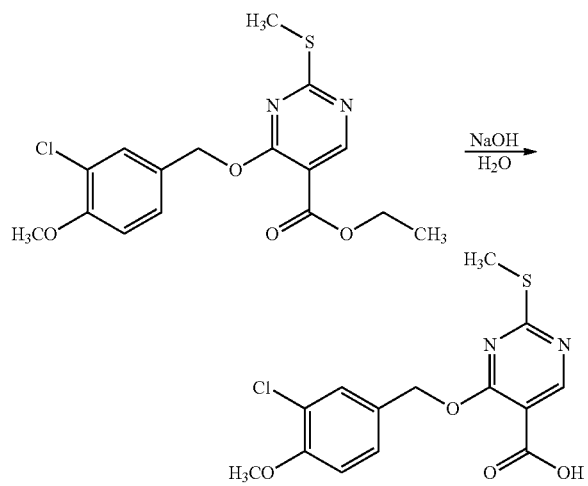

Ethyl 4-(3-chloro-4-methoxybenzyloxy)-2-(methylmercapto)pyrimidine-5-carboxylate (3.0 g, 8.15 mmol) and sodium hydroxide (652 mg, 16.3 mmol) were dissolved in 10 mL of water and 50 mL of THF, reacted at room temperature for 5 h. The diluted hydrochloric acid was added to adjust to pH=6, extraction was performed with dichloromethane (30 mL×3), the extract was dried and concentrated to obtain a white solid, and this product was directly used in the next reaction without purification.

(3) Preparation of N-benzyl-4-(3-chloro-4-methoxybenzyloxy)-2-(methylmercapto) pyrimidine-5-carboxamide

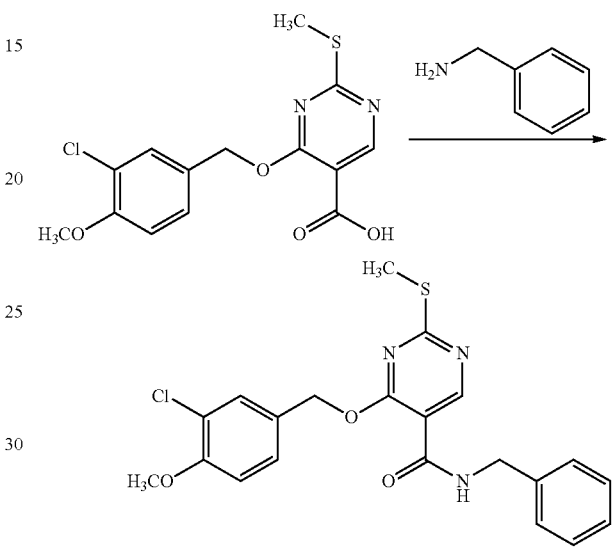

4-(3-chloro-4-methoxybenzyloxy)-2-(methylmercapto) pyrimidine-5-carboxylic acid (2.2 g, 6.47 mmol), benzylamine (1.0 g, 9.34 mmol) and HATU (2.95 g, 7.76 mmol) were dissolved in 60 mL of THF, DIEA (N,N-diiso-propylethylamine, 3.36 mL, 19.41 mmol) was added dropwise, reacted at room temperature for 8 h. To the reaction solution was added 100 mL of water and then extracted with dichloromethane (50 mL×3), dried with anhydrous sodium sulfate, dried by rotation, the solid was separated with silica gel column (dichloromethane:methanol=100:1) to obtain a white solid N-benzyl-4-(3-chloro-4-methoxybenzyloxy)-2-(methylmercapto)pyrimidine-5-carboxamide 600 mg, 22% yield.

(4) Preparation of N-benzyl-4-(3-chloro-4-methoxybenzyloxy)-2-(methylsulfinyl) pyrimidine-5-carboxamide

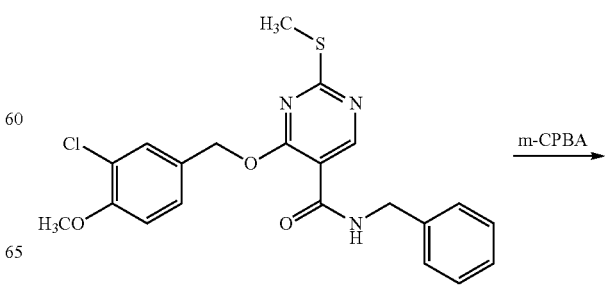

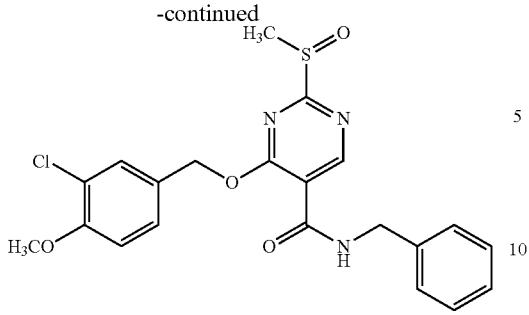

N-benzyl-4-(3-chloro-4-methoxybenzyloxy)-2-(methylmercapto)pyrimidine-5-carboxamide (100 mg, 0.23 mmol) was dissolved in 10 mL of dichloromethane, m-CPBA (m-chloroperbenzoic acid, 40 mg, 0.23 mmol) was added and reacted at room temperature for 3 h, washed with water after the reaction is complete, extracted with dichloromethane, the organic layer was dried and dried by rotation to obtain yellow solid, and this product was directly used in the next reaction without purification.

(5) Preparation of N-benzyl-2-(3-azadicyclo[3.1.0]hexan-3-yl)-4-(3-chloro-4-methoxybenzyloxy)pyrimidine-5-carboxamide

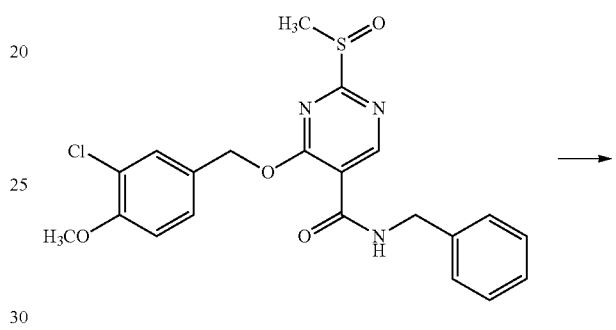

N-benzyl-4-(3-chloro-4-methoxybenzyloxy)-2-(methylsulfinyl)pyrimidine-5-carboxamide (100 mg, 0.22 mmol) and 3-azadicyclo[3.1.0]hexane hydrochloride (32 mg, 0.27 mmol) were dissolved in 10 mL of anhydrous THF, triethylamine (67 mg, 0.66 mmol) was added dropwise, reacted at room temperature for 8 h. After addition of water, extraction was performed with dichloromethane, drying was performed with anhydrous sodium sulfate, and separation was performed with column chromatography (dichloromethane:methanol=80:1) to obtain a white solid 26 mg, 25% yield.

Molecular formula: $C_{25}H_{25}ClN_4O_3$, molecular weight: 464.9, mass spectrum (m/e): 464.9 (M+1)

$^1$H NMR (400M, CDCl$_3$) δ: 8.98 (s, 1H), 7.56 (m, 1H), 7.55 (d, 1H), 7.15-7.38 (m, 5H), 7.13 (d, 1H), 6.79 (d, 1H), 5.31 (m, 2H), 4.56 (d, 2H), 3.96 (m, 2H), 3.92 (s, 3H), 3.62 (m, 2H), 1.67 (m, 2H), 0.80 (m, 1H), 0.22 (s, 1H).

Example 2

Preparation of N-benzyl-2-(3-oxa-8-azadicyclo[3.2.1]octan-8-yl)-4-(3-chloro-4-methoxybenzyloxy)pyrimidine-5-carboxamide (Compound 2)

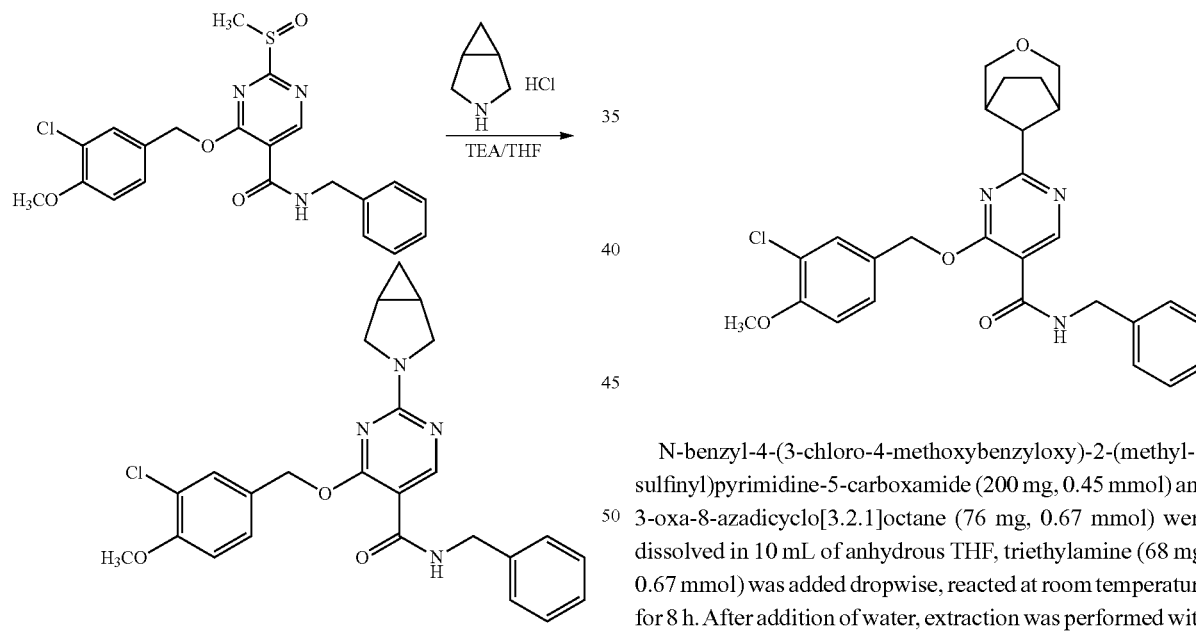

N-benzyl-4-(3-chloro-4-methoxybenzyloxy)-2-(methylsulfinyl)pyrimidine-5-carboxamide (200 mg, 0.45 mmol) and 3-oxa-8-azadicyclo[3.2.1]octane (76 mg, 0.67 mmol) were dissolved in 10 mL of anhydrous THF, triethylamine (68 mg, 0.67 mmol) was added dropwise, reacted at room temperature for 8 h. After addition of water, extraction was performed with dichloromethane, drying was performed with anhydrous sodium sulfate, and separation was performed with column chromatography (dichloromethane:methanol=150:1) to obtain a white solid 41 mg, 18% yield.

Molecular Formula: $C_{26}H_{27}ClN_4O_4$; molecular weight: 495.0; mass spectrum (m/e): 495.2 (M+1)

$^1$H NMR (400M, CDCl$_3$) δ: 8.90 (s, 1H), 7.63 (m, 1H), 7.61 (d, 1H), 7.18-7.41 (m, 5H), 7.16 (d, 1H), 6.83 (d, 1H), 5.35 (m, 2H), 4.75 (d, 2H), 4.60 (m, 2H), 3.95 (s, 3H), 7.752 (m, 4H), 2.17 (m, 2H), 2.08 (m, 2H).

Example 3

Preparation of 2-(3-azadicyclo[3.1.0]hexan-3-yl)-4-(3-chloro-4-methoxy-benzyloxy)-N-(pyrimidin-2-ylmethyl)pyrimidine-5-carboxamide (Compound 3)

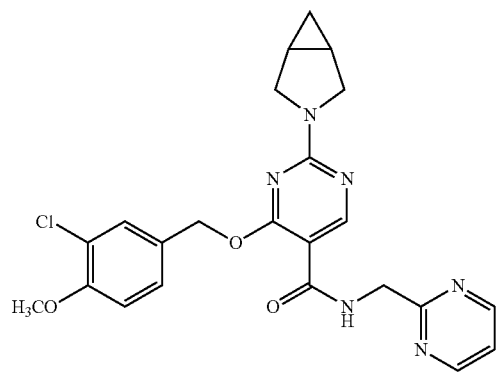

(1) Preparation of 4-(3-chloro-4-methoxybenzyloxy)-2-(methylmercapto)-N-(pyrimidin-2-ylmethyl)pyrimidine-5-carboxamide

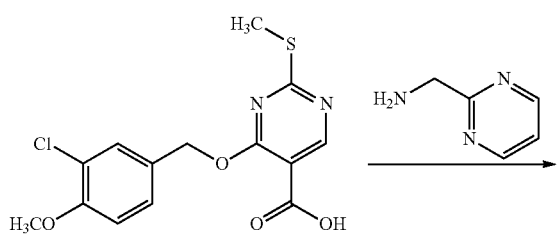

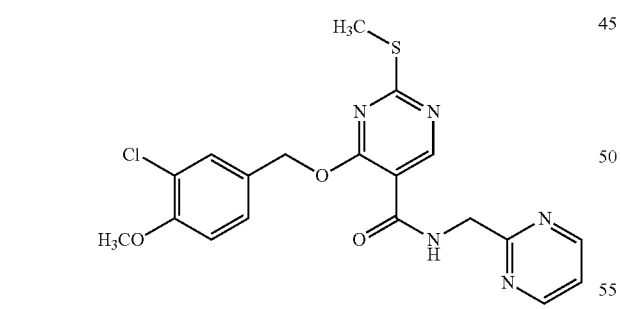

4-(3-chloro-4-methoxybenzyloxy)-2-(methylmercapto)pyrimidine-5-carboxylic acid (300 mg, 0.88 mmol), DIEA (0.5 mL, 2.88 mmol) were dissolved in 30 mL of THF, HATU (405 mg, 1.06 mmol) and pyrimidin-2-ylmethylamine (115 mg, 1.06 mmol) were added under ice-water-bath, reacted at room temperature overnight, to the reaction solution was added 100 mL of water, then extracted with dichloromethane, dried with anhydrous sodium sulfate, dried by rotation, then solid was separated with silica gel column (dichloromethane:methanol=40:1) to obtain a white solid 4-(3-chloro-4-methoxybenzyloxy)-2-(methylmercapto)-N-(pyrimidin-2-ylmethyl)pyrimidine-5-carboxamide 60 mg, yield 16%.

(2) Preparation of 4-(3-chloro-4-methoxybenzyloxy)-2-(methylsulfinyl)-N-(pyrimidin-2-ylmethyl)pyrimidine-5-carboxamide

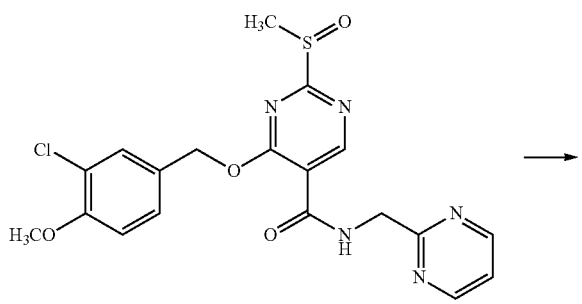

4-(3-chloro-4-methoxybenzyloxy)-2-(methylmercapto)-N-(pyrimidin-2-ylmethyl)pyrimidine-5-carboxamide (250 mg, 0.58 mmol) were dissolved in 20 mL of dichloromethane, m-CPBA (110 mg, 0.64 mmol) was added and reacted at room temperature for 12 h, washed with water after the reaction is complete, extracted with dichloromethane, the organic layer was dried, dried by rotation to obtain yellow solid 250 mg, yield 97%, this product was directly used in the next reaction without purification.

(3) Preparation of 2-(3-azadicyclo[3.1.0]hexan-3-yl)-4-(3-chloro-4-methoxybenzyloxy)-N-(pyrimidin-2-ylmethyl)pyrimidine-5-carboxamide

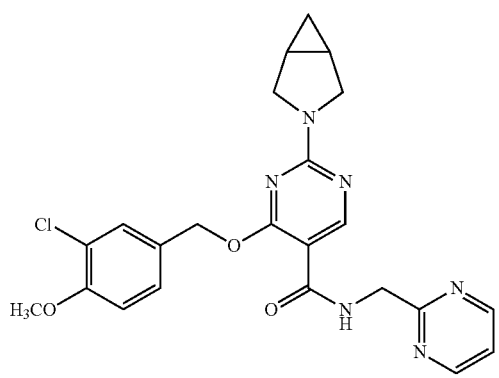

4-(3-chloro-4-methoxybenzyloxy)-2-(methylsulfinyl)-N-(pyrimidin-2-ylmethyl)pyrimidine-5-carboxamide (250 mg, 0.56 mmol) and DIEA (0.22 mL, 1.12 mmol) were dissolved in 30 mL of DCM, added 3-azadicyclo[3.1.0]hexane hydrochloride (71 mg, 0.60 mmol) under ice-water-bath, reacted at room temperature overnight. After addition of water, extraction was performed with dichloromethane, drying was performed with anhydrous sodium sulfate, separation was performed by column chromatography (dichloromethane:methanol=30:1) to obtain a white solid 50 mg, yield 19%.

Molecular Formula: $C_{23}H_{23}ClN_6O_3$ molecular weight: 466.9 mass spectrum (m/e): 466.9 (M+1)

$^1$H NMR (400M, CDCl$_3$) δ: 8.99 (s, 1H), 8.60 (d, 2H), 8.55 (m, 1H), 7.60 (d, 1H), 7.38 (d, 1H), 7.17 (t, 1H), 6.90 (d, 1H), 5.50 (m, 2H), 4.87 (d, 2H), 3.96 (m, 2H), 3.93 (s, 3H), 3.60 (m, 2H), 1.66 (m, 2H), 0.78 (m, 1H), 0.24 (s, 1H).

Example 4

Preparation of 2-(3-azadicyclo[3.1.0]hexan-3-yl)-4-(3-chloro-4-methoxybenzyloxy)-N-(pyridin-2-ylmethyl)pyrimidine-5-carboxamide (Compound 4)

(1) Preparation of 4-(3-chloro-4-methoxybenzyloxy)-2-(methylmercapto)-N-(pyridine 2-ylmethyl)pyrimidine-5-carboxamide

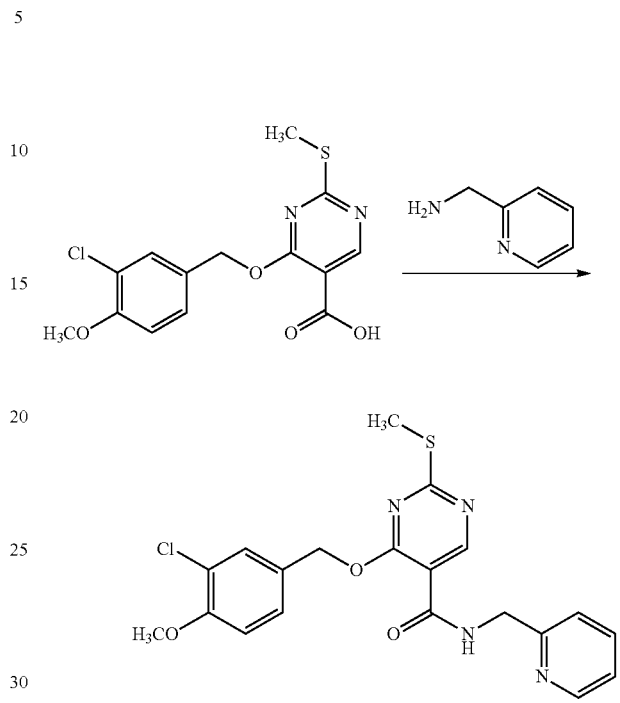

4-(3-chloro-4-methoxybenzyloxy)-2-(methylmercapto)pyrimidine-5-carboxylic acid (300 mg, 0.88 mmol) and pyridin-2-ylmethylamine (115 mg, 1.06 mmol) were dissolved in 10 mL of THF, triethylamine (141 mg, 1.4 mmol) was added dropwise, added HATU (405 mg, 1.06 mmol) under ice-water-bath, reacted at room temperature for 4 h, to the reaction solution was added 100 mL of water, then extracted with dichloromethane, dried with anhydrous sodium sulfate, dried by rotation, then the solid was separated with silica gel column (dichloromethane:methanol=20:1) to obtain a white solid 4-(3-chloro-4-methoxybenzyloxy)-2-(methylmercapto)-N-(pyridin-2-ylmethyl)pyrimidine-5-carboxamide 180 mg, yield 48%.

(2) Preparation of 4-(3-chloro-4-methoxybenzyloxy)-2-(methylsulfinyl)-N-(pyridin-2-ylmethyl)pyrimidine-5-carboxamide

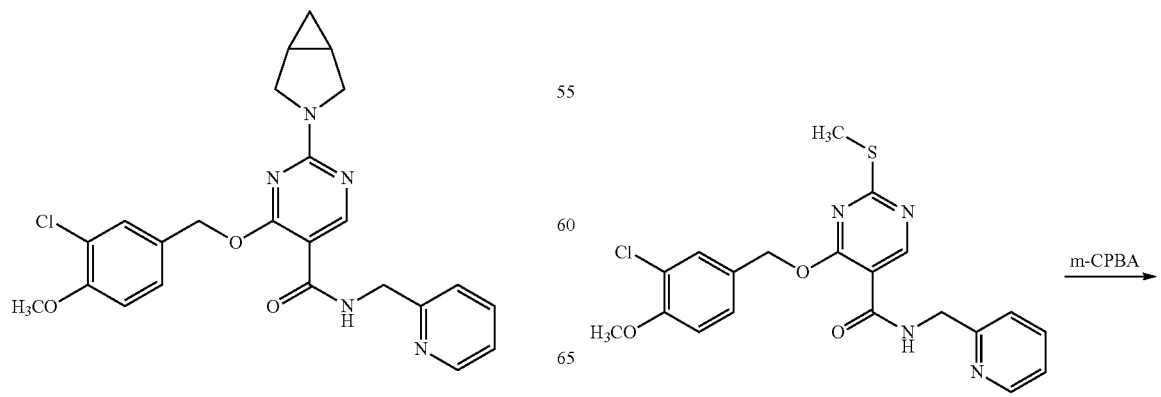

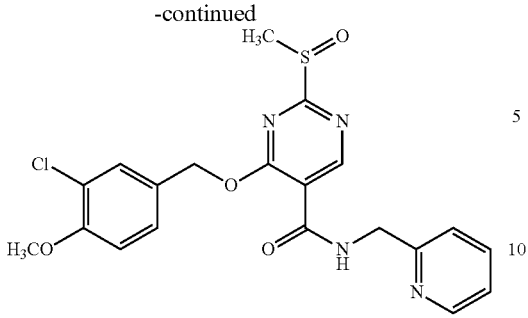

4-(3-chloro-4-methoxybenzyloxy)-2-(methylmercapto)-N-(pyridin-2-ylmethyl)pyrimidine-5-carboxamide (180 mg, 0.42 mmol) was dissolved in 20 ml of dichloromethane, m-CPBA (80 mg, 0.46 mmol) was added and reacted at room temperature for 12 h, washed with water after reaction, extracted with dichloromethane, the organic layer was dried, dried by rotation to obtain yellow solid, and this product was directly used in the next reaction without purification.

(3) Preparation of 2-(3-azadicyclo[3.1.0]hexan-3-yl)-4-(3-chloro-4-methoxybenzyloxy)-N-(pyridin-2-ylmethyl)pyrimidine-5-carboxamide

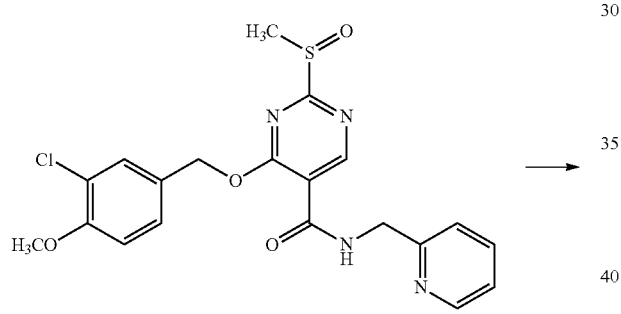

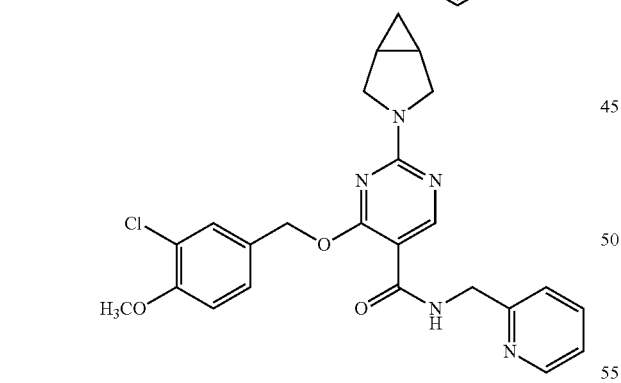

The above product 4-(3-chloro-4-methoxybenzyloxy)-2-(methylsulfinyl)-N-(pyridin-2-ylmethyl)pyrimidine-5-carboxamide and 3-azadicyclo[3.1.0]hexane hydrochloride (48 mg, 0.40 mmol) were dissolved in 10 mL THF, triethylamine (101 mg, 1 mmol) was added under ice-water-bath, reacted at room temperature for 4 h. After addition of water, extraction was performed with dichloromethane, drying was performed with anhydrous sodium sulfate, and separation via column chromatography (dichloromethane:methanol=20:1) was performed to obtain a white solid 35 mg, yield 19%.

Molecular Formula: $C_{24}H_{24}ClN_5O_3$ molecular weight: 465.9 mass spectrum (m/e): 466.0 (M+1)

$^1$H NMR (400M, $CDCl_3$) δ: 8.98 (s, 1H), 8.39 (d, 2H), 7.64 (t, 1H), 7.52 (d, 1H), 7.35 (d, 1H), 7.32 (t, 1H), 7.27 (m, 1H), 6.87 (d, 1H), 5.48 (m, 2H), 4.71 (d, 2H), 3.96 (m, 2H), 3.94 (s, 3H), 3.60 (m, 2H), 1.64 (m, 2H), 0.80 (m, 1H), 0.24 (m, 1H).

Example 5

Preparation of 2-(3-azadicyclo[3.1.0]hexan-3-yl)-4-(3-chloro-4-methoxy-benzyloxy)-N-[(5-methylpyrazin-2-yl)methyl]pyrimidine-5-carboxamide (Compound 5)

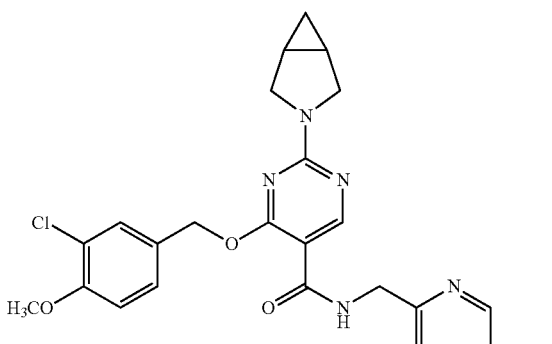

(1) Preparation of ethyl 4-(3-chloro-4-methoxybenzyloxy)-2-(methylsulfinyl)pyrimidine-5-carboxylate

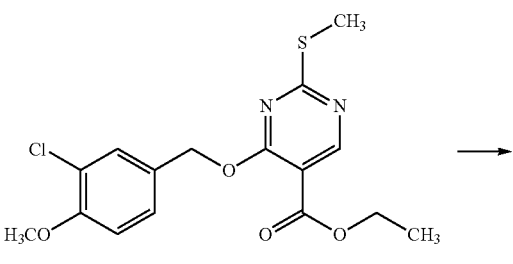

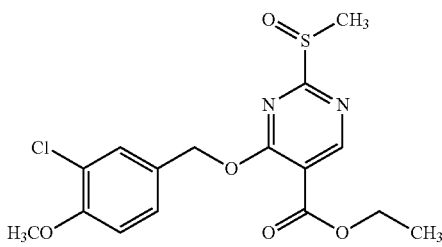

The procedure was the same as Example 1 (4), and the product was directly used in the next reaction without purification.

(2) Preparation of ethyl 2-(3-azadicyclo[3.1.0]hexan-3-yl)-4-(3-chloro-4-methoxy-benzyloxy)pyrimidine-5-carboxylate

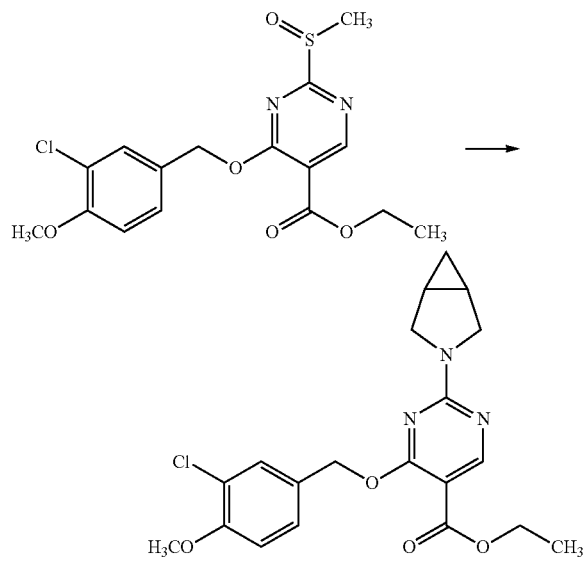

The procedure was the same as Example 1(5), 77% yield.

(3) Preparation of 2-(3-azadicyclo[3.1.0]hexan-3-yl)-4-(3-chloro-4-methoxybenzyloxy)pyrimidine-5-carboxylic Acid

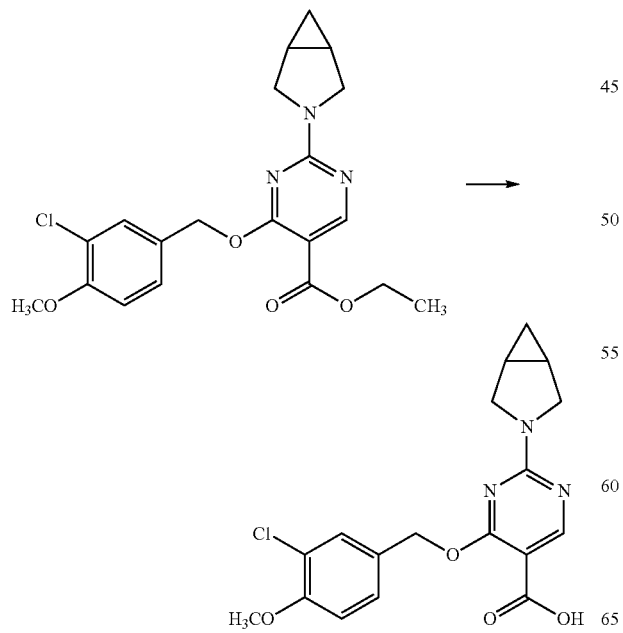

The procedure was the same as Example 1(2), 54% yield.

(4) Preparation of 2-(3-azadicyclo[3.1.0]hexan-3-yl)-4-(3-chloro-4-methoxybenzyloxy)-N-(5-methylpyrazin-2-yl)pyrimidine-5-carboxamide

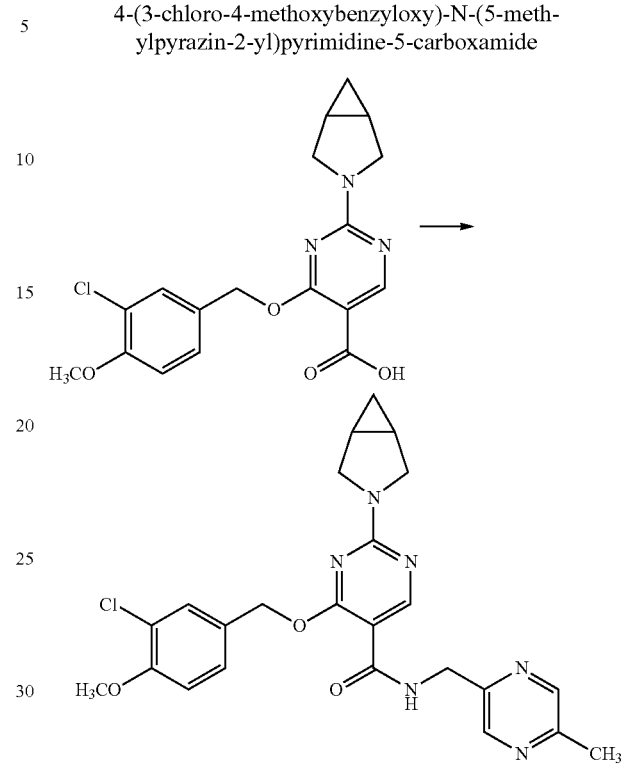

The procedure was the same as Example 1(3), 16% yield.

Molecular Formula: $C_{24}H_{25}ClN_6O_3$ molecular weight: 481.0 mass spectrum (m/e): 481.0 (M+1)

$^1$H NMR (400M, CDCl$_3$) δ: 8.97 (s, 1H), 8.46 (s, 1H), 8.23 (s, 1H), 8.20 (m, 1H), 7.50 (d, 1H), 7.33 (d, 1H), 6.91 (d, 1H), 5.43 (m, 2H), 4.70 (d, 2H), 3.97 (m, 2H), 3.93 (s, 3H), 3.60 (m, 2H), 2.56 (s, 3H), 1.67 (m, 2H), 0.81 (m, 1H), 0.24 (m, 1H).

Example 6

Preparation of 2-(3-azadicyclo[3.1.0]hexan-3-yl)-4-(3-chloro-4-methoxy-benzyloxy)-N-(4-fluorobenzyl)pyrimidine-5-carboxamide (Compound 6)

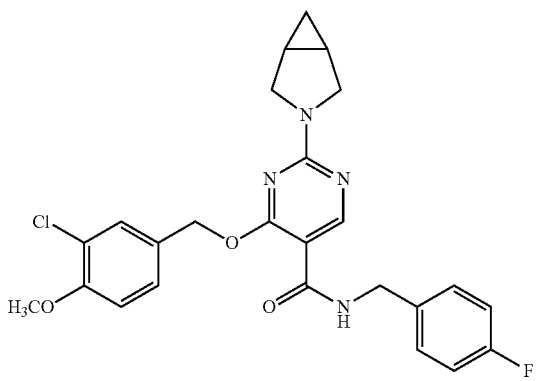 [SMILES: COc1ccc(COc2nc(N3CC4CC4C3)ncc2C(=O)NCc2ccc(F)cc2)cc1Cl]

(1) Preparation of 4-(3-chloro-4-methoxybenzyloxy)-2-(methylmercapto)-N-(4-fluorobenzyl)pyrimidine-5-carboxamide

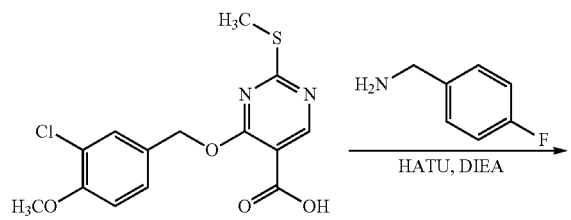

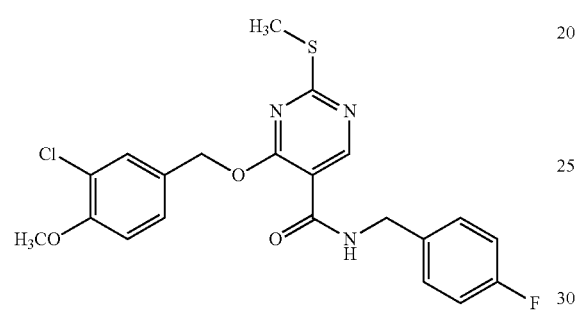

4-(3-chloro-4-methoxybenzyloxy)-2-(methylmercapto) pyrimidine-5-carboxylic acid (300 mg, 0.88 mmol) and 4-fluorobenzylamine (165 mg, 1.32 mmol) were dissolved in 20 mL THF, DIEA (0.45 mL, 2.64 mmol) was added dropwise, HATU (401 mg, 1.06 mmol) was added under ice-water-bath, reacted at room temperature for 4 h, to the reaction solution was added 100 mL of water, then extracted with dichloromethane, dried with anhydrous sodium sulfate, dried by rotation, the solid was separated with silica gel separation (dichloromethane:methanol=100:1) to obtain a white solid 4-(3-chloro-4-methoxybenzyloxy)-2-(methylmercapto)-N-(4-fluorobenzyl)pyrimidine-5-carboxamide 206 mg, yield 52%.

(2) Preparation of 4-(3-chloro-4-methoxybenzyloxy)-2-(methylsulfinyl)-N-(4-fluorobenzyl)pyrimidine-5-carboxamide

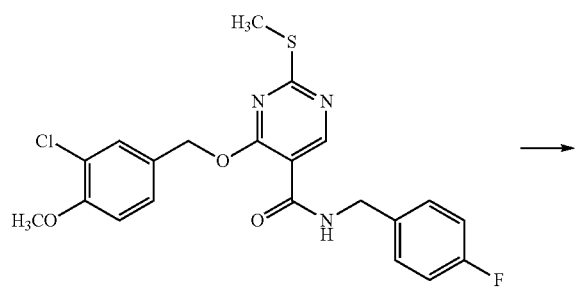

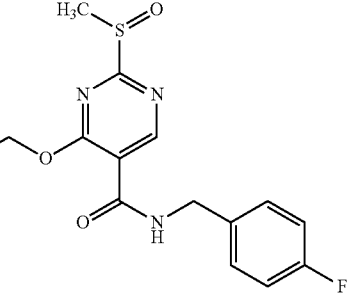

4-(3-chloro-4-methoxybenzyloxy)-2-(methylmercapto)-N-(4-fluorobenzyl)pyrimidine-5-carboxamide (206 mg, 0.46 mmol) was dissolved in 20 mL dichloromethane, m-CPBA (80 mg, 0.46 mmol) was added and reacted at room temperature for 12 h, the reaction solution was washed with water after the reaction is complete, extracted with dichloromethane, the organic layer was dried, dried by rotation to obtain yellow solid, the product was directly used in the next reaction without purification.

(3) Preparation of 2-(3-azadicyclo[3.1.0]hexan-3-yl)-4-(3-chloro-4-methoxy-benzyloxy)-N-(4-fluorobenzyl)pyrimidine-5-carboxamide

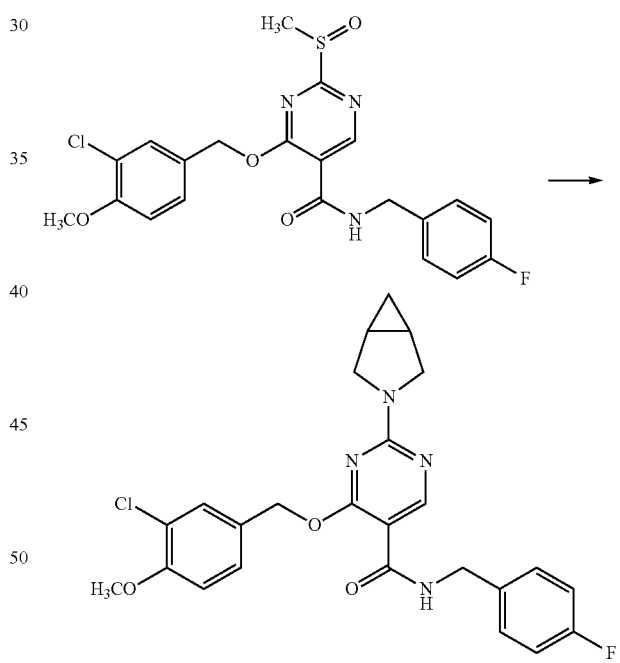

4-(3-chloro-4-methoxybenzyloxy)-2-(methylsulfinyl)-N-(4-fluorobenzyl)pyrimidine-5-carboxamide (200 mg, 0.43 mmol) and 3-azadicyclo[3.1.0]hexane hydrochloride (77 mg, 0.65 mmol) were dissolved in 10 mL of THF, triethylamine (130 mg, 1.29 mmol) was added under ice-water-bath, reacted at room temperature for 4 h. After addition of water, extraction was performed with dichloromethane, drying was performed with anhydrous sodium sulfate, separation via column chromatography (dichloromethane:methanol=100:1) was performed to obtain a white solid 48 mg, yield 23%.

Molecular Formula: $C_{25}H_{24}ClFN_4O_3$ molecular weight: 482.9 mass spectrum (m/e): 483.0 (M+1)

¹H NMR (400M, CDCl₃) δ: 8.97 (s, 1H), 7.52 (m, 1H), 7.50 (d, 1H), 7.11-7.15 (m, 3H), 6.96 (t, 2H), 6.80 (d, 1H), 5.32 (m, 2H), 4.48 (d, 2H), 3.95 (m, 2H), 3.93 (s, 3H), 3.60 (m, 2H), 1.66 (m, 2H), 0.80 (m, 1H), 0.25 (m, 1H).

Example 7

Preparation of 2-(3-azadicyclo[3.1.0]hexan-3-yl)-4-(3-chloro-4-methoxy-benzyloxy)-N-[(trans)-4-hydroxy cyclohexyl]pyrimidine-5-carboxamide (Compound 7)

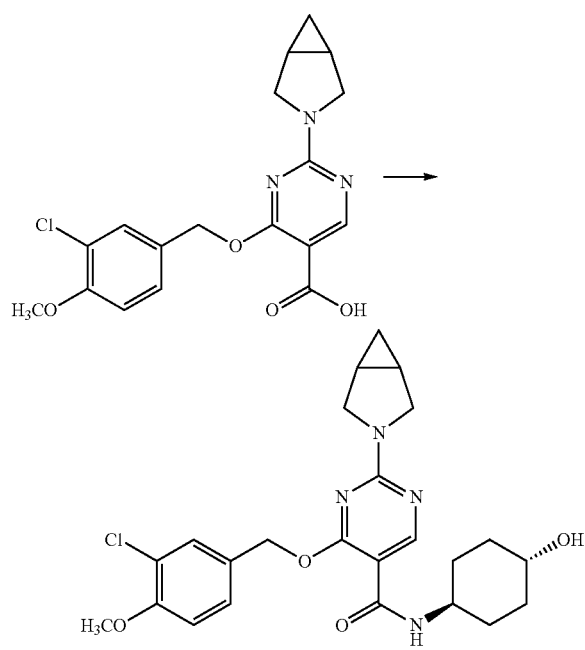

The procedure was the same as Example 1(3), yield 36%.
Molecular Formula: C₂₄H₂₉ClN₄O₄ molecular weight: 473.0 mass spectrum (m/e): 473.2 (M+1)
¹H NMR (400M, CDCl₃) δ: 8.96 (s, 1H), 7.52 (d, 1H), 7.33 (t, 1H), 7.30 (d, 1H), 7.00 (d, 1H), 5.38 (m, 2H), 3.99 (s, 3H), 3.97 (m, 2H), 3.96 (m, 1H), 3.64 (m, 2H), 3.62 (m, 1H), 2.06 (m, 2H), 1.92 (m, 2H), 1.70 (s, 1H), 1.67 (m, 2H), 1.45 (m, 2H), 1.20 (m, 2H), 0.84 (m, 1H), 0.25 (m, 1H).

Example 8

Preparation of 4-(3-chloro-4-methoxybenzyloxy)-N-(pyrimidin-2-ylmethyl)-2-(6-azaspiro[2.5]octan-6-yl)pyrimidine-5-carboxamide (Compound 8)

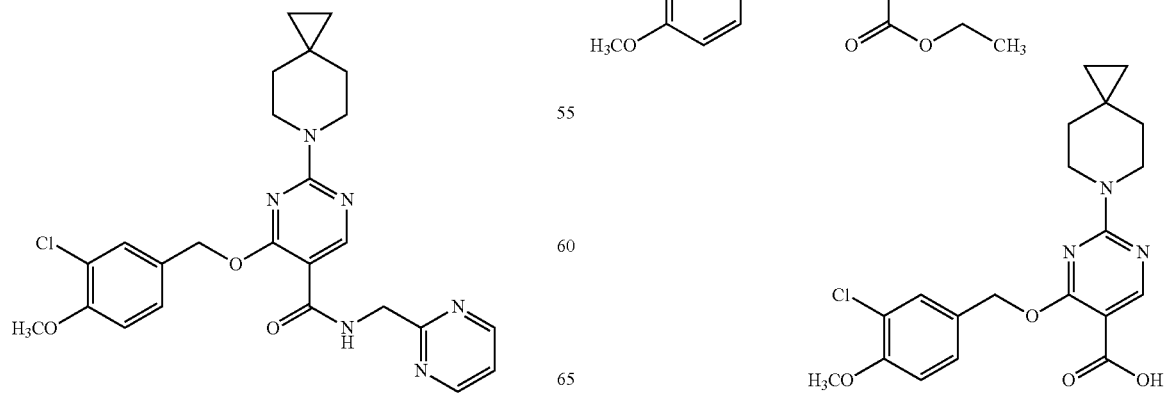

(1) Preparation of ethyl 4-(3-chloro-4-methoxybenzyloxy)-2-(6-azaspiro[2.5]octan-6-yl)pyrimidine-5-carboxylate

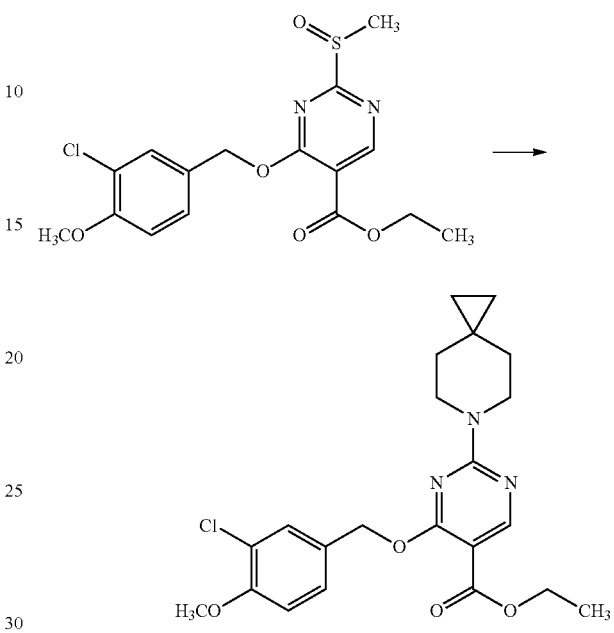

The procedure was the same as Example 1(5), yield 82%.

(2) Preparation of 4-(3-chloro-4-methoxybenzyloxy)-2-(6-azaspiro[2.5]octan-6-yl)pyrimidine-5-carboxylic Acid

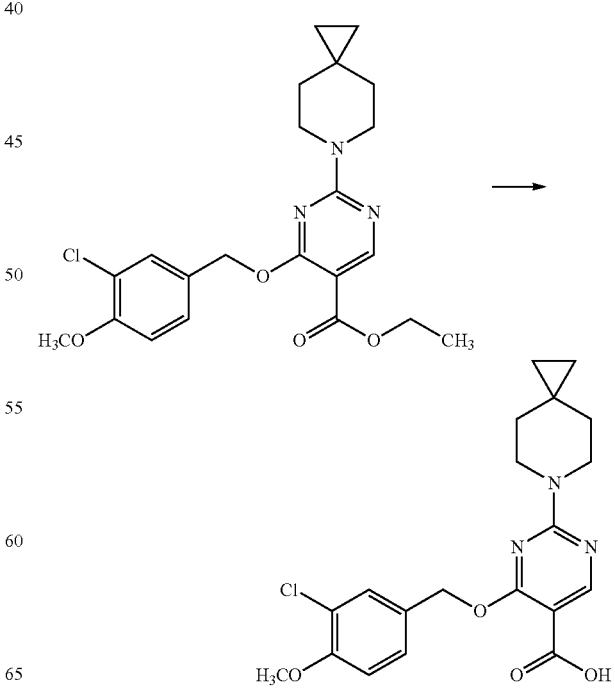

The procedure was the same as Example 1(2), yield 67%.

(3) Preparation of 4-(3-chloro-4-methoxybenzyloxy)-N-(pyrimidin-2-ylmethyl)-2-(6-azaspiro[2.5]octan-6-yl)pyrimidine-5-carboxamide

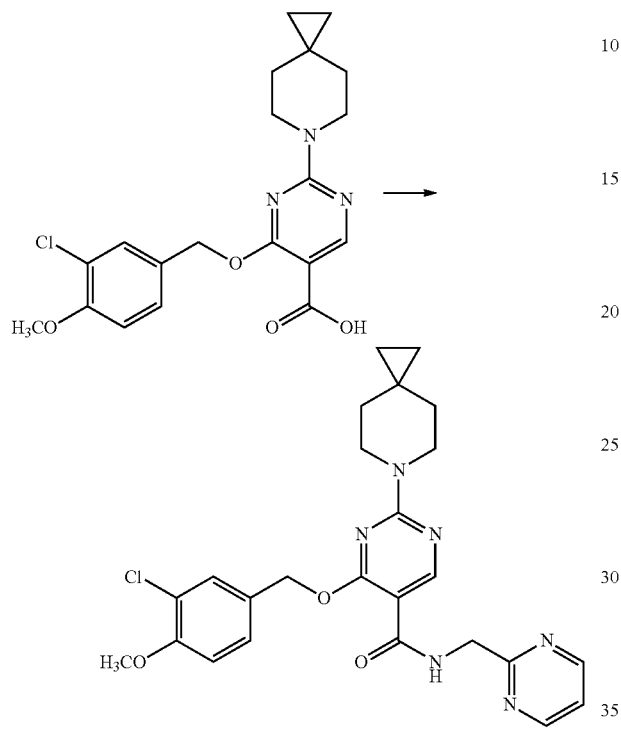

The procedure was the same as Example 1(3), yield 32%.
Molecular Formula: $C_{25}H_{27}ClN_6O_3$ molecular weight: 495.0 mass spectrum (m/e): 495.2 (M+1)
$^1$H NMR (400M, CDCl$_3$) δ: 9.00 (s, 1H), 8.61 (d, 2H), 8.60 (m, 1H), 7.60 (s, 1H), 7.39 (d, 1H), 7.19 (t, 1H), 6.91 (d, 1H), 5.48 (s, 2H), 4.88 (d, 2H), 3.96 (m, 4H), 3.93 (s, 3H), 1.45 (t, 4H), 0.42 (s, 4H).

Example 9

Preparation of 4-(3-chloro-4-methoxybenzyloxy)-N-(pyridin-2-ylmethyl)-2-(6-azaspiro[2.5]octan-6-yl)pyrimidine-5-carboxamide (Compound 9)

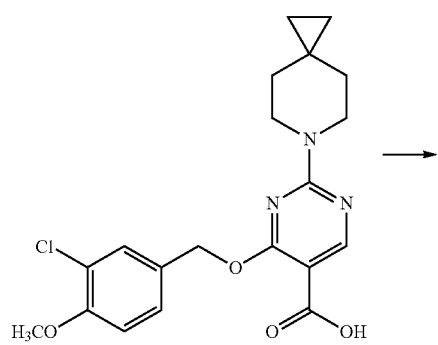

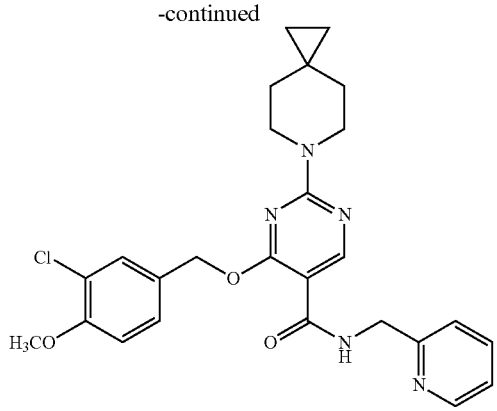

The procedure was the same as Example 1(3), yield 49%.
Molecular Formula: $C_{26}H_{28}ClN_5O_3$ molecular weight: 494.0 mass spectrum (m/e): 494.2 (M+1)
$^1$H NMR (400M, CDCl$_3$) δ: 8.99 (s, 1H), 8.41 (m, 2H), 7.64 (t, 1H), 7.50 (s, 1H), 7.35 (d, 1H), 7.26 (d, 1H), 7.17 (m, 1H), 6.88 (d, 1H), 5.45 (s, 2H), 4.72 (d, 2H), 3.95 (m, 4H), 3.92 (s, 3H), 1.44 (t, 4H), 0.41 (s, 4H).

Example 10

Preparation of N-benzyl-4-(3-chloro-4-methoxybenzyloxy)-2-(6-azaspiro[2.5]octan-6-yl)pyrimidine-5-carboxamide (Compound 10)

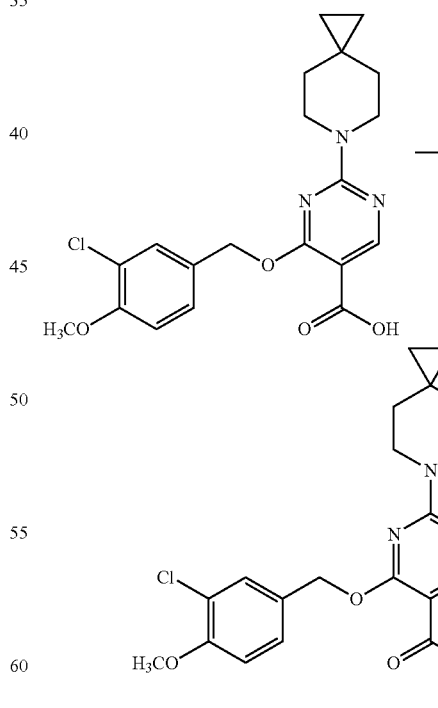

The procedure was the same as Example 1(3), yield 21%.
Molecular Formula: $C_{27}H_{29}ClN_4O_3$ molecular weight: 493.0 mass spectrum (m/e): 493.2 (M+1)

<sup>1</sup>H NMR (400M, CDCl<sub>3</sub>) δ: 9.00 (s, 1H), 7.59 (m, 1H), 7.38 (s, 1H), 7.15-7.31 (m, 5H), 7.13 (d, 1H), 6.80 (d, 1H), 5.33 (s, 2H), 4.56 (d, 2H), 3.94 (m, 4H), 3.92 (s, 3H), 1.43 (t, 4H), 0.41 (s, 4H).

Example 11

Preparation of 4-(3-chloro-4-methoxybenzyloxy)-N-(2-morpholinylethyl)-2-(6-azaspiro[2.5]octan-6-yl)pyrimidine-5-carboxamide (Compound 11)

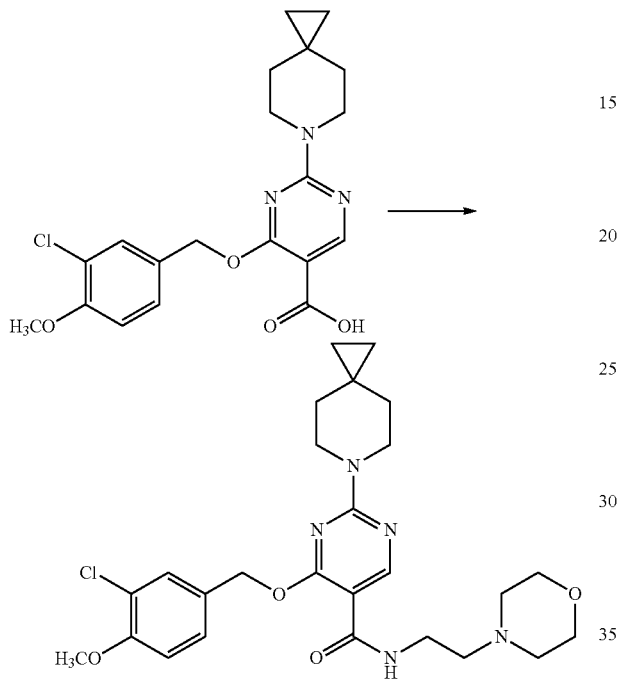

The procedure was the same as Example 1(3), yield 22%.
Molecular Formula: $C_{26}H_{34}ClN_5O_4$ molecular weight: 516.0 mass spectrum (m/e): 516.3 (M+1)

<sup>1</sup>H NMR (400M, CDCl<sub>3</sub>) δ: 8.93 (s, 1H), 7.75 (m, 1H), 7.48 (s, 1H), 7.31 (t, 1H), 6.93 (d, 1H), 5.44 (s, 2H), 3.92 (m, 4H), 3.91 (s, 3H), 3.62 (m, 4H), 3.53 (m, 2H), 2.60 (t, 2H), 2.35 (m, 4H), 1.46 (t, 4H), 0.40 (s, 4H).

Example 12

Preparation of 4-(3-chloro-4-methoxybenzyloxy)-N-[(trans)-4-hydroxy cyclohexyl]-2-(6-azaspiro[2.5]octan-6-yl)pyrimidine-5-carboxamide (Compound 12)

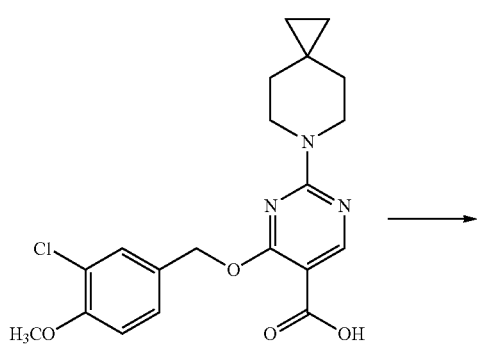

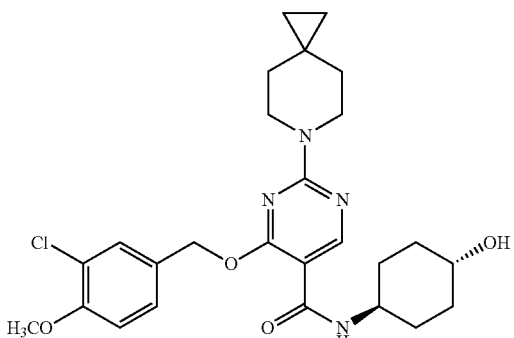

The procedure was the same as Example 1(3), yield 23%.
Molecular Formula: $C_{26}H_{33}ClN_4O_4$ molecular weight: 501.0 mass spectrum (m/e): 501.3 (M+1)

<sup>1</sup>H NMR (400M, CDCl<sub>3</sub>) δ: 8.93 (s, 1H), 7.47 (s, 1H), 7.28 (d, 1H), 7.19 (d, 1H), 6.94 (d, 1H), 5.34 (s, 2H), 3.93 (m, 8H), 3.58 (m, 1H), 2.02 (m, 2H), 1.88 (m, 2H), 1.40 (m, 8H), 0.39 (s, 4H).

Example 13

Preparation of 2-(3-azadicyclo[3.1.0]hexan-3-yl)-4-(3-chloro-4-methoxy-benzyloxy)-N-(2-morpholinyl-ethyl)pyrimidine-5-carboxamide (Compound 13)

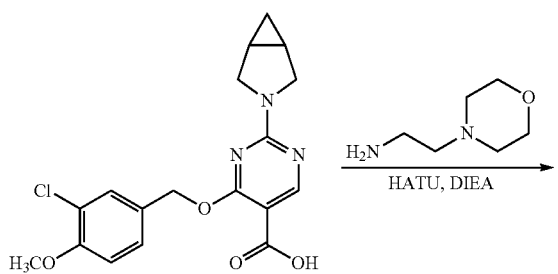

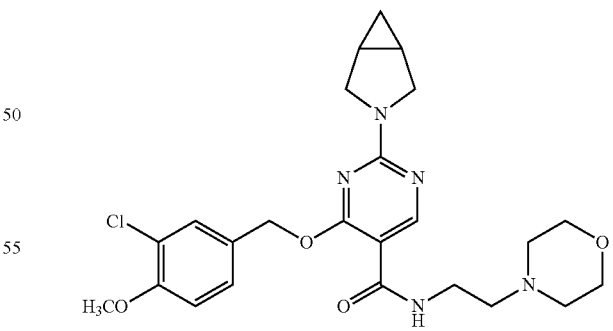

The procedure was the same as Example 1(3), yield 33%.
Molecular Formula: $C_{24}H_{30}ClN_5O_4$ molecular weight: 488.0 mass spectrum (m/e): 488.2 (M+1)

<sup>1</sup>H NMR (400M, CDCl<sub>3</sub>) δ: 8.92 (s, 1H), 7.71 (m, 1H), 7.47 (d, 1H), 7.30 (d, 1H), 6.92 (d, 1H), 5.43 (m, 2H), 3.90 (s, 3H), 3.89 (m, 2H), 3.58 (m, 6H), 3.49 (m, 2H), 2.52 (t, 2H), 2.42 (m, 4H), 1.64 (m, 2H), 0.78 (m, 1H), 0.20 (m, 1H).

Example 14

Preparation of N-benzyl-4-(3-chloro-4-methoxybenzyloxy)-2-(4-azaspiro[2.4]heptan-4-yl)-pyrimidine-5-carboxamide (Compound 14)

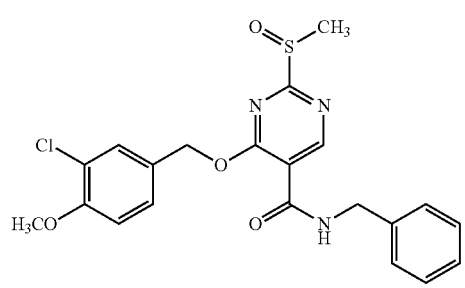

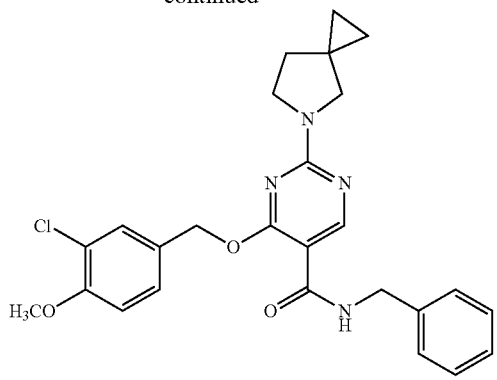

The procedure was the same as Example 2, yield 40%.

Molecular Formula: $C_{26}H_{27}ClN_4O_3$ molecular weight: 479.0 mass spectrum (m/e): 479.2 (M+1)

$^1$H NMR (400M, DMSO-d$_6$) δ: 8.60 (d, 1H), 8.18 (m, 1H), 7.59 (d, 1H), 7.40 (m, 1H), 7.20-7.27 (m, 5H), 7.08 (m, 1H), 5.43 (d, 2H), 4.44 (d, 2H), 3.83 (s, 3H), 3.68 (m, 2H), 3.42 (d, 2H), 1.86 (m, 2H), 0.62 (t, 4H).

Example 16

Preparation of 2-(3-azadicyclo[3.1.0]hexan-3-yl)-4-(3-chloro-4-methoxy-phenylethoxy)-N-[(trans)-4-hydroxycyclohexyl]pyrimidine-5-carboxamide (Compound 16)

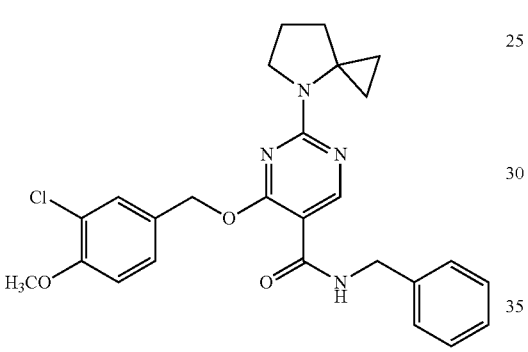

The procedure was the same as Example 2, yield 19%.

Molecular Formula: $C_{26}H_{27}ClN_4O_3$ molecular weight: 479.0 mass spectrum (m/e): 479.2 (M+1)

$^1$H NMR (400M, CDCl$_3$) δ: 8.99 (s, 1H), 7.52 (m, 1H), 7.35 (s, 1H), 7.25 (m, 3H), 7.17 (m, 2H), 7.10 (d, 1H), 6.77 (d, 1H), 5.31 (m, 2H), 4.52 (d, 2H), 3.91 (s, 3H), 3.83 (m, 2H), 2.00 (m, 6H), 0.53 (m, 2H).

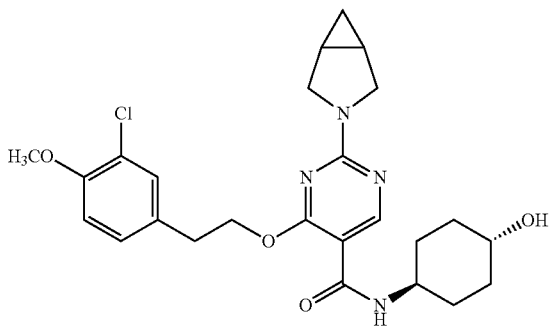 [SMILES: COc1ccc(CCOc2nc(N3CC4CC4C3)ncc2C(=O)N[C@H]2CC[C@H](O)CC2)cc1Cl]

(1) Preparation of ethyl 4-(3-chloro-4-methoxyphenylethoxy)-2-(methylmercapto)pyrimidine-5-carboxylate

Example 15

Preparation of N-benzyl-4-(3-chloro-4-methoxybenzyloxy)-2-(5-azaspiro[2.4]heptan-5-yl)-pyrimidine-5-carboxamide (Compound 15)

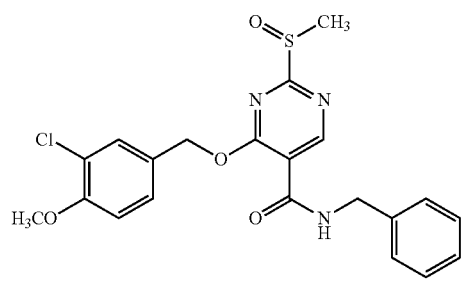

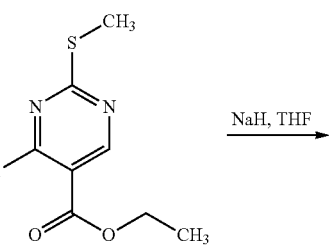 NaH, THF →

71
-continued

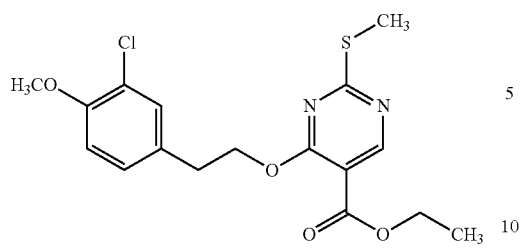

The procedure was the same as Example 1(1), yield 71%.

(2) Preparation of ethyl 4-(3-chloro-4-methoxyphenylethoxy)-2-(methylsulfinyl)pyrimidine-5-carboxylate

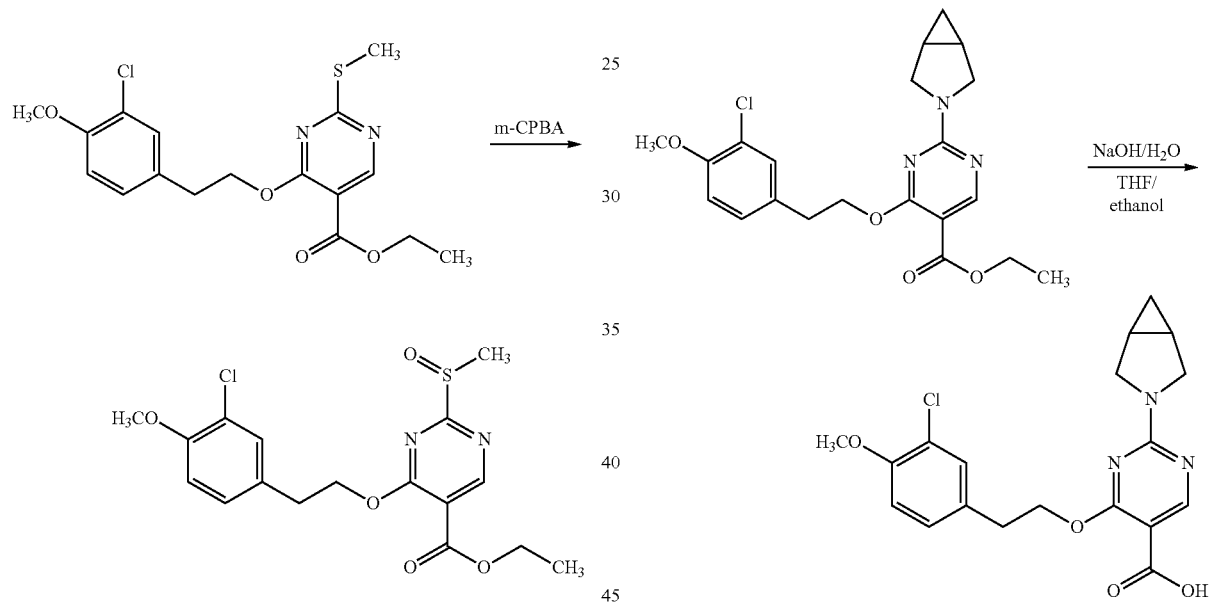

The procedure was the same as Example 1(4), the product was directly used in the next reaction without purification.

(3) Preparation of ethyl 2-(3-azadicyclo[3.1.0]hexan-3-yl)-4-(3-chloro-4-methoxy-phenylethoxy)pyrimidine-5-carboxylate

72
-continued

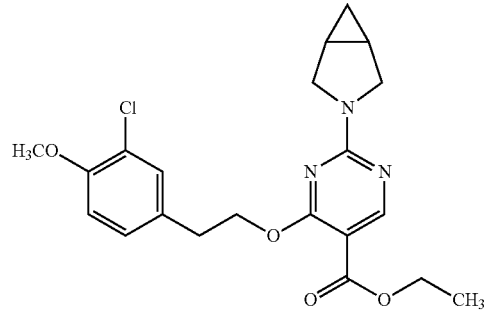

The procedure was the same as Example 1(5), yield 69%.

(4) Preparation of 2-(3-azadicyclo[3.1.0]hexan-3-yl)-4-(3-chloro-4-methoxy-phenylethoxy)pyrimidine-5-carboxylic acid The procedure was the same as Example 1(2), yield 71%.

(5) Preparation of 2-(3-azadicyclo[3.1.0]hexan-3-yl)-4-(3-chloro-4-methoxy-phenylethoxy)-N-[(trans)-4-hydroxycyclohexyl]pyrimidine-5-carboxamide

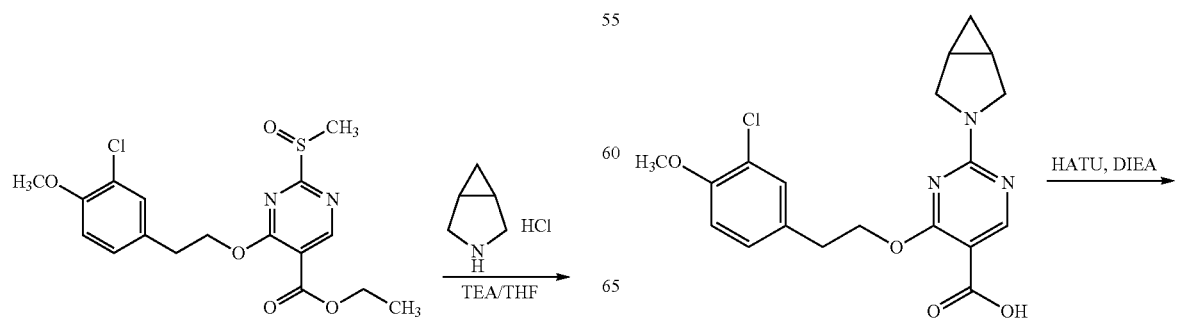

-continued

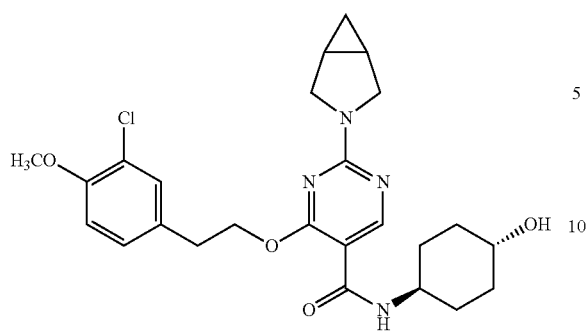

The procedure was the same as Example 1(3), yield 56%.

Molecular Formula: $C_{25}H_{31}ClN_4O_4$ molecular weight: 487.0 mass spectrum (m/e): 487.2 (M+1)

$^1$H NMR (400M, CDCl$_3$) δ: 8.91 (s, 1H), 7.28 (d, 1H), 7.08 (d, 1H), 6.88 (d, 2H), 4.71 (t, 2H), 3.93 (m, 2H), 3.89 (s, 3H), 3.81 (m, 1H), 3.59 (m, 3H), 3.05 (t, 2H), 1.92 (m, 4H), 1.64 (m, 2H), 1.40 (m, 3H), 1.00 (m, 2H), 0.83 (m, 1H), 0.21 (m, 1H).

Example 17

Preparation of 4-(3-chloro-4-methoxybenzyloxy)-N-(4-fluorobenzyl)-2-(5-azaspiro[2.4]heptan-5-yl)pyrimidine-5-carboxamide (Compound 17)

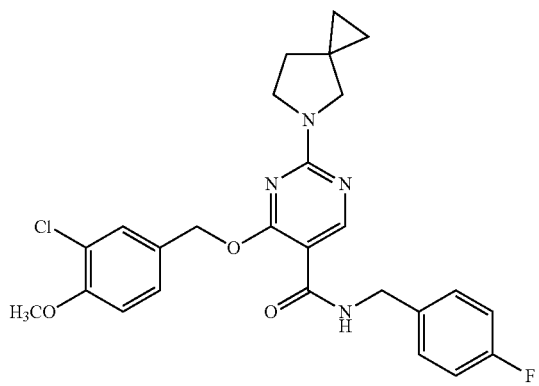 [SMILES: COc1ccc(COc2nc(N3CCC4(CC4)C3)ncc2C(=O)NCc2ccc(F)cc2)cc1Cl]

(1) Preparation of Ethyl 4-(3-chloro-4-methoxybenzyloxy)-2-(5-azaspiro[2.4]heptan-5-yl)pyrimidine-5-carboxylate

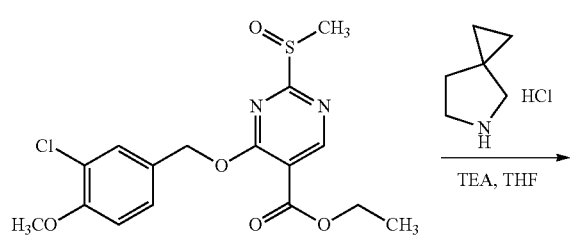

-continued

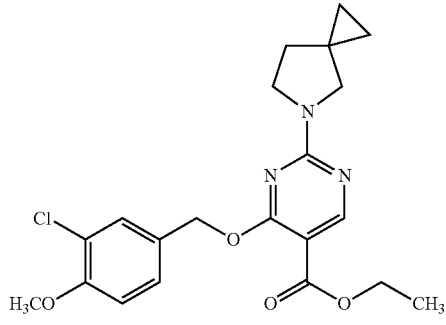

The procedure was the same as Example 1(5), yield 72%.

(2) Preparation of 4-(3-chloro-4-methoxybenzyloxy)-2-(5-azaspiro[2.4]heptan-5-yl)pyrimidine-5-carboxylic acid

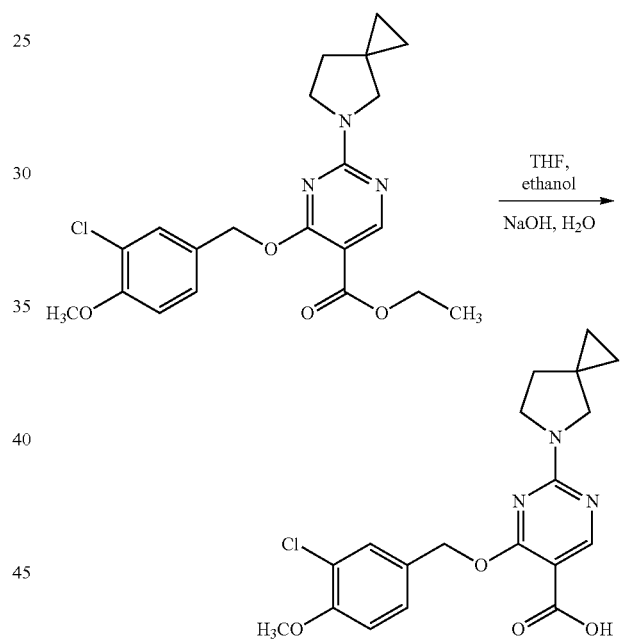

The procedure was the same as Example 1(2), yield 95%.

(3) Preparation of 4-(3-chloro-4-methoxybenzyloxy)-N-(4-fluorobenzyl)-2-(5-azaspiro[2.4]heptan-5-yl)pyrimidine-5-carboxamide

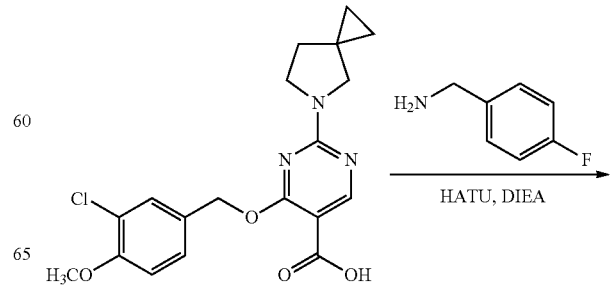

-continued

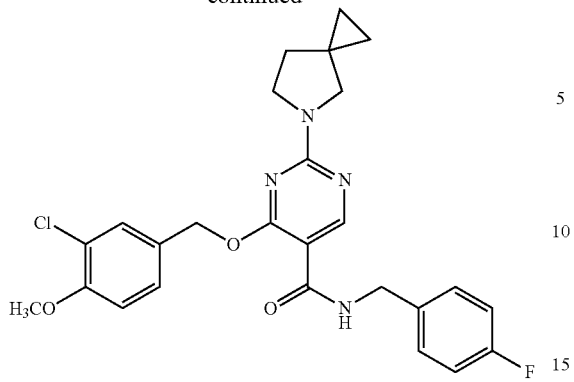

The procedure was the same as Example 1(3), yield 43%.

Molecular Formula: $C_{26}H_{26}ClFN_4O_3$ molecular weight: 497.0 mass spectrum (m/e): 497.2 (M+1)

$^1$H NMR (400M, CDCl$_3$) δ: 8.99 (d, 1H), 7.52 (m, 1H), 7.37 (d, 1H), 7.13 (m, 3H), 6.95 (m, 2H), 6.79 (m, 1H), 5.34 (d, 2H), 4.49 (d, 2H), 3.92 (s, 3H), 3.81 (m, 2H), 3.52 (d, 2H), 1.92 (t, 2H), 0.65 (s, 4H).

Example 18

Preparation of 4-(3-chloro-4-methoxybenzyloxy)-N-(pyrimidin-2-ylmethyl)-2-(5-azaspiro[2.4]heptan-5-yl)-pyrimidine-5-carboxamide (Compound 18)

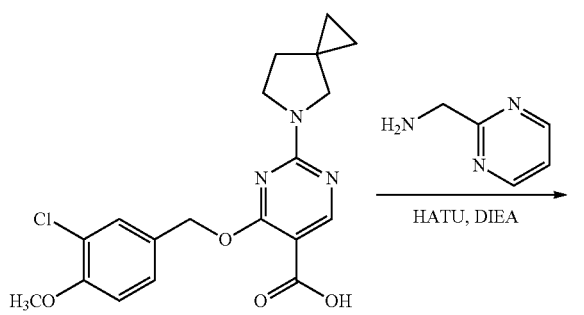

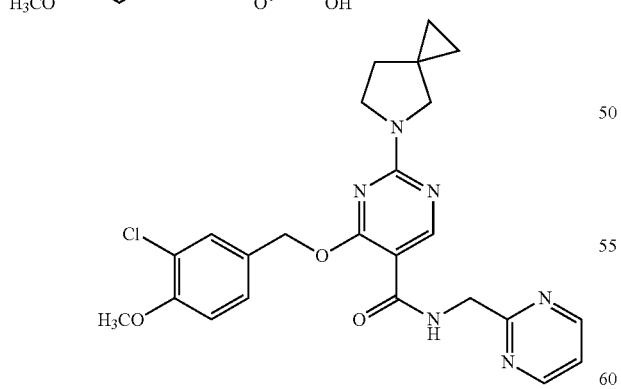

The procedure was the same as Example 1(3), yield 47%.

Molecular Formula: $C_{24}H_{25}ClN_6O_3$ molecular weight: 481.0 mass spectrum (m/e): 481.2 (M+1)

$^1$H NMR (400M, CDCl$_3$) δ: 9.02 (d, 1H), 8.60 (m, 2H), 8.56 (m, 1H), 7.59 (d, 1H), 7.39 (m, 1H), 7.18 (t, 1H), 6.91 (t, 1H), 5.49 (d, 2H), 4.88 (d, 2H), 3.91 (s, 3H), 3.82 (m, 2H), 3.52 (d, 2H), 1.93 (t, 2H), 0.67 (m, 4H).

Example 19

Preparation of 4-(3-chloro-4-methoxybenzyloxy)-N-[(trans)-4-hydroxy cyclohexyl]-2-(5-azaspiro[2.4]heptan-5-yl)-pyrimidine-5-carboxamide (Compound 19)

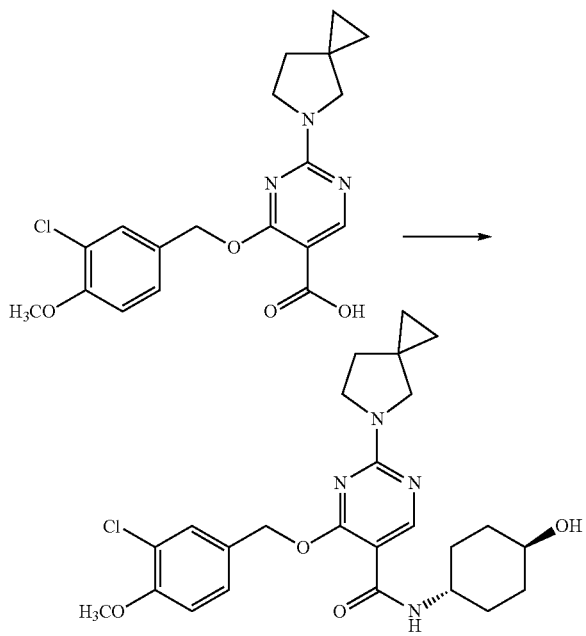

The procedure was the same as Example 1(3), yield 45%.

Molecular Formula: $C_{25}H_{31}ClN_4O_4$ molecular weight: 487.0 mass spectrum (m/e): 487.2 (M+1)

$^1$H NMR (400M, CDCl$_3$) δ: 8.95 (d, 1H), 7.49 (d, 1H), 7.27 (m, 1H), 7.22 (m, 1H), 6.95 (m, 1H), 5.37 (d, 2H), 3.94 (s, 3H), 3.90 (m, 1H), 3.80 (m, 2H), 3.59 (m, 1H), 3.51 (m, 2H), 2.04 (m, 2H), 1.87-1.94 (m, 4H), 1.42 (m, 3H) 1.14 (m, 2H), 0.65 (m, 4H).

Example 20

Preparation of 4-(3-chloro-4-methoxybenzyloxy)-N-[(trans)-4-hydroxy cyclohexyl]-2-(4-azaspiro[2.4]heptan-4-yl)pyrimidine-5-carboxamide (Compound 20)

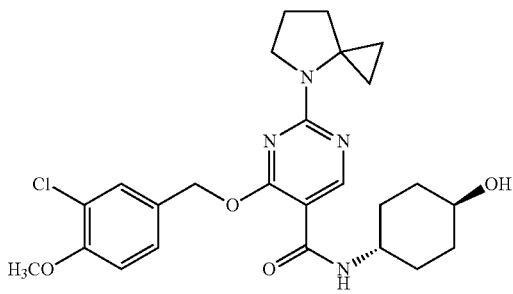 [SMILES: COc1ccc(COc2nc(N3CCCC34CC4)ncc2C(=O)N[C@H]2CC[C@H](O)CC2)cc1Cl]

77

(1) Preparation of ethyl 4-(3-chloro-4-methoxybenzyloxy)-2-(4-azaspiro[2.4]heptan-4-yl)pyrimidine-5-carboxylate

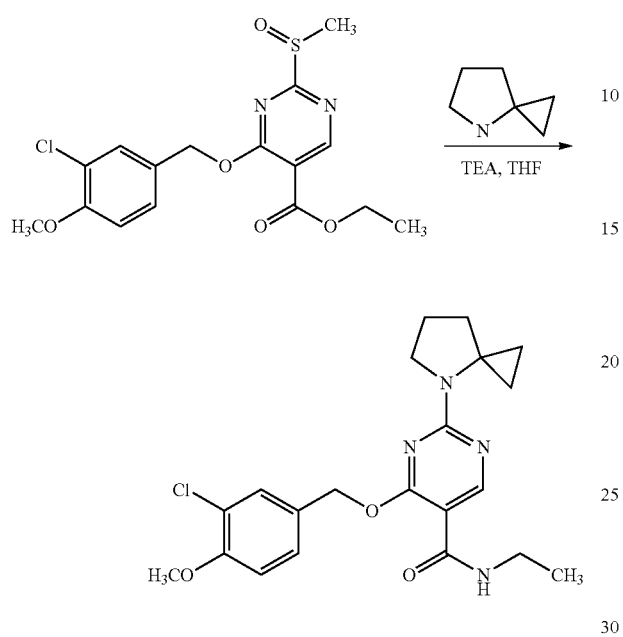

The procedure was the same as Example 1(5), yield 76%.

(2) Preparation of 4-(3-chloro-4-methoxybenzyloxy)-2-(4-azaspiro[2.4]heptan-4-yl)pyrimidine-5-carboxylic acid

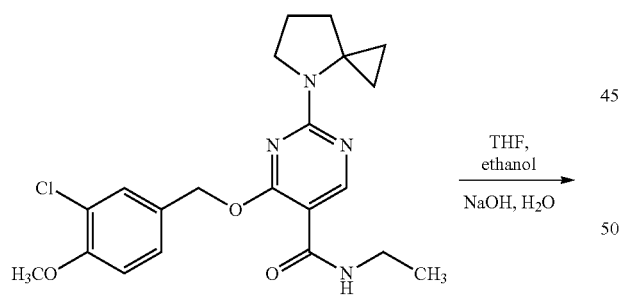

78

The procedure was the same as Example 1(2), yield 91%.

(3) Preparation of 4-(3-chloro-4-methoxybenzyloxy)-N-[(trans)-4-hydroxycyclohexyl]-2-(4-azaspiro[2.4]heptan-4-yl)pyrimidine-5-carboxamide

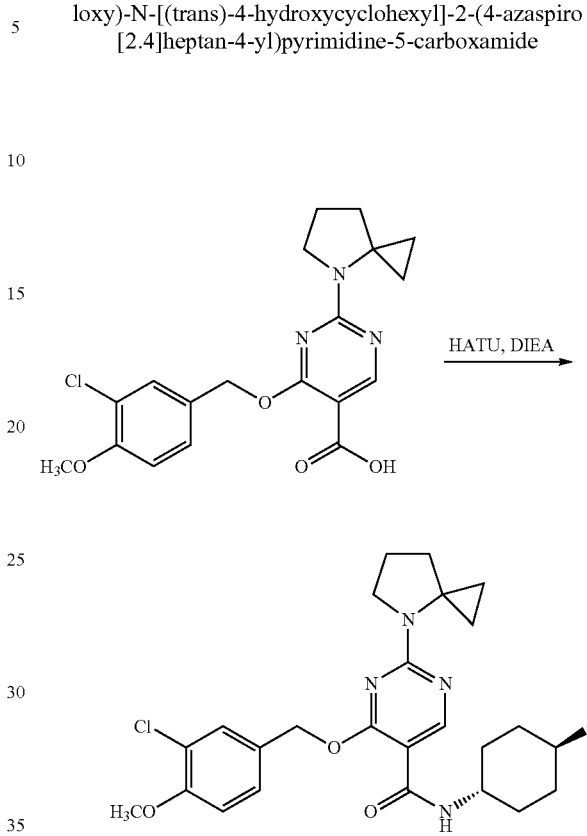

The procedure was the same as Example 1(3), yield 53%.
Molecular Formula: $C_{25}H_{31}ClN_4O_4$ molecular weight: 487.0 mass spectrum (m/e): 487.3 (M+1)
$^1$H NMR (400M, CDCl$_3$) δ: 8.89 (br s, 1H), 7.47 (d, 1H), 7.28 (m, 1H), 7.17 (m, 1H), 6.95 (d, 1H), 5.26 (m, 2H), 3.94 (s, 3H), 3.87 (m, 3H), 3.57 (m, 1H), 2.10 (m, 2H), 2.02 (m, 6H), 1.86 (m, 2H), 1.41 (m, 3H), 1.10 (m, 2H), 0.55 (s, 2H).

Example 21

Preparation of 4-(3-chloro-4-methoxybenzyloxy)-N-(4-fluorobenzyl)-2-(6-azaspiro[2.5]octan-6-yl)pyrimidine-5-carboxamide (Compound 21)

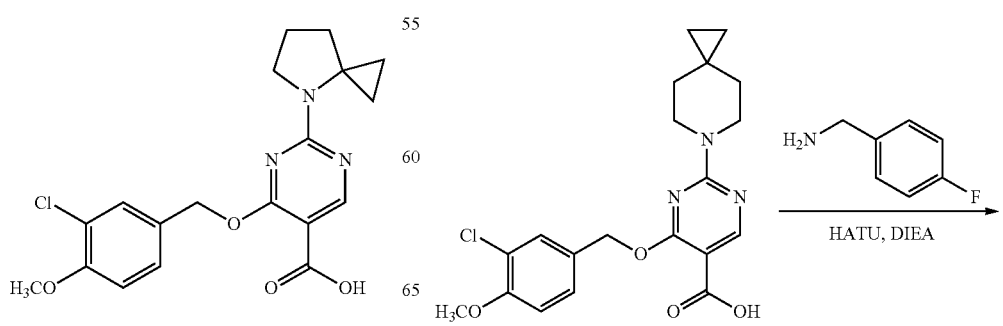

-continued

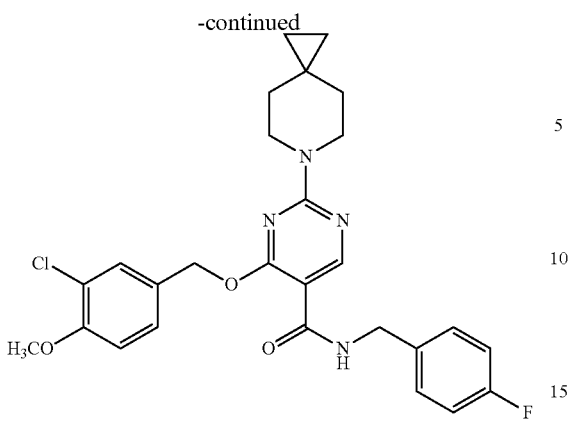

The procedure was the same as Example 1(3), yield 44%.
Molecular Formula: $C_{27}H_{28}ClFN_4O_3$ molecular weight: 511.0 mass spectrum (m/e): 511.2 (M+1)
$^1$H NMR (400M, CDCl$_3$) δ: 8.98 (s, 1H), 7.51 (m, 1H), 7.36 (d, 1H), 7.15 (m, 3H), 6.93 (m, 2H), 6.79 (d, 1H), 5.30 (s, 2H), 4.49 (d, 2H), 3.93 (m, 4H), 3.92 (s, 3H), 1.43 (t, 4H), 0.40 (s, 4H).

The contents of all documents as cited in the present application are incorporated herein by reference. Unless specified otherwise, all technological and scientific terms herein have their common meanings well-known in the art.

Those skilled in the art would understand or determine many equivalents of embodiments of the present invention via conventional experimental means, and these equivalents are covered by the scope of the appending claims.

What is claimed is:
1. A compound of Formula (I), and its pharmaceutically acceptable salts or stereoisomers thereof:

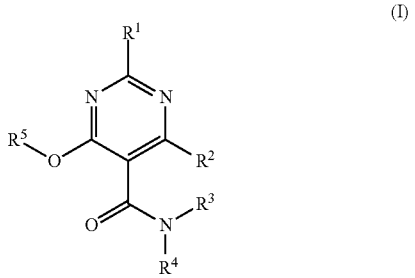

(I)

wherein
R$^1$ represents 6-7-membered nitrogen-containing hetero fused ring group, 7-12-membered nitrogen-containing hetero spiro ring group, or 7-12-membered nitrogen-containing hetero bridged ring group, each of which is linked to pyrimidine ring via N and is unsubstituted or substituted with 1-4 substituents, wherein
the substituents are selected from halogen atoms, cyano, amino, hydroxy, C$_{1-6}$alkyl, haloC$_{1-6}$alkyl, hydroxy C$_{1-6}$alkyl, C$_{1-6}$alkoxy, C$_{1-6}$alkylcarbonyl or C$_{1-6}$alkoxycarbonyl;
R$^2$ represents hydrogen atom, hydroxy, amino, cyano, C$_{1-6}$alkylamino, di(C$_{1-6}$alkyl)amino, C$_{1-6}$alkyl, halo C$_{1-6}$alkyl, hydroxy C$_{1-6}$alkyl or C$_{1-6}$alkoxy;
R$^3$ and R$^4$ each independently represent hydrogen atom or -M-R$^7$, wherein
M represents a single bond, or C$_{1-6}$alkylidene, represented by —(CH$_2$)$_t$— (t is an integer from 1 to 6), unsubstituted or substituted with 1-4 substituents, and R$^7$ represents a cyclic group other than adamantyl, which is unsubstituted or substituted with 1-4 substituents,
or R$^3$ and R$^4$ together with the nitrogen atom to which they link form a 5-7-membered nitrogen-containing hetero ring group unsubstituted or substituted with 1-4 substituents, wherein
the substituents are selected from halogen atoms, hydroxy, cyano, amino, C$_{1-6}$alkylamino, di(C$_{1-6}$alkyl)amino, oxo, C$_{1-6}$alkyl, hydroxyC$_{1-6}$alkyl, haloC$_{1-6}$ alkyl, C$_{1-6}$alkoxy, C$_{1-6}$alkylcarbonyl, C$_{1-6}$alkylsulfonyl or di(C$_{1-6}$alkyl)phosphino; and
R$^5$ represents hydrogen atom or -Q-R$^8$, wherein
Q represents a single bond, or C$_{1-6}$alkylidene, represented by —(CH$_2$)$_t$— (t is an integer from 1 to 6), unsubstituted or substituted with 1-4 substituents, and
R$^8$ represents 6-14-membered aryl, 5-7-membered heteromonocyclic group or 6-14-membered fused ring group, each of which is unsubstituted or substituted with 1-4 substituents, wherein
the substituents are selected from halogen atoms, hydroxy, C$_{1-6}$alkyl, haloC$_{1-6}$alkyl, carboxylC$_{1-6}$alkyl, C$_{2-6}$alkenyl, C$_{2-6}$alkynyl, C$_{1-8}$alkoxy, haloC$_{1-8}$alkoxy, amino, C$_{1-6}$alkylamino, di(C$_{1-6}$alkyl)amino, cyano, nitro, C$_{1-6}$alkylcarbonyl, sulfonylamino or C$_{1-6}$alkylsulfonylamino.

2. The compound according to claim 1, and its pharmaceutically acceptable salts or stereoisomers thereof:
wherein R$^2$ represents hydrogen atom, hydroxy or methyl; and R$^4$ represents hydrogen atom.

3. The compound according to claim 2, and its pharmaceutically acceptable salts or stereoisomers thereof:
wherein R$^5$ represents -Q-R$^8$, wherein
Q is selected from C$_{1-6}$alkylidene, represented by —(CH$_2$)$_t$— (t is an integer from 1 to 6, unsubstituted or substituted with 1-3 substituents, and
R$^8$ is selected from 6-14-membered aryl, 5-7-membered heteromonocyclic group or 6-14-membered fused ring group, each of which is unsubstituted or substituted with 1-3 substituents, wherein
the substituents are selected from halogen atoms, hydroxy, C$_{1-6}$alkyl, haloC$_{1-6}$alkyl, carboxylC$_{1-6}$alkyl, C$_{1-8}$alkoxy, haloC$_{1-8}$alkoxy, amino, C$_{1-6}$alkylamino, di(C$_{1-6}$alkyl)amino, cyano, nitro, C$_{1-6}$alkylcarbonyl, sulfonylamino or C$_{1-6}$alkylsulfonylamino.

4. The compound according to claim 3, and its pharmaceutically acceptable salts or stereoisomers thereof:
wherein
R$^1$ is selected from 6-7-membered nitrogen-containing hetero fused ring group, 7-10-membered nitrogen-containing hetero spiro ring group, or 7-8-membered nitrogen-containing hetero bridged ring group, each of which is linked to pyrimidine ring via N and is unsubstituted or substituted with 1-3 substituents, wherein
the substituents are selected from halogen atoms, cyano, amino, hydroxy, C$_{1-6}$alkyl, haloC$_{1-6}$alkyl, hydroxyC$_{1-6}$ alkyl or C$_{1-6}$alkoxy;
R$^3$ is selected from -M-R$^7$, wherein
M represents a single bond or C$_{1-6}$alkylidene, represented by —(CH$_2$)$_t$— (t is an integer from 1 to 6, unsubstituted or substituted with 1-4 substituents, and
R$^7$ is selected from phenyl, 5-7-membered heteromonocyclic group, 4-7-membered cycloalkyl, 6-14-membered fused ring group, 7-10-membered spiro ring group, or 7-10-membered bridged ring group other than adamantyl, each of which is unsubstituted or substituted with 1-3 substituents,
or
R$^3$ and R$^4$ together with the nitrogen atom to which they link form a 5-6-membered nitrogen-containing hetero ring group, which is unsubstituted or substituted, wherein the substituents are selected from halogen atoms, hydroxy, cyano, amino, C$_{1-6}$alkylamino, di(C$_{1-6}$alkyl)amino, oxo, C$_{1-6}$alkyl, hydroxyC$_{1-6}$alkyl, haloC$_{1-6}$alkyl or C$_{1-6}$alkoxy; and R$^5$ represents -Q-R$^8$, wherein Q is selected from methylidene, represented by —CH$_2$—, unsubstituted or substituted with 1-2 substituents, or ethylidene unsubstituted or substituted with 1-3 substituents, and R$^8$ is selected from phenyl, 5-7-membered heteromonocyclic group, or 6-14-membered fused ring group, each of which is unsubstituted or substituted with 1-3 substituents, wherein the substituents are selected from C$_{1-3}$alkyl, fluorine, chlorine, methoxy, ethoxy, trifluoromethoxy, dimethylamino or carboxymethyl.

5. The compound according to claim 4, and its pharmaceutically acceptable salts or stereoisomers thereof:

wherein

R$^1$ is selected from 6-7-membered nitrogen-containing hetero fused ring group, 7-10-membered nitrogen-containing hetero spiro ring group, or 7-8-membered nitrogen-containing hetero bridged ring group, each of which is linked to pyrimidine ring via N and is unsubstituted or substituted with 1-3 substituents, wherein the substituents are selected from halogen atoms, cyano, amino, hydroxy, C$_{1-6}$alkyl, haloC$_{1-6}$alkyl, hydroxy C$_{1-6}$alkyl or C$_{1-6}$alkoxy;

R$^2$ represents hydrogen atom, hydroxy or methyl;

R$^4$ is selected from hydrogen atom;

R$^3$ is selected from -M-R$^7$, wherein

M represents a single bond or C$_{1-6}$alkylidene, represented by —(CH$_2$)$_t$— (t is an integer from 1 to 6), unsubstituted or substituted with 1-2 substituents, and R$^7$ is selected from phenyl, 5-7-membered heteromonocyclic group, 4-7-membered cycloalkyl, 8-10-membered fused ring group, or 7-10-membered spiro ring group, each of which is unsubstituted or substituted with 1-3 substituents, or R$^3$ and R$^4$ together with the nitrogen atom to which they link form a 5-6-membered nitrogen-containing hetero ring group, which is unsubstituted or substituted, wherein the substituents are selected from halogen atoms, hydroxy, cyano, amino, C$_{1-6}$alkylamino, di(C$_{1-6}$alkyl)amino, oxo, C$_{1-6}$alkyl, hydroxy C$_{1-6}$alkyl, haloC$_{1-6}$alkyl or C$_{1-6}$alkoxy; and R$^5$ represents -Q-R$^8$, wherein Q is selected from methylidene, represented by —CH$_2$—, or ethylidene, represented by —CH$_2$CH$_2$—, unsubstituted or substituted with 1-2 substituents, and R$^8$ is selected from phenyl, 5-7-membered heteromonocyclic group, or 8-10-membered fused ring group, each of which is unsubstituted or substituted with 1-3 substituents, wherein the substituents are selected from C$_{1-3}$alkyl, fluorine, chlorine, methoxy, ethoxy, trifluoromethoxy, dimethylamino or carboxymethyl.

6. The compound according to claim 5, and its pharmaceutically acceptable salts or stereoisomers thereof:

wherein

R$^1$ is selected from a group consisting of:

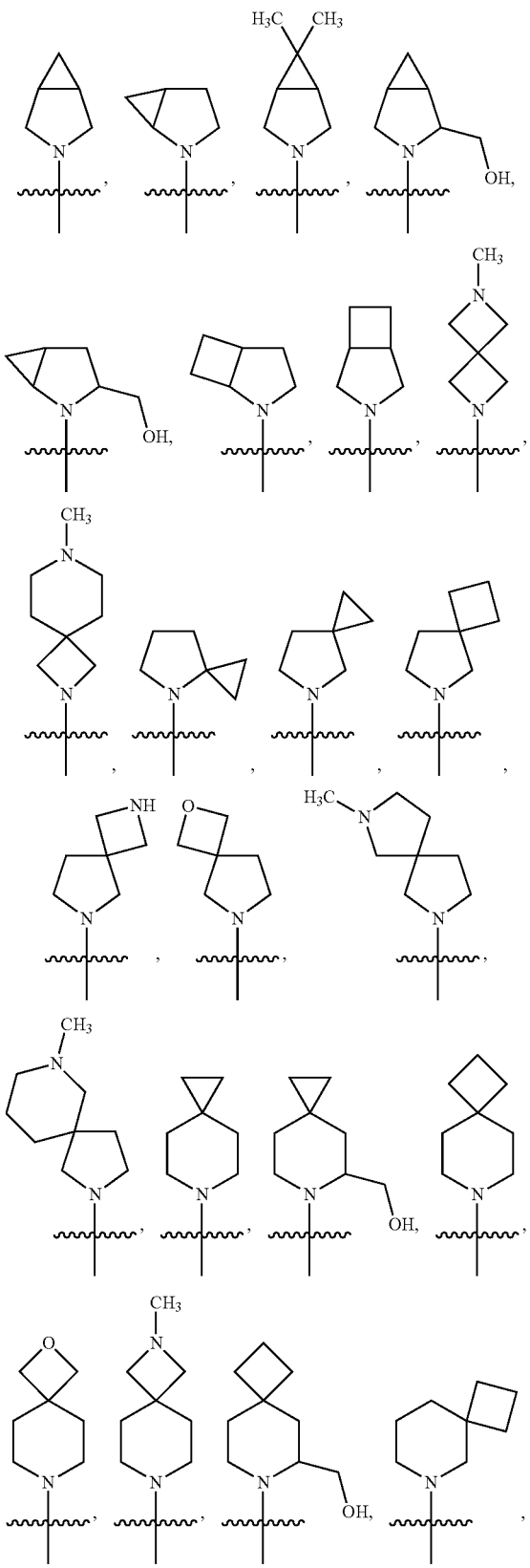

-continued
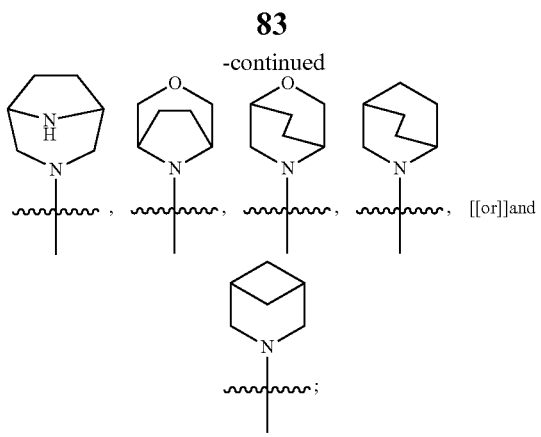
$R^2$ is hydrogen atom;
$R^4$ is hydrogen atom;
$R^3$ is selected from a group consisting of:
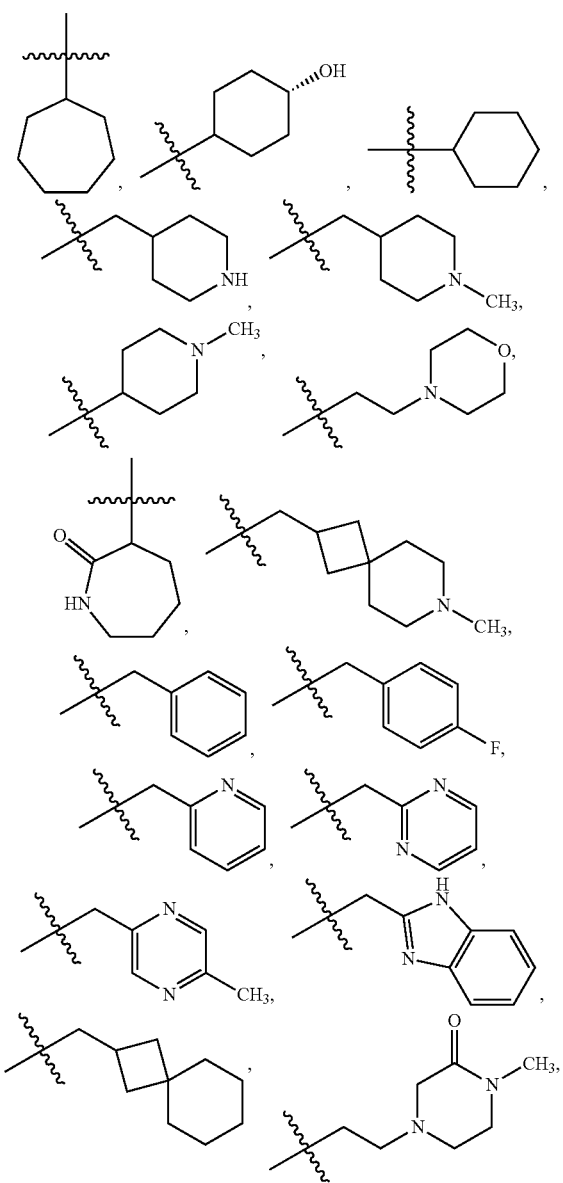
-continued
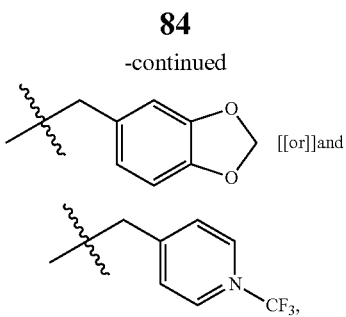
or
$R^3$ and $R^4$ together with the nitrogen atom to which they link form:
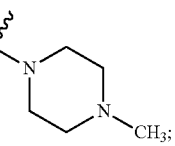
and
$R^5$ is selected from a group consisting of:
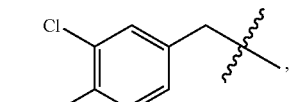
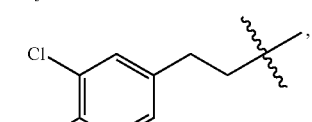
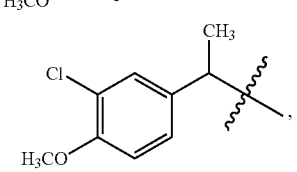
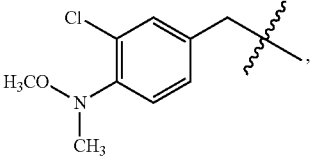
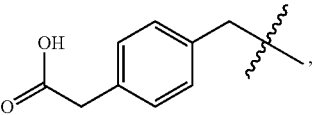
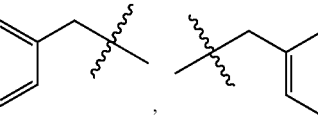
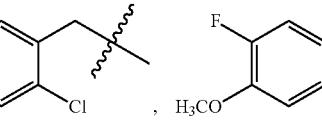

-continued
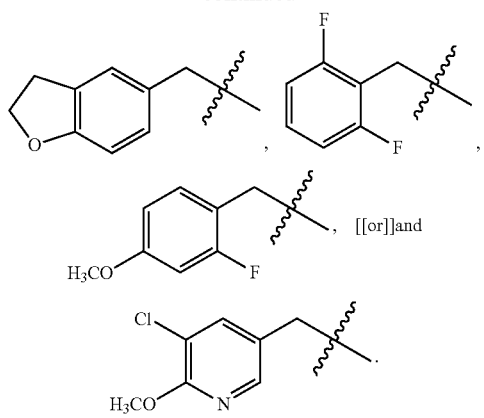
7. The compound according to claim 6, and its pharmaceutically acceptable salts or stereoisomers thereof:
wherein
R¹ is selected from a group consisting of:
-continued
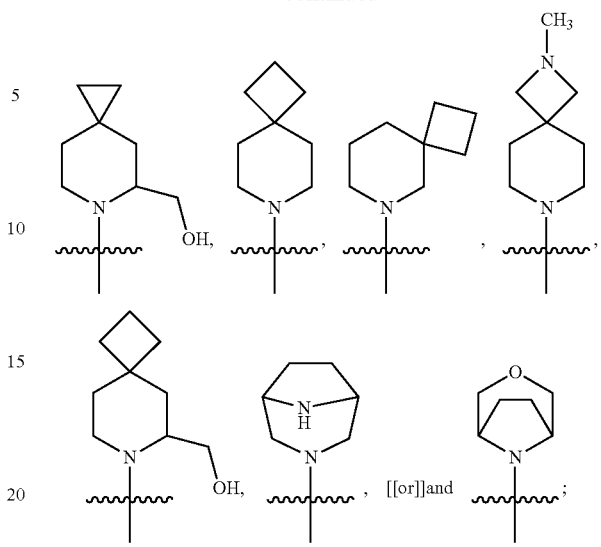
R² is hydrogen atom;
R³ is selected from a group consisting of:
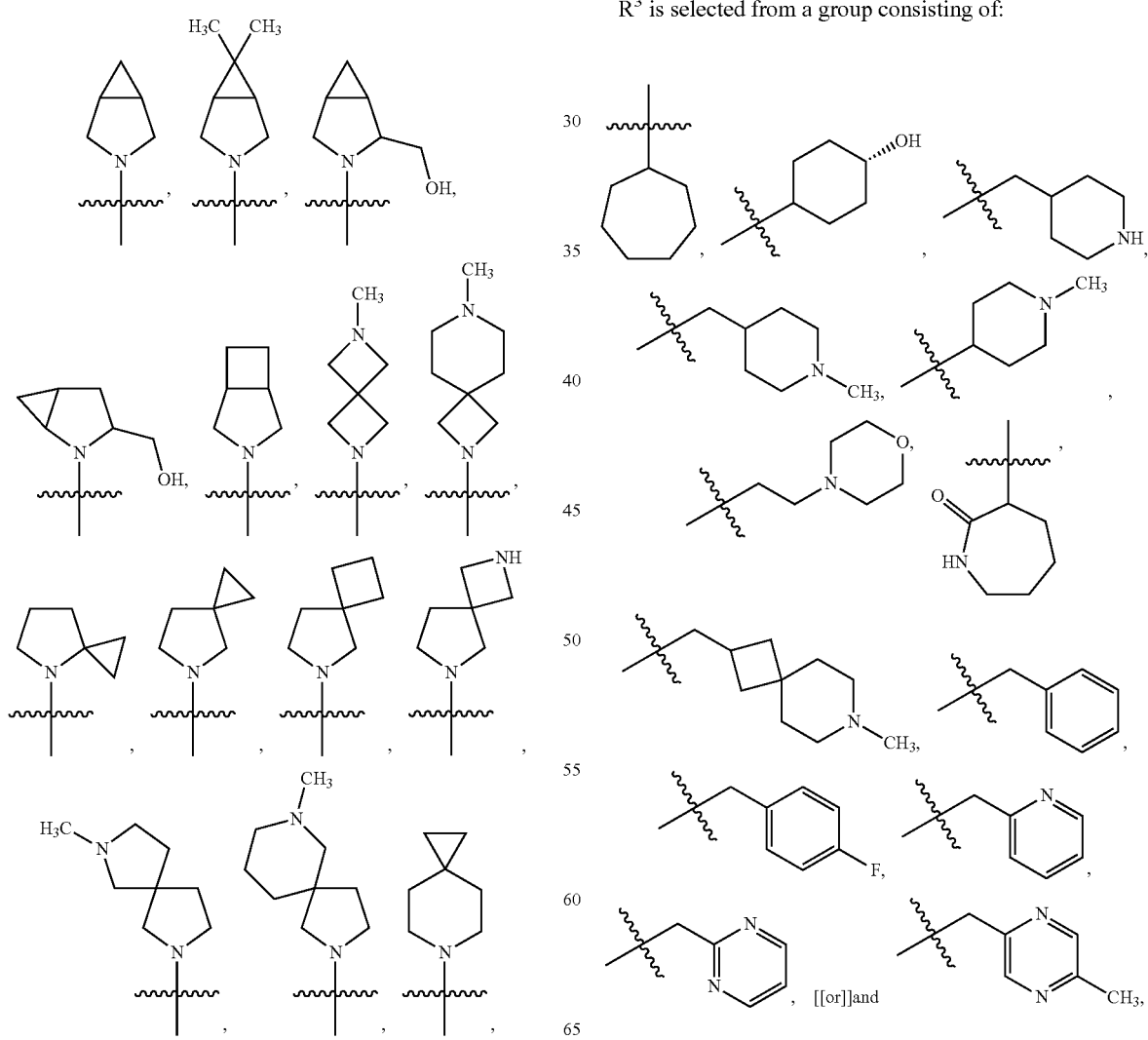

$R^4$ is hydrogen atom; and
$R^5$ is selected from a group consisting of:
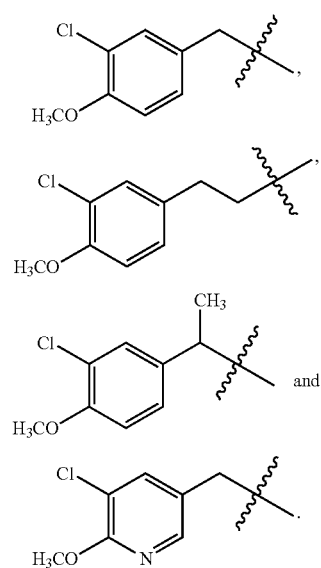
8. The compound according to claim 7, and its pharmaceutically acceptable salts or stereoisomers thereof:
wherein
$R^1$ is selected from a group consisting of:
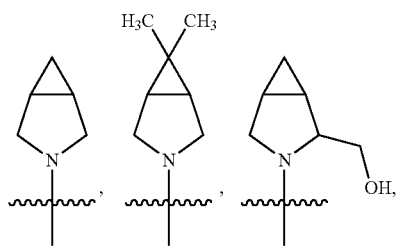
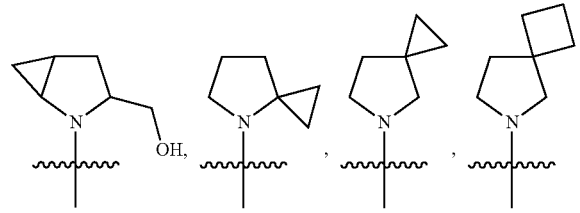
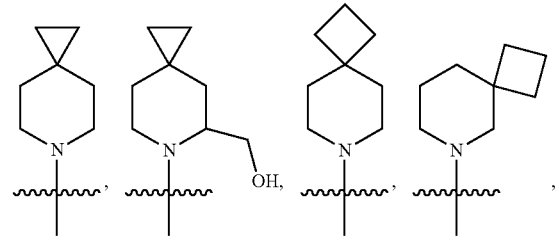
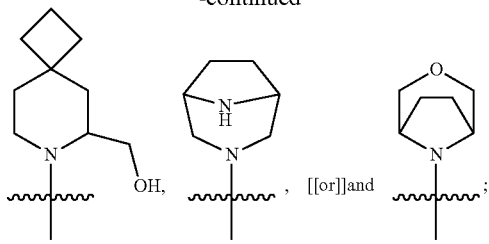
$R^2$ is hydrogen atom;
$R^3$ is selected from a group consisting of:
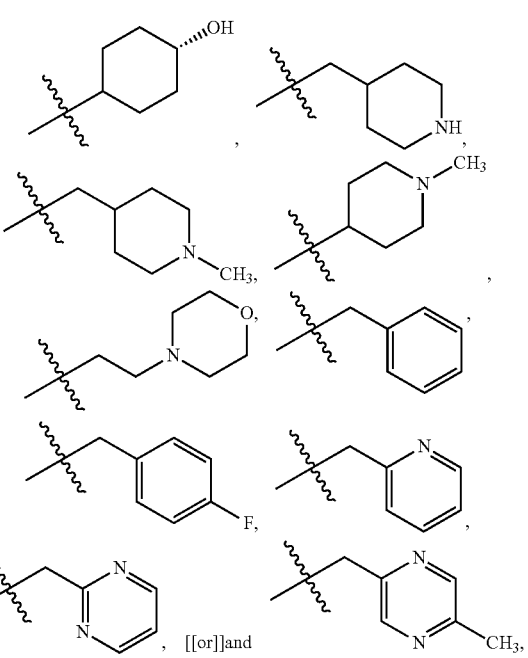
$R^4$ is hydrogen atom;
$R^5$ is selected from a group consisting of:
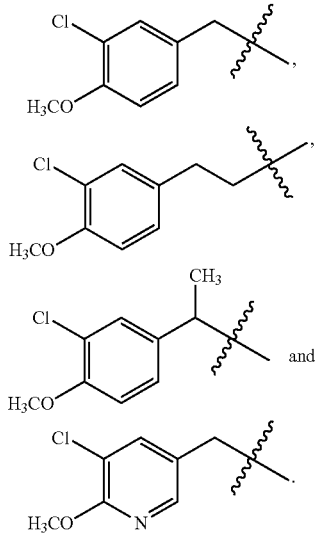

9. The compound according to claim 8, and its pharmaceutically acceptable salts or stereoisomers thereof:
wherein R¹ is selected from a group consisting of:

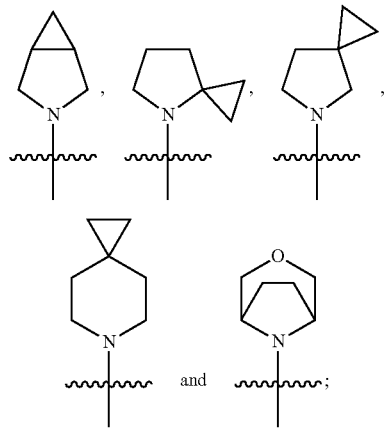

R² is hydrogen atom;
R³ is selected from a group consisting of:

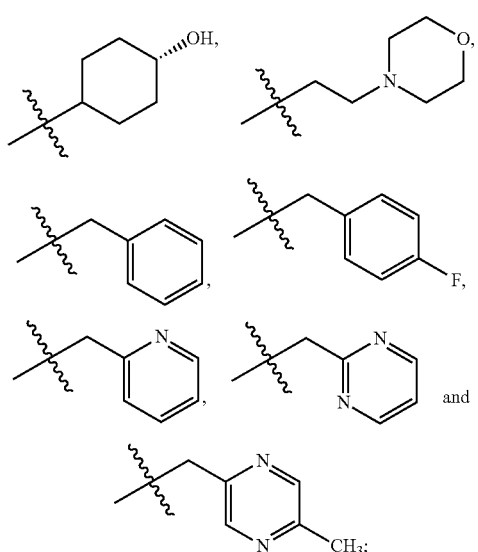

R⁴ is hydrogen atom; and
R⁵ is selected from a group consisting of:

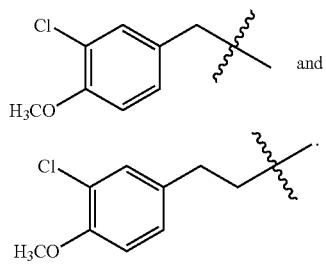

10. The compound according to claim 9, and its pharmaceutically acceptable salts or stereoisomers thereof, which is selected from:

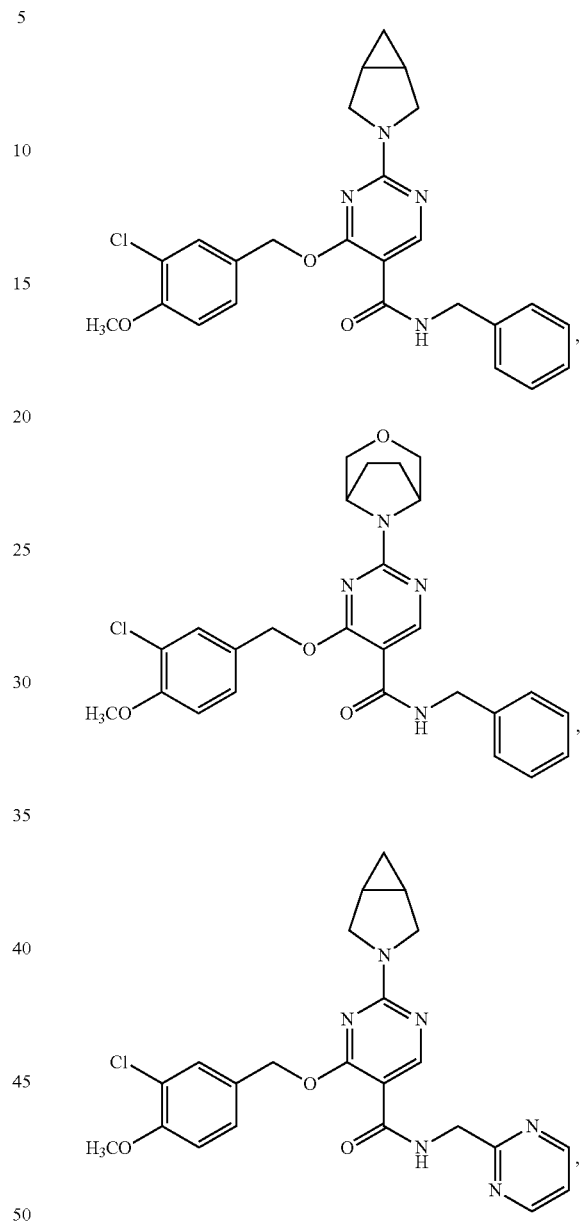

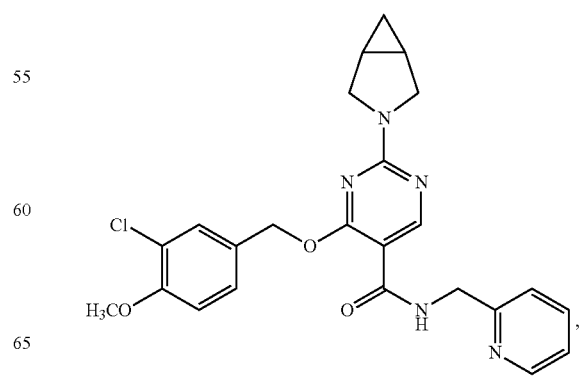

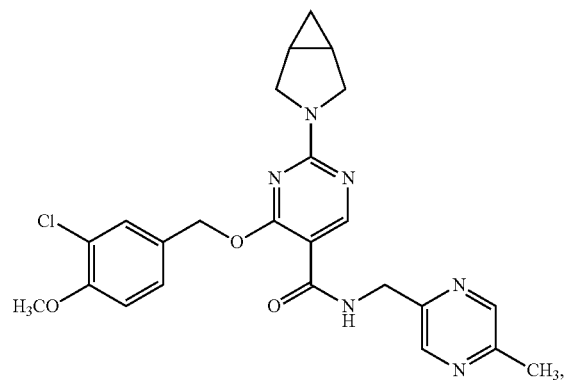
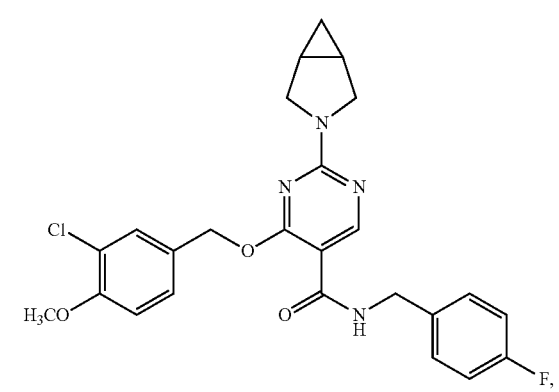
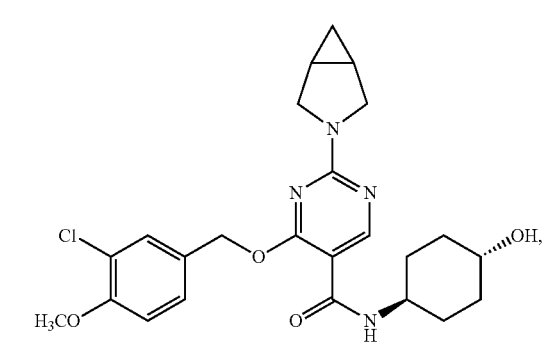
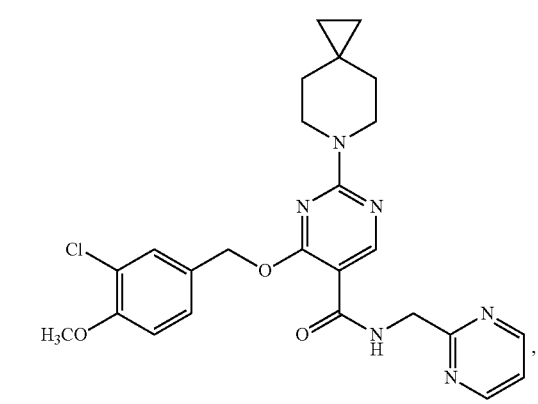
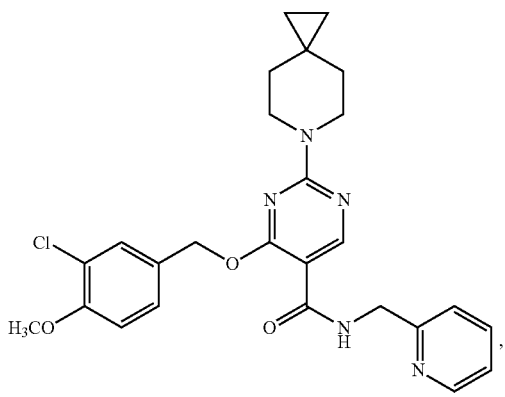
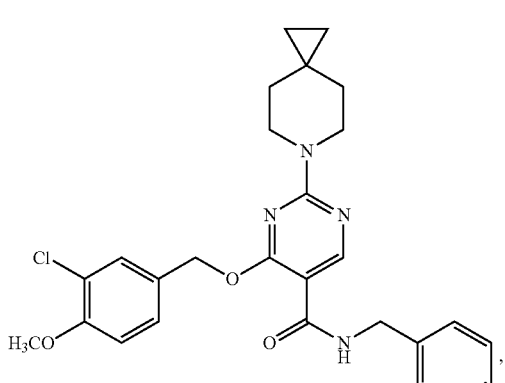
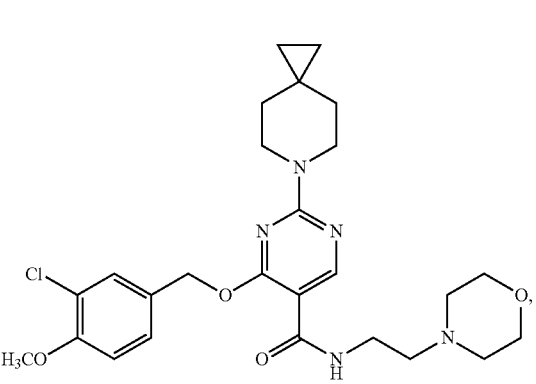
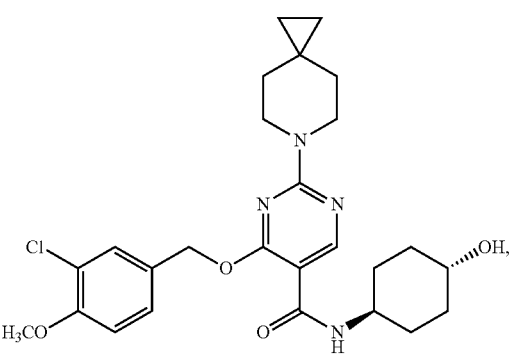

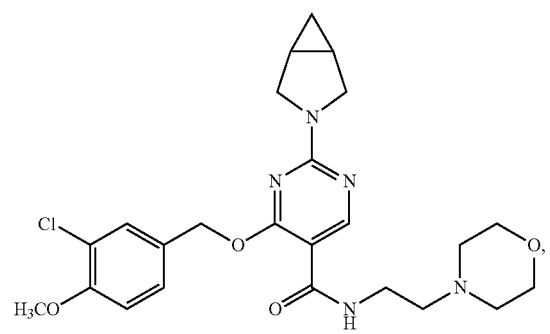
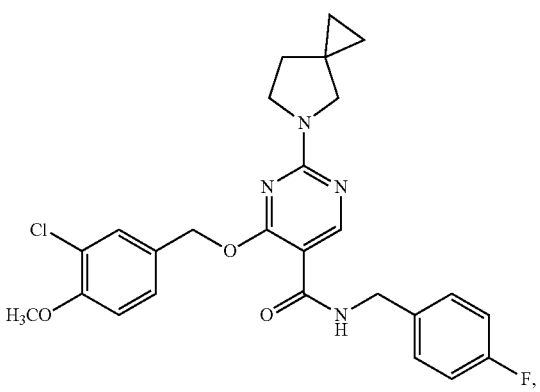
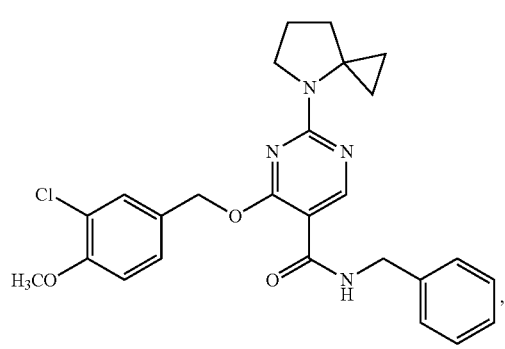
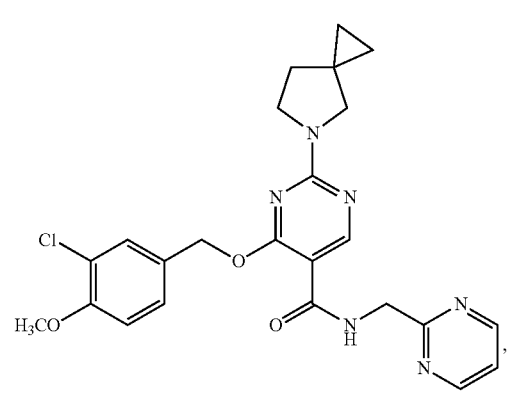
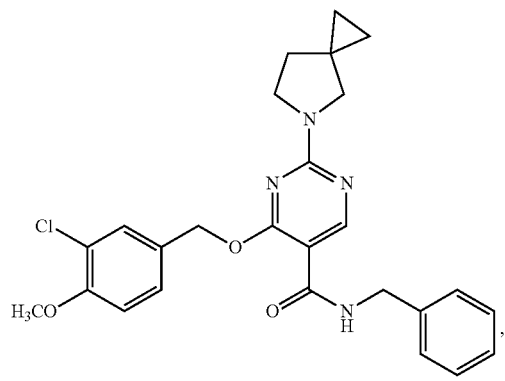
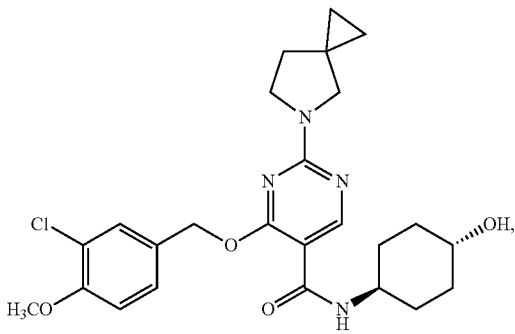
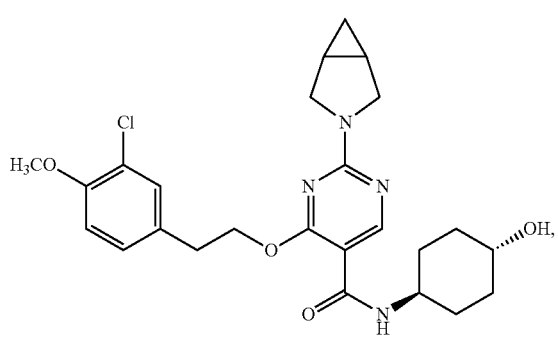
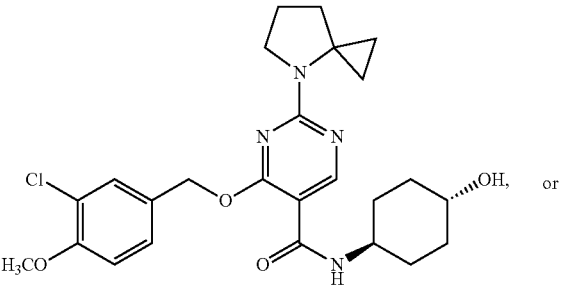 or -continued 11. A pharmaceutical preparation comprising the compound according to claim 1, pharmaceutically acceptable salts or stereoisomers thereof, in conjunction with one or more pharmaceutically acceptable carriers.

12. A method for inhibiting PDE-5 activity or enhancing cGMP signal transduction comprising contacting the compound of Formula (I) according to claim 1, or a pharmaceutically acceptable salt or stereoisomer thereof, with a cell.

13. A method of treating erectile dysfunction or female sexual dysfunction comprising administering an effective amount of the compound of Formula (I) according to claim 1, or a pharmaceutically acceptable salt or stereoisomer thereof, to a subject in need thereof.

* * * * *

UNITED STATES PATENT AND TRADEMARK OFFICE
CERTIFICATE OF CORRECTION

PATENT NO. : 8,980,904 B2
APPLICATION NO. : 14/233823
DATED : March 17, 2015
INVENTOR(S) : Yongqian Wu et al.

It is certified that error appears in the above-identified patent and that said Letters Patent is hereby corrected as shown below:

IN THE CLAIMS:

Column 80, line 33, Claim 3 please delete "(t is an integer from 1 to 6," and replace with -- (t is an integer from 1 to 6), --

Column 80, line 56, Claim 4 please delete "(t is an integer from 1 to 6," and replace with -- (t is an integer from 1 to 6), --

Column 83, line 7, Claim 6 please delete "[[or]]and" and replace with -- and --

Column 84, line 4, Claim 6 please delete "[[or]]and" and replace with -- and --

Column 85, line 10, Claim 6 please delete "[[or]]and" and replace with -- and --

Column 86, line 20, Claim 7 please delete "[[or]]and" and replace with -- and --

Column 86, line 64, Claim 7 please delete "[[or]]and" and replace with -- and --

Column 88, line 8, Claim 8 please delete "[[or]]and" and replace with -- and --

Column 88, line 40, Claim 8 please delete "[[or]]and" and replace with -- and --

Signed and Sealed this
Twenty-ninth Day of December, 2015

Michelle K. Lee
*Director of the United States Patent and Trademark Office*